(12) United States Patent
Kaelin, Jr. et al.

(10) Patent No.: US 7,985,563 B2
(45) Date of Patent: *Jul. 26, 2011

(54) HIFαPROLYL HYDROXYLATION ASSAY

(75) Inventors: William G. Kaelin, Jr., Boston, MA (US); Mircea Ivan, Cambridge, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 192 days.

This patent is subject to a terminal disclaimer.

(21) Appl. No.: 11/879,300

(22) Filed: Jul. 17, 2007

(65) Prior Publication Data

US 2009/0029400 A1 Jan. 29, 2009

Related U.S. Application Data

(63) Continuation of application No. 11/027,273, filed on Dec. 30, 2004, now abandoned, which is a continuation of application No. 10/859,935, filed on Jun. 2, 2004, now abandoned, which is a continuation of application No. 10/101,812, filed on Mar. 19, 2002, now Pat. No. 6,855,510.

(60) Provisional application No. 60/345,132, filed on Dec. 20, 2001, provisional application No. 60/345,131, filed on Dec. 20, 2001, provisional application No. 60/342,598, filed on Dec. 20, 2001, provisional application No. 60/345,200, filed on Nov. 9, 2001, provisional application No. 60/332,493, filed on Nov. 9, 2001, provisional application No. 60/332,334, filed on Nov. 9, 2001, provisional application No. 60/277,440, filed on Mar. 20, 2001, provisional application No. 60/277,431, filed on Mar. 20, 2001, provisional application No. 60/277,425, filed on Mar. 20, 2001.

(51) Int. Cl.
*C12Q 1/34* (2006.01)
(52) U.S. Cl. ............................................ 435/18; 435/23
(58) Field of Classification Search .................... 435/23, 435/18
See application file for complete search history.

(56) References Cited

U.S. PATENT DOCUMENTS

| 5,021,404 A | | 6/1991 | Folkman et al. | |
|---|---|---|---|---|
| 5,206,343 A | * | 4/1993 | Henke et al. | 530/331 |
| 6,855,510 B2 | * | 2/2005 | Kaelin et al. | 435/23 |
| 7,176,345 B2 | * | 2/2007 | Kaelin et al. | 800/18 |

FOREIGN PATENT DOCUMENTS

| EP | 0344682 A2 | 12/1989 |
|---|---|---|
| WO | WO-99/30562 A1 | 6/1999 |
| WO | WO 00/69908 | * 11/2000 |
| WO | WO-00/69908 A1 | 11/2000 |

OTHER PUBLICATIONS

Epstein, Andrew C.R., et al., "C Elegans EGL-9 and Mammalian Homologs Define a Family of Dioxygenases that Regulate HIF by Prolyl Hydroxylation," Cell (2001) 107:43-54.

Ingber, Donald and Folkman, Judah, "Inhibition of Angiogenesis Through Modulation of Collagen Metabolism," Laboratory Investigation (1988) 59(1):44-51.

Ivan, Mircea, et al., "Biochemical Purification and Pharmacological Inhibition of a Mammalian Prolyl Hydroxylase Acting on Hypoxia-Inducible Factor," PNAS (2002) 99(21):13459-13464.

Ivan, Mircea, et al., "HIFα Targeted for VHL-Mediated Destruction by Proline Hydroxylation: Implications for O2 Sensing," Science (2001) 292:464-468.

Jaakkola, Panu, et al., "Targeting of HIFα to the von Hippel-Lindau Ubiquitylation Complex by O2-Regulated Prolyl Hydroxylation," Science (2001) 292:468-472.

Nwogu, John I., et al., "Inhibition of Collagen Synthesis With Prolyl 4-Hydroxylase Inhibitor Improves Left Ventricular Function and Alters the Pattern of Left Ventricular Dilatation After Myocardial Infarction," Circulation (2001) 104(18):2216-2221.

Deo, Sapna K., et al., "Bioluminescence Detection of Proteolytic Bond Cleavage by Using Recombinant Aequorin," Analytical Biochem. (2000) 281:87-94.

Misteli, Tom and Spector, David L., "Application of the Green Fluorescent Protein in Cell Biology and Biotechnology," Nature Biotech. (1997) 15:961-964.

* cited by examiner

*Primary Examiner* — Ralph Gitomer
(74) *Attorney, Agent, or Firm* — FibroGen, Inc.; Christopher M. Turner

(57) ABSTRACT

The present invention provides methods of identifying compounds that decrease proline hydroxylation of the alpha subunit of hypoxia inducible factor (HIFα).

11 Claims, 34 Drawing Sheets

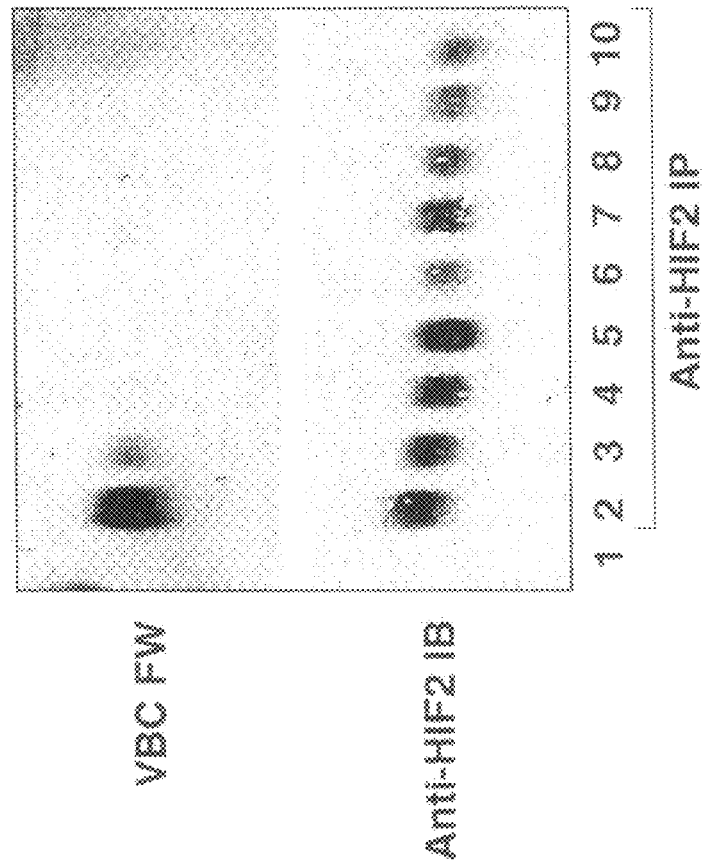
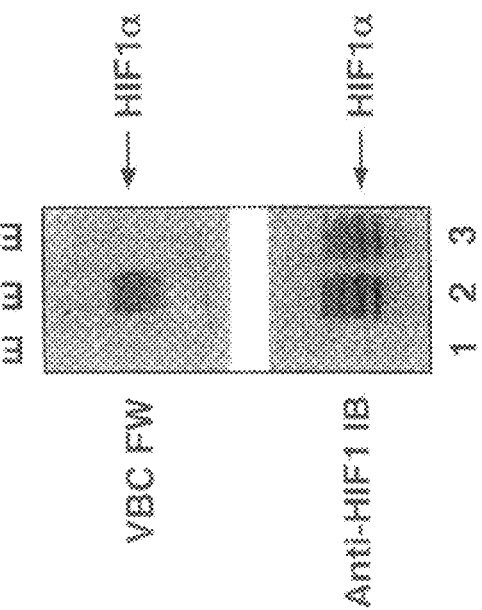

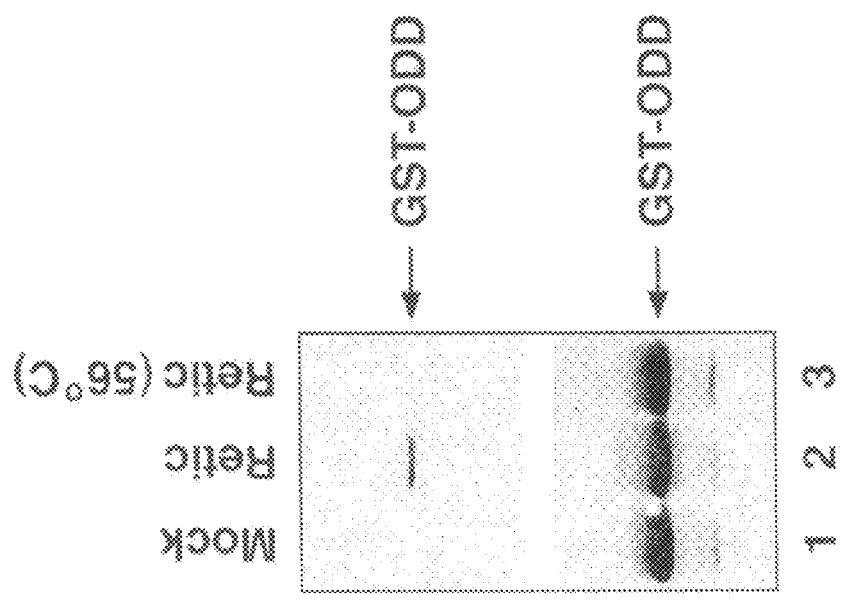
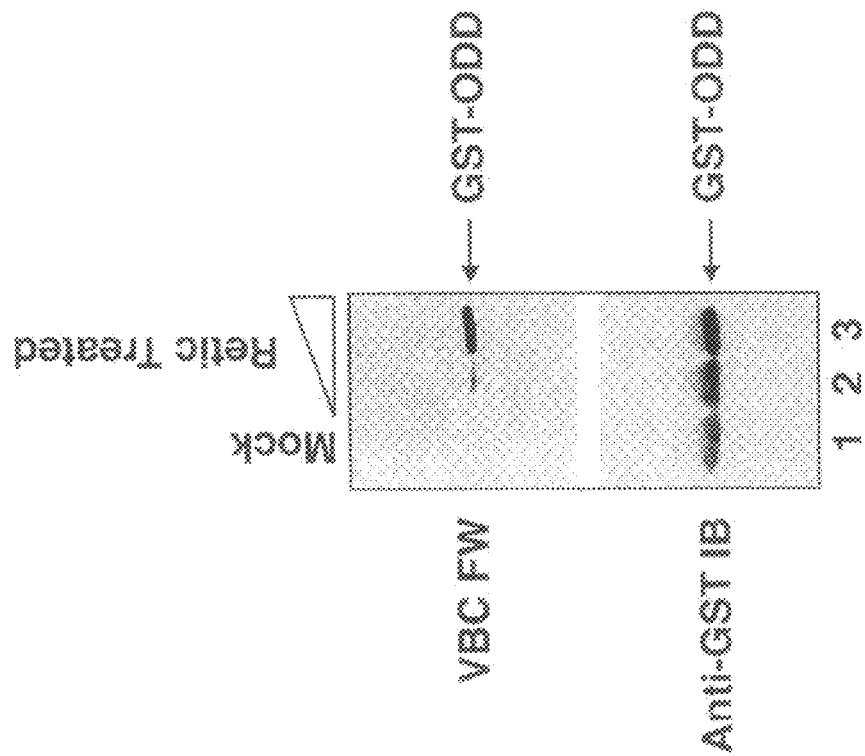

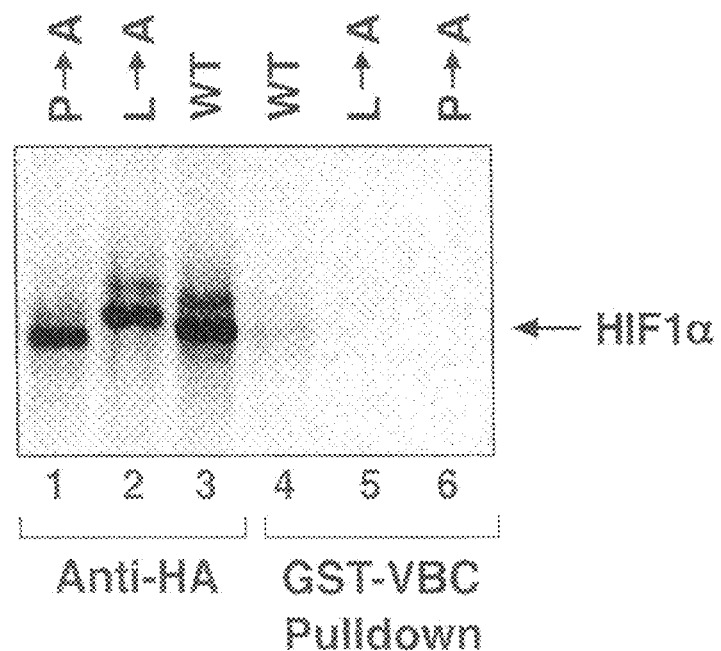
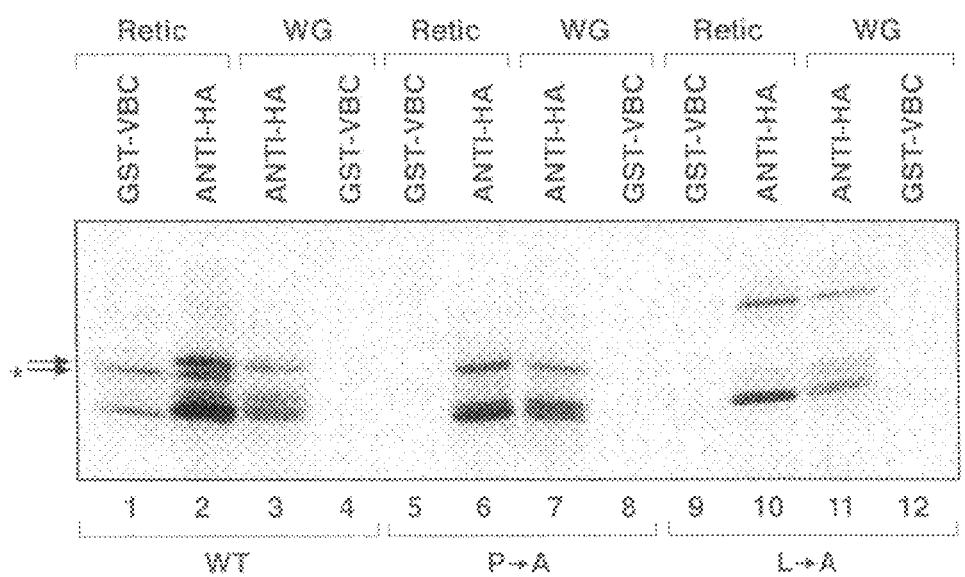

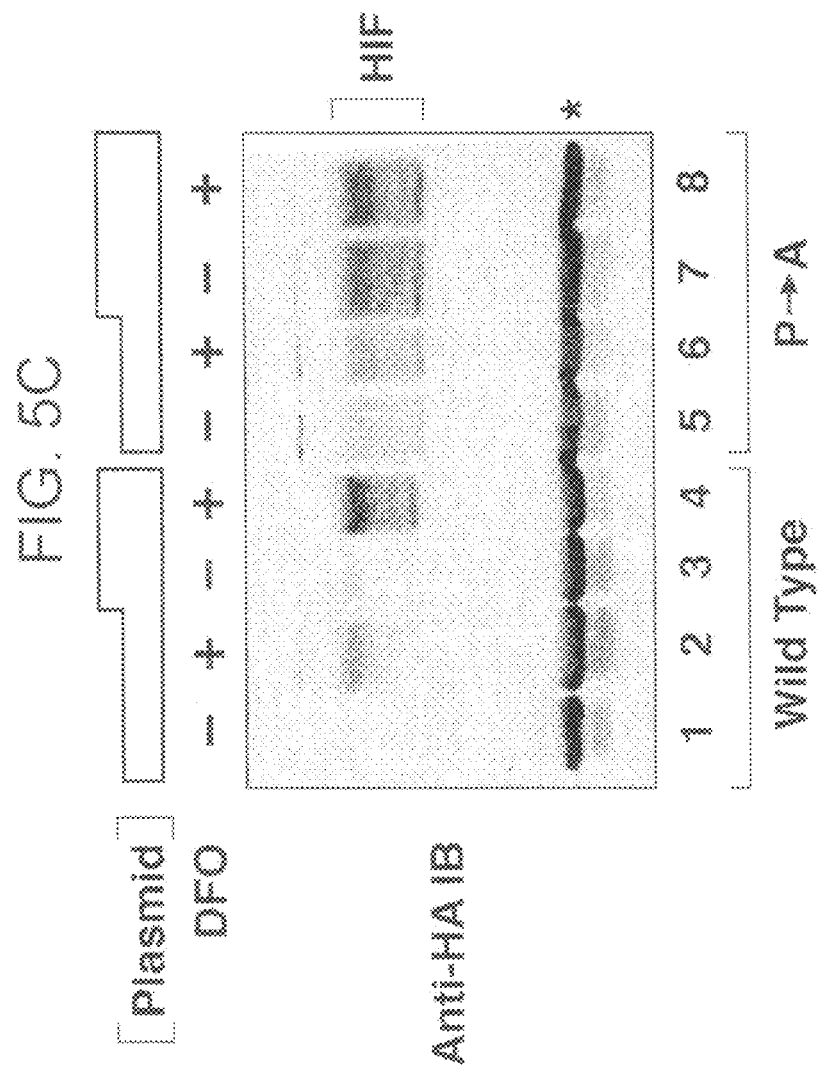

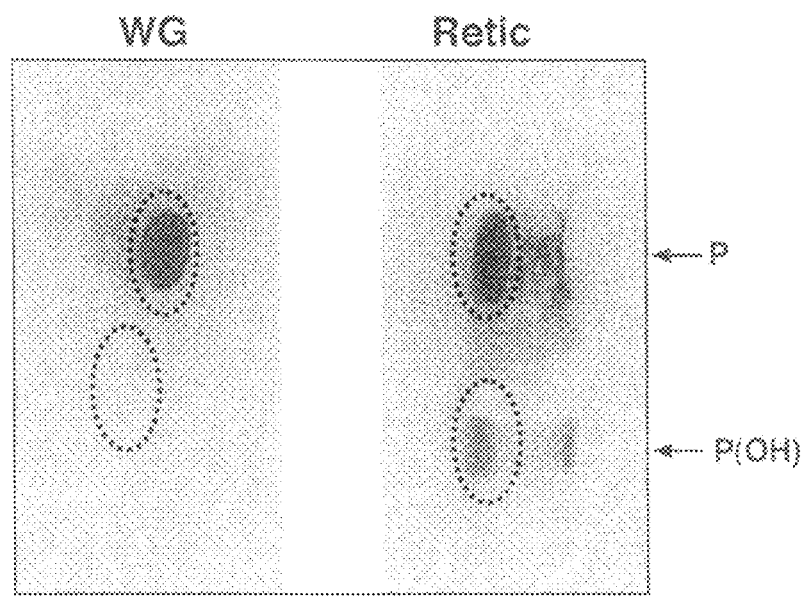

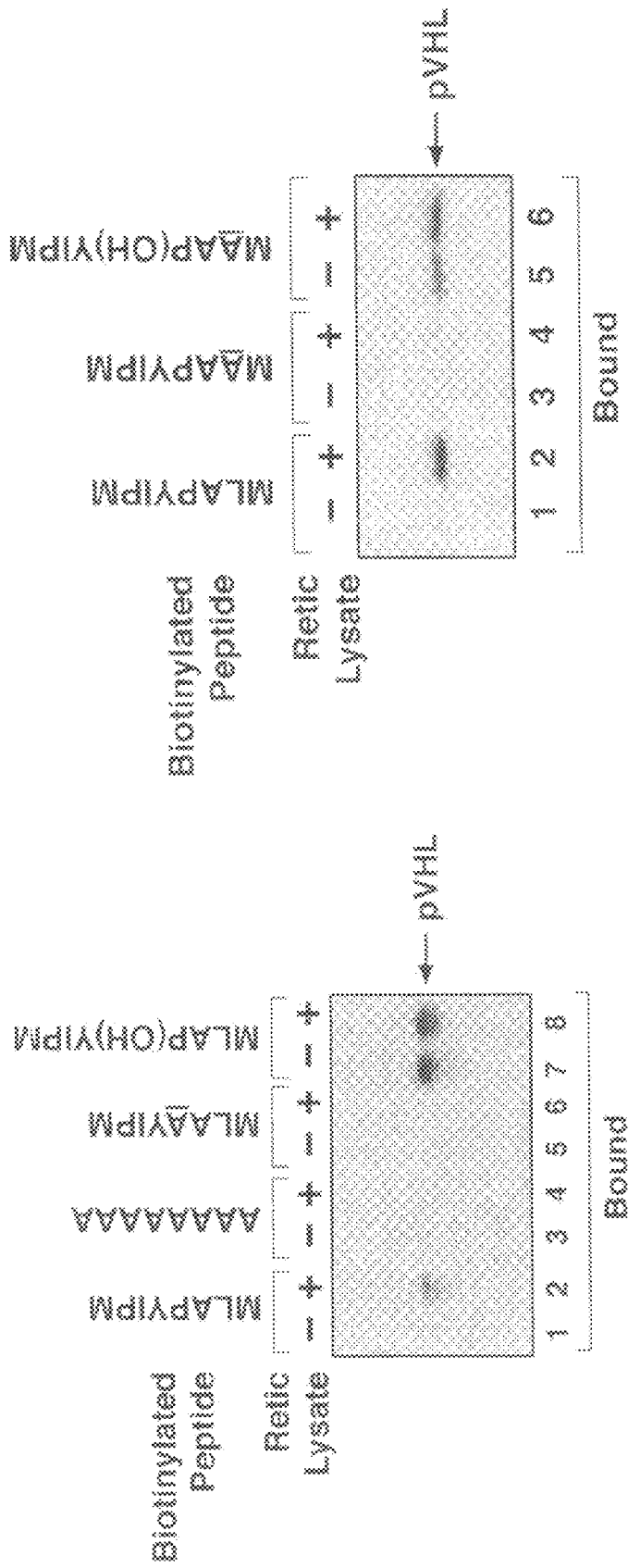

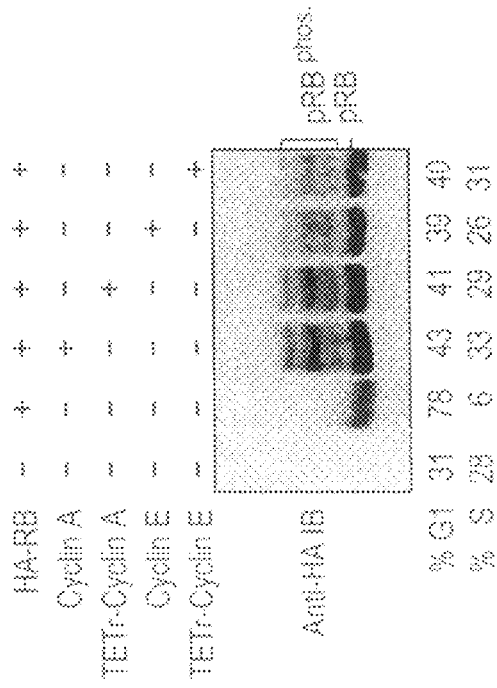
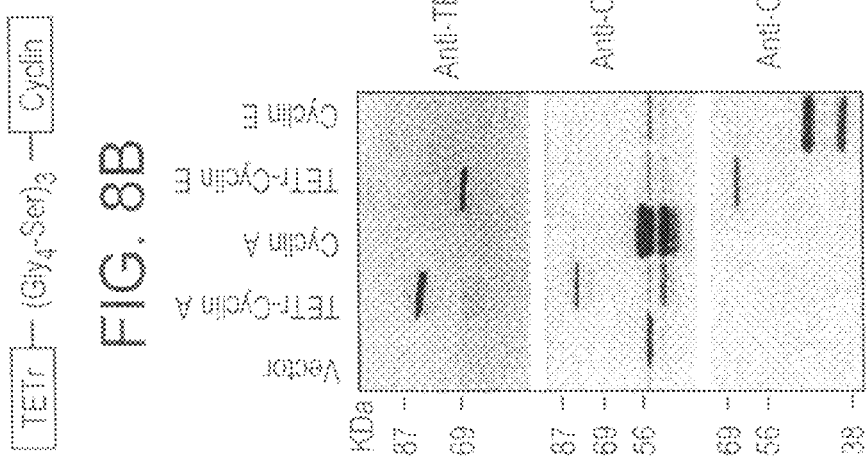

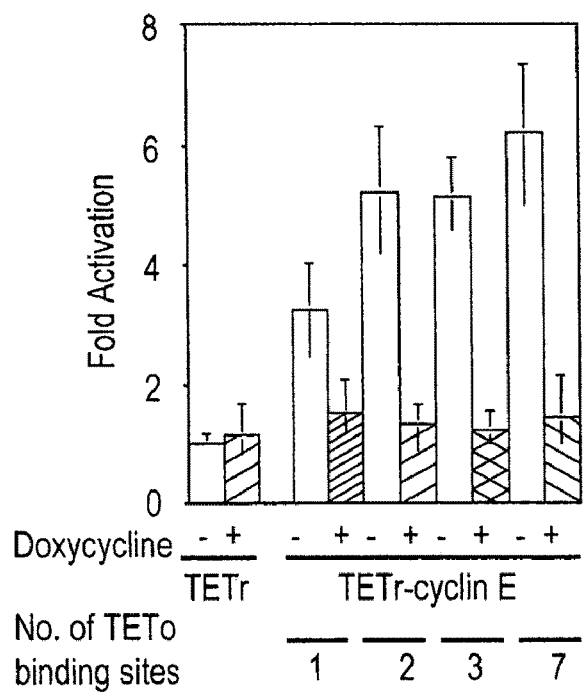

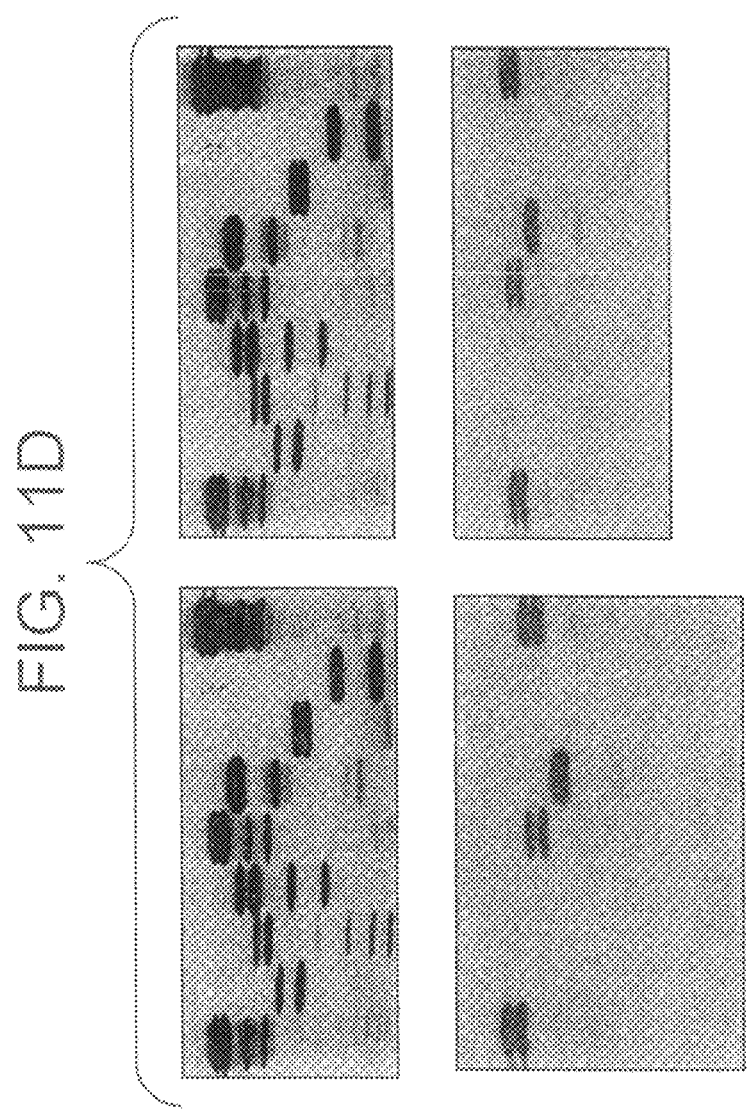

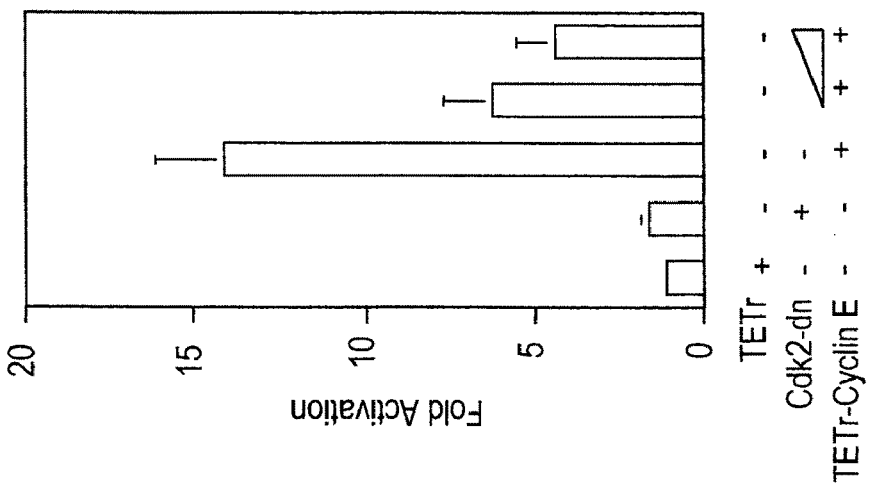
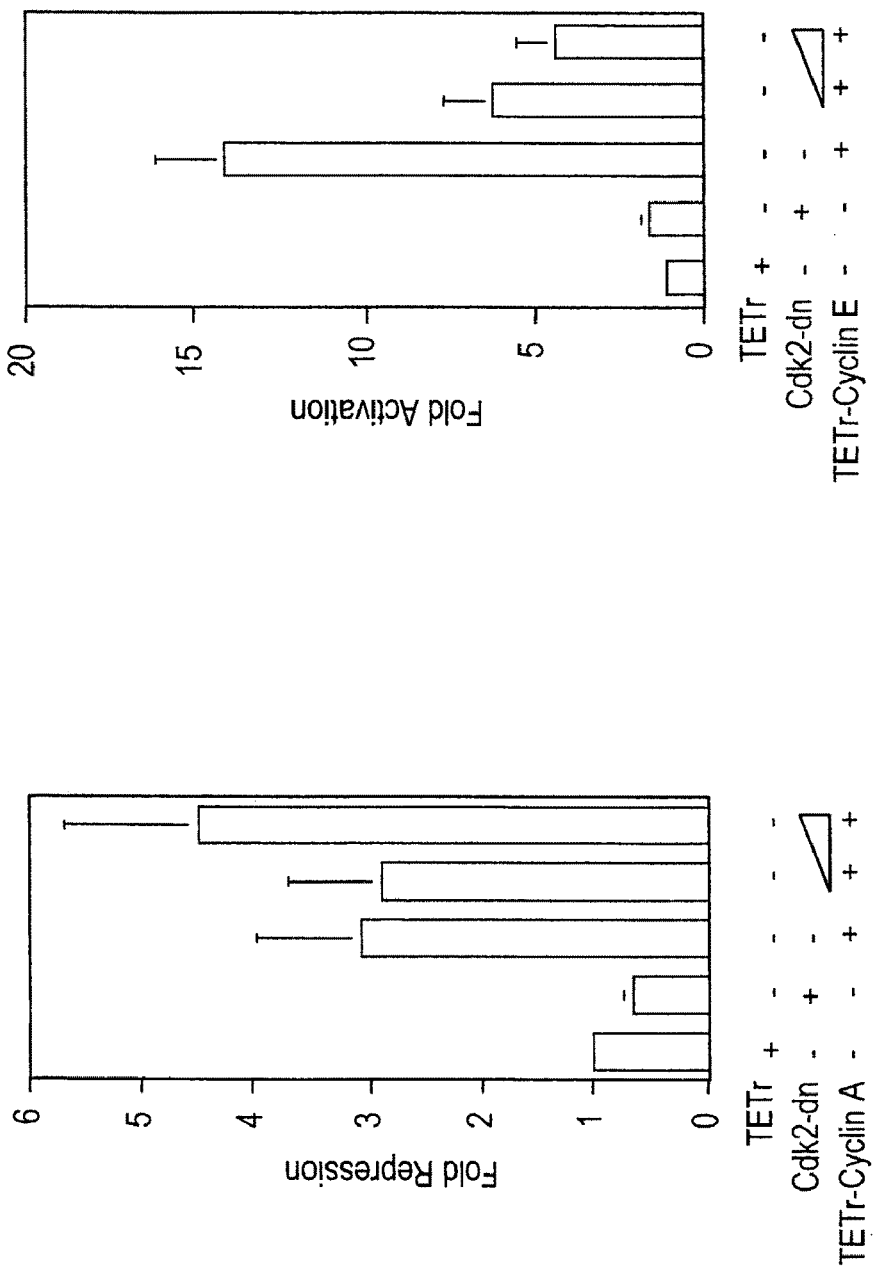
FIG. 13B
FIG. 13A

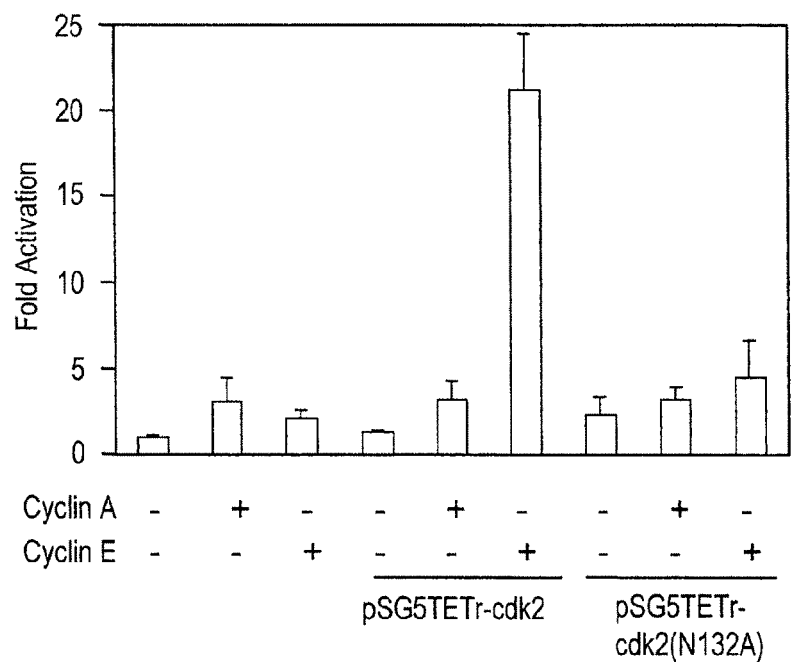

0 (hrs)

%G0-G1 79.37
%S 7.16

6 (hrs)

%G0-G1 76.28
%S 10.09

12 (hrs)

%G0-G1 68.66
%S 17.48

18 (hrs)

%G0-G1 67.73
%S 19.56

24 (hrs)
%G0-G1 10.47
%S 69.78

30 (hrs)
%G0-G1 25.93
%S 24.16

36 (hrs)
%G0-G1 39.57
%S 21.67

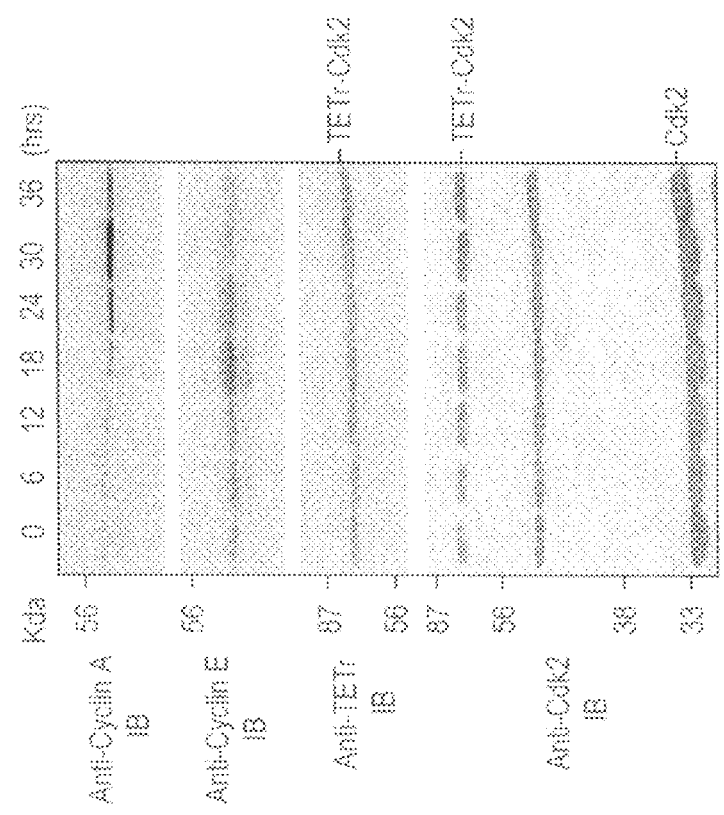

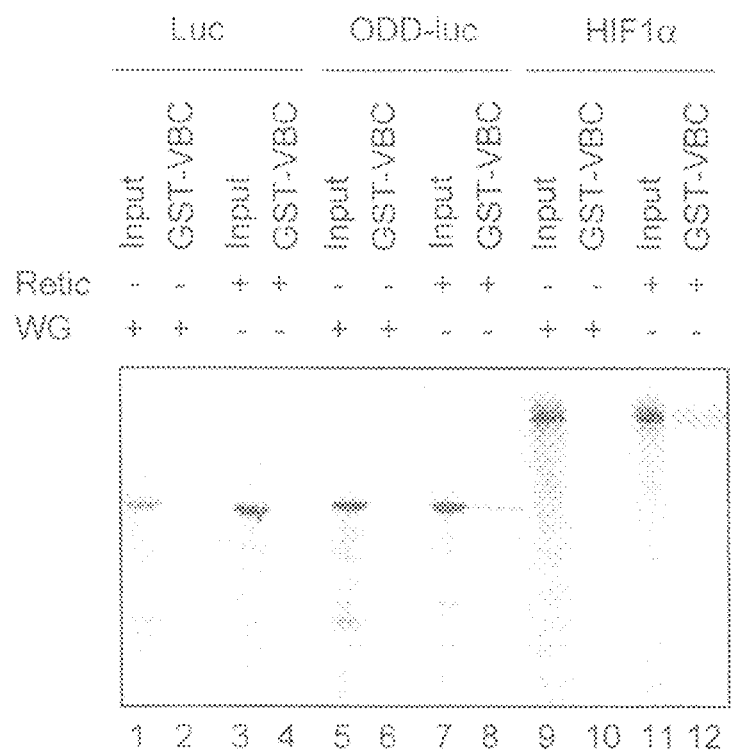

```
MEGAGGANDKKKISSERRKEKSRDAARSRRSKESEVFYELAH
QLPLPHNVSSHLDKASVMRLTISYLRVRKLLDAGDLDIEDDM
KAQMNCFYLKALDGFVMVLTDDGDMIYISDNVNKYMGLTQFE
LTGHSVFDFTHPCDHEEMREMLTHRNGLVKKGKEQNTQRSFF
LRMKCTLTSRGRTMNIKSATWKVLHCTGHIHVYDTNSNQPQC
GYKKPPMTCLVLICEPIPHPSNIEIPLDSKTFLSRHSLDMKF
SYCDERITELMGYEPEELLGRSIYEYYHALDSDHLTKTHHDM
FTKGQVTTGQYRMLAKRGGYVWVETQATVIYNTKNSQPQCIV
CVNYVVSGIIQHDLIFSLQQTECVLKPVESSDMKMTQLFTKV
ESEDTSSLFDKLKKEPDALTLLAPAAGDTIISLDFGSNDTET
DDQQLEEVPLYNDVMLPSPNEKLQNINLAMSPLPTAETPKPL
RSSADPALNQEVALKLEPNPESLELSFTMPQIQDQTPSPSDG
STRQSSPEPNSPSEYCFYVDSDMVNEFKLELVEKLFAEDTEA
KNPFSTQDTDLDLEMLAPYIPMDDDFQLRSFDQLSPLESSSA
SPESASPQSTVTVFQQTQIQEPTANATTTTATTDELKTVTKD
RMEDIKILIASPSPTHIHKETTSATSSPYRDTQSRTASPNRA
GKGVIEQTEKSHPRSPNVLSVALSQRTTVPEEELNPKILALQ
NAQRKRKMEHDGSLFQAVGIGTLLQQPDDHAATTSLSWKRVK
GCKSSEQNGMEQKTIILIPSDLACRLLGQSMDESGLPQLTSY
DCEVNAPIQGSRNLLQGEELLRALDQVN
```

FIG. 19

D=DNA-Binding Domain e.g. TETr

E=Enzyme or Enzyme Partner e.g. Cdk2

R=Reporter cDNA e.g. Luciferase

▨ =Binding Site for 'D' e.g. TETo

⌐ =Promoter

HIFαPROLYL HYDROXYLATION ASSAY

RELATED APPLICATIONS

This application is a continuation of U.S. application Ser. No. 11/027,273, filed on Dec. 30, 2004, now abandoned, which is a continuation of U.S. application Ser. No. 10/859,935, filed Jun. 2, 2004, now abandoned, which is a continuation of U.S. application Ser. No. 10/101,812, filed Mar. 19, 2002, now U.S. Pat. No. 6,855,510, which claims priority to U.S. Application Nos. 60/277,425, filed Mar. 20, 2001; 60/277,431, filed Mar. 20, 2001; 60/277,440, filed Mar. 20, 2001; 60/332,493, filed Nov. 9, 2001; 60/332,334, filed Nov. 9, 2001; 60/345,200, filed Nov. 9, 2001; 60/345,131 filed Dec. 20, 2001; 60/342,598, filed Dec. 20, 2001; and 60/345,132, filed Dec. 20, 2001 each of which are incorporated herein by reference in their entireties.

STATEMENT AS TO FEDERALLY SPONSORED RESEARCH

This invention was made with U.S. government support under National Cancer Institute grant CA76120. The government has certain rights in the invention.

BACKGROUND OF THE INVENTION

The invention relates to drug discovery. The invention features the use of light emitting proteins as tools for diagnosis, drug screening and discovery, and as pharmaceuticals for in vivo treatment.

A key advance in the biomedical arts has been the discovery of bioluminescent protein moieties, e.g., green fluorescent protein (GFP) and luciferase, which can be expressed in diverse mammalian cell types and thus act as detectable signals for biological signal transduction pathways and events. An increased understanding of how diverse biological processes are regulated by the actions of cellular enzymes, e.g., kinases, proteases, and ubiquitin ligases, has also been emerging. Alterations in the activity of these enzymes may underlie the initiation and/or progression of diseases such as cancer.

Methods of detecting biological activities and substances using bioluminescent proteins have recently been developed. For example, protein phosphorylation events can be detected using fusion proteins containing GFP (see, e.g., U.S. Pat. No. 5,958,713) or luciferase, aequorin and obelin (see, e.g., U.S. Pat. No. 5,683,888). Light-generating moieties have been introduced into mammals to specifically localize events such as parasite infection (see, e.g., U.S. Pat. No. 5,650,135).

How cells sense changes in ambient oxygen is a central problem in biology. In mammalian cells, lack of oxygen, or hypoxia, leads to the stabilization of a sequence-specific DNA-binding transcription factor called HIF (hypoxia-inducible factor), which transcriptionally activates a variety of genes linked to processes such as angiogenesis and glucose metabolism.

Tissue ischemia is a major cause of morbidity and mortality. Ischemia can result from chronic hypoxia brought on by lack of blood supply to the tissue occurring from, for example, stroke, deep vein thrombosis, pulmonary embolus, and renal failure. Ischemic tissue is also found in tumors.

HIF binds to DNA as a heterodimer consisting of an alpha subunit and a beta subunit (also called aryl hydrocarbon receptor nuclear translocator or ARNT). The alpha subunit is rapidly polyubiquitinated and degraded in the presence of oxygen whereas the beta subunit is constitutively stable. von Hippel-Lindau (VHL) disease is a hereditary cancer syndrome characterized by the development of highly vascular tumors that overproduce hypoxia-inducible mRNAs such as vascular endothelial growth factor (VEGF). The product of the VHL tumor suppressor gene, pVHL, is a component of multiprotein complex that contains elongin B, elongin C, Cul2, and Rbx1. This complex bears structural and functional similarity to SCF (Skp1/Cdc53 or Cullin/F-box) ubiquitin ligases. In the presence of oxygen pVHL binds directly to HIFα subunits and targets them for polyubiquitination and destruction. Cells lacking functional pVHL can not degrade HIF and thus overproduce mRNAs encoded by HIF-target genes.

Progress has also been made in recent years towards understanding the molecular mechanisms in control of cell proliferation. Aberrant cell proliferation is a hallmark event in the onset and progression of diseases such as cancer. Progression through the mammalian cell-cycle is linked to the orchestrated appearance and destruction of cyclins. Different cyclins are associated with different cell-cycle transitions. For example, cyclin E is active in late G1 and early S-phase, cyclin A is active in S-phase, and cyclin B is active in mitosis. Cyclins bind to cyclin-dependent kinases (cdks). In this context, cyclins activate the catalytic activity of their partner cdk(s) and also play roles in substrate recognition.

Some transcriptional regulatory proteins, such as the pRB homologs p107 and p130, the E2F family members E2F1, E2F2, and E2F3, the transcriptional coactivator p300, and NPAT (nuclear protein mapped to the AT locus) form stable complexes with cyclin A/cdk2 and/or cyclin E/cdk2. All of these proteins bind directly or indirectly to DNA. Thus, such complexes might serve as vehicles for increasing the concentration of cyclin A/cdk2 or cyclin E/cdk2 at certain sites within the genome. As such, cyclin A/cdk2 and cyclin E/cdk2 might play relatively direct roles in processes such as transcription and DNA replication. These two processes are fundamental in normal cell proliferation and are perturbed during aberrant cell proliferation, such as in cancer.

SUMMARY OF THE INVENTION

The invention relates in part to the discovery of light-generating fusion proteins (or a cell expressing the light-generating fusion protein), wherein the light-generating fusion protein features a ligand binding site and a light-generating polypeptide moiety. The light-generating fusion protein ("LGP") has a feature where the light generation of the light-generating polypeptide moiety changes upon binding of a ligand at the ligand binding site. The ligand may be active in an environment only under certain conditions, e.g., in a hypoxic state, such that the light-generating fusion protein is "turned" on or off only under such conditions.

The light-generating fusion proteins of the invention may be used for screening for modulators of activity or latency of (or predisposition to) disorders such as hypoxia, cancer, diabetes, heart disease or stroke. For example, a test compound may be administered to a test animal at increased risk for such a disorder, wherein the test animal recombinantly expresses a light-generating fusion protein, allowing for localization of the light-generating fusion protein, detecting the luminescence of the light-generating polypeptide moiety in the test animal after administering the test compound, and comparing the luminescence of the light-generating polypeptide moiety in the test animal with the luminescence of the light-generating polypeptide moiety in a control animal not administered the test compound. A change in the activity of the light-generating polypeptide moiety in the test animal relative to the control animal indicates the test compound may be a modulator of, e.g., prolyl hydroxylase.

The effects of an anti-hypoxic compound in vivo may be determined in another embodiment, by administering to a subject, e.g., mammalian, a light-generating fusion protein comprising an ubiquitin ligase binding site and a light-generating polypeptide moiety or a cell expressing the light-generating fusion protein, allowing for localization of the light-generating fusion protein or cell in hypoxic tissue in the subject; and measuring the luminescence of the localized light-generating fusion protein from the hypoxic tissue.

Methods in accordance with the invention are also provided for determining the effects of an anti-cell proliferation compound under study in a mammalian subject, by administering to a test subject a light-generating fusion protein containing a cyclin/cdk binding site or a cell expressing the light-generating fusion protein of the invention, allowing for localization of the fusion protein or cell, measuring luminescence from the localized light-generating fusion protein; and imaging the localized light-generating fusion protein, thereby determining the effects of the anti-cell proliferation compound.

Cyclin/cdk activity may be assayed in another embodiment of the invention wherein a test sample is contacted with a light-generating fusion protein comprising a cyclin/cdk binding site and a light-generating polypeptide moiety; and thereafter the presence or amount of cyclin/cdk activity in said test sample is determined by measuring the luminescence of the test sample.

The invention yet further relates to DNA constructs, including an isolated DNA encoding a modified LGP wherein one or more amino acids have been substituted, inserted or deleted to provide a ligand binding site such as a ubiquitin ligase or protease recognition site, wherein fluorescence of the LGP changes upon binding of a ligand to the ligand binding site.

The invention also relates to light-generating fusion proteins having a ligand binding site, such as a ubiquitin ligase binding site, or a HIF1α polypeptide moiety; and a light-generating polypeptide moiety. Another embodiment features a light-generating fusion protein with a cyclin/cdk binding site, a suicide protein polypeptide moiety, and a light-generating polypeptide moiety; and a light-generating fusion protein comprising a protein dimerization domain and a light-generating protein moiety. In a preferred embodiment, the light-generating fusion proteins have the property that upon ligand binding to the ligand binding site, the luminescence of the light-generating polypeptide moiety is changed without altering the phosphorylational state of the fusion protein.

The invention further relates to fusion proteins including a HIF1α polypeptide moiety or cyclin/cdk binding site, and a suicide protein polypeptide moiety. A light-generating polypeptide moiety may optionally be included. These protein constructs may be used to selectively target certain cells, e.g., hypoxic tumor cells, for destruction. For example, the invention includes methods of treating hypoxic or ischemic disorders by administering to a subject an effective amount of a fusion protein comprising a HIFα polypeptide moiety having a binding affinity for prolyl hydroxylase, and a suicide polypeptide moiety, such that the hypoxic or ischemic disorder is treated. Methods of killing hypoxic tumor cells, wherein an effective amount of the fusion/suicide protein is administered to a subject, such that the hypoxic tumor cells are killed; and methods of treating cell-proliferating disorders by administering to a subject an effective amount of a fusion protein comprising a cyclin/cdk binding site and a suicide protein polypeptide moiety, such that the cell-proliferating disorder is treated, are also contemplated.

The treatment of cell-proliferating disorders may be monitored by an embodiment of the invention, e.g., by administering to a subject an effective amount of a fusion protein comprising a HIFα polypeptide moiety having a binding affinity for prolyl hydroxylase, a suicide polypeptide moiety, and a light-generating polypeptide moiety, wherein the light generation of the light-generating fusion protein changes upon binding of prolyl hydroxylase to the HIFα polypeptide moiety, such that the cell-proliferating disorder is treated, and monitoring the ability of the fusion protein to inhibit cell proliferation by measuring the light generated by the light-generating fusion protein. Alternately, treatment of cell-proliferating disorders may be monitored by administering to a subject an effective amount of a light-generating fusion protein comprising a cyclin/cdk binding site, a suicide protein polypeptide moiety, and a light-generating polypeptide moiety, wherein the light generation of the light-generating fusion protein changes upon binding of a cyclin to the cyclin/cdk binding site, such that said cell-proliferating disorder is treated; and monitoring the ability of the fusion protein to inhibit cell proliferation by measuring the light generated by the light-generating fusion protein.

Other embodiments of the invention include a cyclin/cdk binding site and a light-generating polypeptide moiety; and a protease binding site and a light-generating protein moiety. Antibodies specific for a protein complex comprising HIF1α and pVHL are also detailed as within the present invention.

BRIEF DESCRIPTION OF THE DRAWING

FIG. 8 illustrates the production of TETr-cyclins A and E.

FIG. 13 shows that transcriptional activation by DNA bound cyclin E depends on cdk2 catalytic activity.

FIGS. 15-18 illustrate the results obtained in Example 2.

FIG. 19 illustrates the wild type sequence of HIF1α, Accession No. Q16665 (SEQ ID NO: 1X).

DETAILED DESCRIPTION OF THE INVENTION

Definitions

Figure 1A:
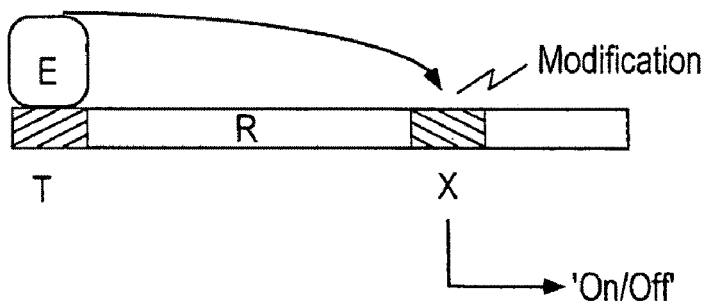
FIG. 1 is a schematic representation of different fusion proteins of the present invention.

"Light-generating" or "luminescent" includes the property of generating light through a chemical reaction or through the absorption of radiation, including phosphorescence, fluorescence, and bioluminescence.

"Light" includes electromagnetic radiation having a wavelength of between about 300 nm and about 1100 nm n.

"Non-invasive" methods for detecting localization in a subject does not include largely invasive methods such as conventional surgery or biopsy.

"Light-generating fusion protein" includes proteins of the invention having a light-generating or luminescent portion, i.e., a light-generating polypeptide moiety and a ligand binding site. In general, when a ligand of interest binds to the ligand binding site of the light-generating fusion protein, the light-generating properties of the light-generating polypeptide moiety change, either going from "dark" to "light", or vice versa.

"Light-generating polypeptide moiety" includes any protein known to those of ordinary skill in the art to provide a readily detectable source of light when present in stable form. Non-limiting examples include light-generating proteins described in U.S. Pat. Nos. 5,683,888, 5,958,713, and 5,650,135, e.g., ferredoxin IV, green fluorescent protein, red fluorescent protein, yellow fluorescent protein, blue fluorescent protein, the luciferase family and the aequorin family. In a preferred embodiment, the light-generating polypeptide moiety is a protein such as green fluorescent protein, red fluorescent protein, yellow fluorescent protein and blue fluorescent protein.

"Colinear effector site" includes regions of the light-generating polypeptide moiety that, when acted on by events subsequent to ligand binding, cause the light-generating polypeptide moiety to change its present light-emitting state (i.e., on or off). These regions making up the colinear effector site may do this by, e.g., conformational distortion, chemical modification, e.g., ubiquitination of a residue or residues in the colinear effector site, or by cleavage of a portion of all or part of the colinear effector site.

"Having binding character for prolyl hydroxylase" refers to a property making HIFα polypeptide moieties suitable for, e.g., screening methods of the invention and includes HIF polypeptide sequences suitable or adapted for prolyl hydroxylase binding as well as native or wild-type HIF sequences to which pVHL has recognized and bound.

"Having binding character for ubiquitin ligase" refers to a property making HIFα polypeptide moieties suitable for, e.g., screening methods of the invention, e.g., including native HIF polypeptide sequences having hydroxylated proline residues hydroxylated by prolyl hydroxylase, or, e.g., "HIF1α polypeptide moieties" as defined herein.

"Localization" includes determining the particular region of the subject of an entity of interest, e.g., a tumor.

"Kemptide" includes a synthetic cAMP peptide substrate corresponding to part of the phosphyorylation site sequence in porcine liver pyruvate kinase. "Malantide" includes cAMP-dependent protein kinase and protein kinase C substrate in various tissues.

"Small molecule" includes compositions that have a molecular weight of less than about 5 kD and most preferably less than about 4 kD. Small molecules can be, e.g., nucleic acids, peptides, polypeptides, peptidomimetics, carbohydrates, lipids or other organic or inorganic molecules.

"Spread of infection" includes the spreading and colonization by a pathogen of host sites other than the initial infection site. The term can also include, however, growth in size and/or number of the pathogen at the initial infection site.

"Ligand" includes a molecule, a small molecule, a biomolecule, a drug, a peptide, a polypeptide, a protein, a protein complex, an antibody, a nucleic acid, or a cell.

"Ligand binding site" includes the location on the light-generating fusion protein to which a ligand binds, whereupon the light-generating polypeptide moiety is activated or inactivated as a direct or indirect consequence of ligand binding. Binding to the ligand binding site may be direct or indirect, e.g., via protein dimerization in conjunction with other proteins, as described hereinbelow.

"Targeting moiety" includes moieties which allow the light-generating fusion protein of the invention to be selectively delivered to a target organ or organs. For example, if delivery of a therapeutic compound to the brain is desired, the carrier molecule may include a moiety capable of targeting the compound to the brain, by either active or passive transport. Illustratively, the carrier molecule may include a redox moiety, as described in, for example, U.S. Pat. Nos. 4,540,564 and 5,389,623, both to Bodor. These patents disclose drugs linked to dihydropyridine moieties which can enter the brain, where they are oxidized to a charged pyridinium species which is trapped in the brain. Thus, compound accumulates in the brain. Many targeting moieties are known, and include, for example, asialoglycoproteins (see, e.g. Wu, U.S. Pat. No. 5,166,320) and other ligands which are transported into cells via receptor-mediated endocytosis. Targeting moieties may be covalently or non-covalently bound to a light-generating fusion protein. The targeting moiety may also be attached to a vector.

"Bioluminescent" molecules or moieties include luminescent substances which utilize chemical energy to produce light.

"Fluorescent" molecules or moieties include those which are luminescent via a single electronically excited state, which is of very short duration after removal of the source of radiation. The wavelength of the emitted fluorescence light is longer than that of the exciting illumination (Stokes' Law), because part of the exciting light is converted into heat by the fluorescent molecule.

"Entities" include, without limitation, small molecules such as cyclic organic molecules; macromolecules such as proteins; polymers; proteins; polysaccharides; nucleic acids; particles, inert materials; organelles; microorganisms such as viruses, bacteria, yeast and fungi; cells, e.g., eukaryotic cells; embryos; prions; tumors; all types of pathogens and pathogenic substances; and particles such as beads and liposomes. In another aspect, entities may be all or some of the cells that constitute the mammalian subject being imaged, e.g., diseased or damaged tissue, or compounds or molecules produced by those cells, or by a condition under study. Entities for which the invention has particular utility include tumors, proliferating cells, pathogens, and cellular environments comprising hypoxic tissue.

"Infectious agents" include parasites, viruses, fungi, bacteria or prions.

"Promoter induction event" includes an event that results in the direct or indirect induction of a selected inducible promoter.

"Heterologous-gene" includes a gene which has been transfected into a host organism. Typically, a heterologous gene refers to a gene that is not originally derived from the transfected or transformed cells' genomic DNA.

"Opaque medium" includes a medium that is "traditionally" opaque, not necessarily absolutely opaque. Accordingly, an opaque medium includes a medium that is commonly considered to be neither transparent nor translucent, and includes items such as a wood board, and flesh and skin of a mammal.

"HIFα polypeptide moiety" includes all or part of the amino acid sequence of HIF1α, HIF2α, or HIF3α.

"HIF1αpolypeptide moiety" includes all or part of the amino acid sequence of HIF1α, e.g., SEQ ID NO: 1X, the amino acid sequence corresponding to the N-terminal residues 1-600 of HIF1α, numbered in accordance with wild-type HIF1α, wherein either or both of residues 402 and 564 are proline or hydroxylated proline, or an 80 to 120, 20 to 30, 12 to 14, or 4 to 12 amino acid sequence corresponding to the residues adjacent to and/or surrounding residue 402 and/or 564, inclusive, of HIF1α, wherein residues 402 and/or 564 is proline or hydroxylated proline.

The invention relates in part to methods and compositions relating to detecting, localizing and quantifying enzyme activities and protein-protein interactions in vivo, in vitro and in silico using light-emitting fusion proteins. The fusion proteins contain domains capable of binding by enzymes and other ligands, and of being modified as a consequence of this binding. The light generating domains include, without limitation, regions from fluorescent proteins and bioluminescent proteins. Light emission is detected by known methods, such as detection with suitable instrumentation (such as a CCD camera) in vivo, in vitro or in silico, such as in a living cell or intact organism, a cell culture system, a tissue section, or an array.

Light-generating fusion proteins of the invention are capable of taking part in a luminescent reaction whereby different biological, biochemical, chemical and physical events are measured. The light-generating fusion protein is capable of being modified such that it does or does not emit light or cause light to be emitted. Light-generating fusion proteins include a ligand binding site and a light-generating polypeptide moiety, wherein the bioluminescence of the polypeptide moiety changes upon binding of a ligand at the ligand binding site.

Without wishing to be bound by interpretation, the ligand binding site acts as in a sense as a "switch" for the light-generating polypeptide moiety, i.e., when the ligand binds to the ligand binding site, the light-generating polypeptide moiety emits light, or alternately, ceases to do so upon ligand binding. The "switching" on or off, in embodiment, may be done by means of a "colinear effector site" which includes regions of the light-generating polypeptide moiety that, when acted on by events subsequent to ligand binding, cause the light-generating polypeptide moiety to change its present light-emitting state (i.e., on or off). The regions making up the colinear effector site may do this by, e.g., conformational distortion, chemical modification, e.g., ubiquitination of a residue or residues in the colinear effector site, or by cleavage of a portion of all or part of the colinear effector site.

The invention further provides methods for testing putative inhibitor compounds for activity ("screening") in promoting HIF stabilization, e.g., contacting the compound, ischemic tissue, and the fusion protein of the invention under conditions appropriate to detect the fusion protein if the compound promotes HIF stabilization. The method (also referred to herein as a "screening assay") can be used for identifying modulators, i.e., candidate or test compounds or agents (e.g., peptides, peptidomimetics, small molecules or other drugs) that promote HIF stabilization. The invention also includes compounds identified in the screening assays described herein, and pharmaceutical compositions for treatments as described herein.

Other screening methods are also part of the invention. For example, modulators of activity or latency of, or predisposition to disorders may be identified by administering a test compound to a test animal at increased risk for a disorder (e.g., cancer, diabetes, heart disease, stroke, or a hypoxia-related disorder), wherein the test animal recombinantly expresses a light-generating fusion protein comprising a ligand binding site and a light-generating polypeptide moiety, wherein the light generation of the light-generating fusion protein changes upon binding of a ligand at the ligand binding site, and the ligand binding site recognizes a ligand on an entity associated with a disorder, or a product of the disorder; allowing for localization of the light-generating fusion protein and an entity, wherein contact between the ligand binding site and a ligand associated with the disorder causes a modification of a colinear effector site which alters the light generation of the light-generating polypeptide moiety; detecting the luminescence of the light-generating polypeptide moiety in the test animal after administering the compound; and comparing the luminescence of the light-generating polypeptide moiety in the test animal with the luminescence of the light-generating polypeptide moiety in a control animal, wherein a change in the activity of the light-generating polypeptide moiety in the test animal relative to the control indicates the test compound is a modulator of latency of or predisposition to, the disorder in question.

The invention advantageously may be used to non-invasively determine the effects of an anti-hypoxic compound in vivo. A light-generating fusion protein of the invention, or a cell expressing same, comprising an ubiquitin ligase binding site and a light-generating polypeptide moiety, wherein the light generation of the light-generating fusion protein changes upon binding of a ubiquitin ligase at the ubiquitin ligase binding site, the ubiquitin ligase binding site recognizing a ubiquitin ligase present in hypoxic conditions in hypoxic tissue is administered to a subject. Localization of the light-generating fusion protein or cell in hypoxic tissue in the subject (wherein contact between the ubiquitin ligase binding site and a ubiquitin ligase causes a modification of a colinear effector site which alters the light generation of the light-generating polypeptide moiety) is allowed to occur, and the ability of the candidate compound to inhibit hypoxia is determined, by measuring the luminescence of the localized light-generating fusion protein.

The invention further relates to methods of identifying or detecting prolyl hydroxylation, wherein the substrate peptide (or polypeptide) is contacted with pVHL, wherein the amount of pVHL bound reflects the degree of hydroxylation. In one embodiment, the peptide corresponds to HIF1α 555-575. The HIF peptide can be immobilized (for example, on a nitrocellulose filter or at the bottom of a 96 well plate) or free in solution. Binding to pVHL can be monitored using a variety of standard methods familiar to those skilled in the art.

In another embodiment, the invention relates to methods of identifying or detecting prolyl hydroxylation, wherein the substrate peptide or polypeptide is contacted with an antibody, wherein the amount of antibody bound reflects the degree of hydroxylation. In one embodiment, the peptide corresponds to HIF1α 555-575. The HIF peptide may be immobilized (for example, on a nitrocellulose filter or at the bottom of a 96 well plate) or free in solution. Binding to the antibody can be monitored using a variety of standard methods familiar to those skilled in the art.

Yet another embodiment of the invention relates to methods of identifying or detecting prolyl hydroxylation wherein a polypeptide is translated in the presence of labeled, e.g., radioactive, proline and a prolyl hydroxylase, hydrolyzing the resulting labeled polypeptide, and detecting labeled hydroxyproline incorporation by analytical means, such as thin layer chromatography.

A further embodiment of the invention relates to methods of identifying or detecting prolyl hydroxylation wherein the substrate peptide (or polypeptide) is contacted with a source of prolyl hydroxylase in the presence or absence of putative inhibitors, and the degree of prolyl hydroxylation is monitored as described in any one of the above three paragraphs. In one embodiment, the peptide corresponds to HIF1α 555-575, and the prolyl hydroxylase consists of a mammalian cell extract. In another embodiment, the peptide corresponds to HIF1α 555-575 and the prolyl hydroxylase consists of purified or partially purified Egl9. Further, particularly useful embodiments relate to small molecule inhibitors of prolyl hydroxylation such as identified using this method, and use of the inhibitors to treat diseases characterized by ischemia.

The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

Libraries of chemical and/or biological mixtures, such as fungal, bacterial, or algal extracts, are known in the art and can be screened with any of the assays of the invention. Examples of methods for the synthesis of molecular libraries can be found in the art, for example in: DeWitt, et al., 1993. *Proc. Natl. Acad. Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412-421), or on beads (Lam, 1991. *Nature* 354: 82-84), on chips (Fodor, 1993. *Nature* 364: 555-556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865-1869) or on phage (Scott and Smith, 1990. *Science* 249: 386-390; Devlin, 1990. *Science* 249: 404-406; Cwirla, et al., 1990. *Proc. Natl. Acad. Sci. U.S.A.* 87: 6378-6382; Felici, 1991. *J. Mol. Biol.* 222: 301-310; Ladner, U.S. Pat. No. 5,233,409).

Modulation of prolyl hydroxylase has a variety of uses. Inhibiting prolyl hydroxylase may facilitate cell cycle progression and the production of a number of proteins which promote angiogenesis and/or promote cellular survival or cellular function in hypoxia, a desirable outcome in the treatment of certain clinical conditions, particularly ischemic conditions such as coronary, cerebral and vascular insufficiency.

VHL used in assays of the invention may be any suitable mammalian VHL, particularly human VHL. Human VHL has been cloned and sources of the gene can be readily identified by those of ordinary skill in the art. Its sequence is available as Genbank accession numbers AF010238 and L15409. Other mammalian VHLs are also available, such as murine VHL (accession number U12570) and rat (accession numbers U14746 and S80345). Non-mammalian homologues include the VHL-like protein of *C. elegans*, accession number F08G12. VHL gene sequences may also be obtained by routine cloning techniques, for example by using all or part of the human VHL gene sequence as a probe to recover and to determine the sequence of the VHL gene in other species. A wide variety of techniques are available for this, for example, PCR amplification and cloning of the gene using a suitable source of mRNA (e.g., from an embryo or a liver cell), obtaining a cDNA library from a mammalian, vertebrate, invertebrate or fungal source, e.g., a cDNA library from one of the above-mentioned sources, probing the library with a polynucleotide of the invention under stringent conditions, and recovering a cDNA encoding all or part of the VHL protein of that mammal. Suitable stringent conditions include hybridization on a solid support (filter) overnight incubation at 420° C. in a solution containing 50% formamide, 5×SSC (750 mM NaCl, 75 mM sodium citrate), 50 mM sodium phosphate (pH 7.6), 5×Denhardt's solution, 10% dextran sulfate and 20 µg/ml salmon sperm DNA, followed by washing in 0.03M sodium chloride and 0.03M sodium citrate (i.e. 0.2×SSC) at from about 50° C. to about 60° C.). Where a partial cDNA is obtained, the full length coding sequence may be determined by primer extension techniques.

It is not necessary to use the entire VHL protein (including their mutants and other variants). Fragments of the VHL may be used, provided such fragments retain the ability to interact with the target domain of the HIFα subunit. Fragments of VHL may be generated in any suitable way known to those of skill in the art. Suitable ways include, but are not limited to, recombinant expression of a fragment of the DNA encoding the VHL. Such fragments may be generated by taking DNA encoding the VHL, identifying suitable restriction enzyme recognition sites either side of the portion to be expressed, and cutting out that portion from the DNA. The portion may then be operably linked to a suitable promoter in a standard commercially available expression system. Another recombinant approach is to amplify the relevant portion of the DNA with suitable PCR primers. Small fragments of the VHL (up to about 20 or 30 amino acids) may also be generated using peptide synthesis methods which are well known in the art. Generally fragments will be at least 40, preferably at least 50, 60, 70, 80 or 100 amino acids in size.

The HIFα subunit protein may be any human or other mammalian protein, or fragment thereof which has the ability to bind to a wild type full length VHL protein, such that the binding is able, in a normoxic cellular environment, to target the a subunit for destruction.

A number of HIFα subunit proteins have been cloned. These include HIF1α, the sequence of which is available as Genbank accession number U22431, HIF2α, available as Genbank accession number U81984 and HIF3α, available as Genbank accession numbers AC007193 and AC079154. These are all human HIFα subunit proteins. HIFα subunit proteins from other species, including murine HIF1α (accession numbers AF003695, US9496 and X95580), rat HIF1α (accession number Y09507), murine HIF2α (accession numbers U81983 and D89787) and murine HIF3α (accession number AF060194). Other mammalian, vertebrate, invertebrate or fungal homologues may be obtained by techniques similar to those described above for obtaining VHL homologues.

Variants of the HIFα subunits may be used, such as synthetic variants which have at least 45% amino acid identity to a naturally occurring HIFα subunit (particularly a human HIFα subunit), preferably at least 50%, 60%, 70%, 80%, 90%, 95% or 98% identity.

Fragments of the HIFα subunit protein and its variants may be used, provided that the fragments retain the ability to interact with a wild-type VHL, preferably wild-type human VHL. Such fragments are desirably at least 20, preferably at least 40, 50, 75, 100, 200, 250 or 400 amino acids in size. Alternately, such fragments may be 12 to 14 amino acids in size, or as small as four amino acids. Most desirably such fragments include the region 555-575 found in human HIF1α or its equivalent regions in other HIFα subunit proteins. Optionally the fragments also include one or more domains of the protein responsible for transactivation. Reference herein to a HIFα subunit protein includes the above mentioned mutants and fragments which are functionally able to bind VHL protein unless the context is explicitly to the contrary.

The percentage homology (also referred to as identity) of DNA and amino acid sequences can be calculated using commercially available algorithms. The following programs (provided by the National Center for Biotechnology Information) may be used to determine homologies: BLAST, gapped BLAST and PSI-BLAST, which may be used with default parameters. The algorithm GAP (Genetics Computer Group, Madison, Wis.) uses the Needleman and Wunsch algorithm to align two complete sequences that maximizes the number of matches and minimizes the number of gaps. Generally, the default parameters are used, with a gap creation penalty=12 and gap extension penalty=4. Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions.

The precise format of the screening assays may be varied using routine skill and knowledge. The amount of VHL, HIFα subunit and, where required, further components, may be varied depending upon the scale of the assay. In general, the person of skill in the art will select relatively equimolar amounts of the two components, say from 1:10 to 100:1, preferably from 1:1 to 10:1. molar ratio of VHL to HIFα subunit. However there may be particular assay formats which can be practiced outside this range.

Where assays of the invention are performed within cells, the cells may be treated to provide or enhance a normoxic environment. By "normoxic" it is meant levels of oxygen similar to those found in normal air, e.g. about 21% $O_2$ and 5% $CO_2$, the balance being nitrogen. Of course, these exact proportions do not have to be used, and may be varied independently of each other. Generally a range of from 10-30% oxygen, 1-10% $CO_2$ and a balance of nitrogen or other relatively inert and non-toxic gas may be used. Normoxia may be induced or enhanced in cells, for example by culturing the cells in the presence of hydrogen peroxide as described above.

Alternatively, or by way of controls, cells may also be cultured under hypoxic conditions. By "hypoxic" it is meant an environment with reduced levels of oxygen. Most preferably oxygen levels in cell culture will be 0.1 to 1.0% for the provision of a hypoxic state. Hypoxia may be induced in cells simply by culturing the cells in the presence of lowered oxygen levels. The cells may also be treated with compounds which mimic hypoxia and cause up regulation of HIFα subunit expression. Such compounds include iron chelators, cobalt (II), nickel (II) or manganese (II), all of which may be used at a concentration of 20 to 500 μM. such as 100 μM. Iron chelators include desferrioxamine, O-phenanthroline or hydroxypyridinones (e.g. 1,2-diethyl hydroxypyridinone (CP94) or 1,2-dimethyl hydroxypyridinone (CP20)).

Cells in which assays of the invention may be preformed include eukaryotic cells, such as yeast, insect, mammalian, primate and human cells. Mammalian cells may be primary cells or transformed cells, including tumor cell lines. The cells may be modified to express or not to express other proteins which are known to interact with HIF (x subunit proteins and VHL protein, for example Elongin C and Elongin B proteins in the case of VHL and ARNT protein, in the case of HIF a subunit protein.)

In cell free systems such additional proteins may be included, for example by being provided by expression from suitable recombinant expression vectors.

In assays performed in cells, it will be desirable to achieve sufficient expression of VHL to recruit sufficient HIFα subunit to a complex such that the effect of a putative modulator compound may be measured. The level of expression of VHL and HIFα subunit may be varied within fairly wide limits, so that the intracellular levels of the two may vary by a wide ratio, for example from 1:10 to 1000:1, preferably 1:1 to 100:1, molar ratio of VHL to HIFα subunit.

The amount of putative modulator compound which may be added to an assay of the invention will normally be determined by trial and error depending upon the type of compound used. Typically, from about 0.01 to 100 μM concentrations of putative modulator compound may be used, for example from 0.01 to 10 μM. Modulator compounds may be those which either agonize or antagonize the interaction. Antagonists (inhibitors) of the interaction are particularly desirable.

Modulator compounds which may be used may be natural or synthetic chemical compounds used in drug screening programs. Extracts of plants which contain several characterized or uncharacterized components may also be used.

The invention provides methods for determining hypoxic conditions, cancer or infection in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.) Yet another aspect of the invention pertains to monitoring the influence of agents (e.g., drugs, compounds) on hypoxic conditions, cancer or infection in clinical trials.

Thus, the diagnostic methods described herein can furthermore be utilized to identify subjects having or at risk of developing a disease or disorder associated with hypoxic conditions, cancer or infection. Furthermore, the prognostic assays described herein can be used to determine whether a subject should be administered an agent (e.g., an agonist, antagonist, peptidomimetic, protein, peptide, nucleic acid, small molecule, or other drug candidate) to treat a disease or disorder associated with hypoxic conditions, cancer or infection.

The selection of a light-generating polypeptide moiety of the light-generating fusion protein should be done so as to produce light capable of penetrating animal tissue such that it can be detected externally in a non-invasive manner. The ability of light to pass through a medium such as animal tissue (composed mostly of water) is determined primarily by the light's intensity and wavelength.

The more intense the light produced in a unit volume, the easier the light will be to detect. The intensity of light produced in a unit volume depends on the spectral characteristics of individual light-generating polypeptide moieties, and on the concentration of those moieties in the unit volume. Accordingly, schemes that place a high concentration of light-generating polypeptide moieties in or on an entity (such as high-efficiency loading of a liposome or high-level expression of a light-generating fusion protein in a cell) typically produce brighter light-generating fusion proteins (LGPs), which are easier to detect through deeper layers of tissue, than schemes which conjugate, for example, only a single LGM onto each entity.

A second factor governing detectability through a layer of tissue is the wavelength of the emitted light. Water may be used to approximate the absorption characteristics of animal tissue, since most tissues are composed primarily of water. It is well known that water transmits longer-wavelength light (in the red range) more readily than it does shorter wavelength light.

Accordingly, light-generating polypeptide moieties which emit light in the range of is yellow to red (550-1100 nm) are typically preferable to those which emit at shorter wavelengths. However, excellent results can be achieved in practicing the present invention with LGMs that emit in the range of 486 nm, despite the fact that this is not an optimal emission wavelength.

Fluorescence-based Moieties. Because fluorescent molecules require input of light in order to luminance, their use in the invention may be more involved than the use of bioluminescent molecules. Precautions are typically taken to shield the excitatory light so as not to contaminate the fluorescence photon signal being detected from the subject. Obvious precautions include the placement of an excitation filter at the radiation source. An appropriately-selected excitation filter blocks the majority of photons having a wavelength similar to that of the photons emitted by the fluorescent moiety. Similarly, a barrier filter is employed at the detector to screen out most of the photons having wavelengths other than that of the fluorescence photons. Filters such as those described above can be obtained from a variety of commercial sources, including Omega Optical, Inc. (Brattleboro, Vt.).

Alternatively, a laser producing high intensity light near the appropriate excitation wavelength, but not near the fluorescence emission wavelength, can be used to excite the fluorescent moieties. An x-y translation mechanism may be employed so that the laser can scan the subject, for example, as in a confocal microscope.

As an additional precaution, the radiation source may be placed behind the subject and shielded, such that the only radiation photons reaching the site of the detector are those that pass all the way through the subject. Furthermore, detectors may be selected that have a reduced sensitivity to wavelengths of light used to excite the fluorescent moiety.

An advantage of small fluorescent molecules is that they are less likely to interfere with the bioactivity of the entity to which they are attached than a would a larger light-generating moiety. In addition, commercially-available fluorescent molecules can be obtained with a variety of excitation and emission spectra that are suitable for use with the present invention. For example, Molecular Probes (Eugene, Oreg.) sells a number of fluorophores, including Lucifer Yellow (abs. at 428 nm, and emits at 535 nm) and Nile Red (abs. at 551 nm and emits at 636 nm). Further, the molecules can be obtained derivatized with a variety of groups for use with various conjugation schemes (e.g., from Molecular Probes).

Bioluminescence-based Moieties. The subjects of chemiluminescence (luminescence as a result of a chemical reaction) and bioluminescence (visible luminescence from living organisms) have, in many aspects, been thoroughly studied.

An advantage of bioluminescent moieties over fluorescent moieties, is that there is virtually no background in the signal. The only light detected is light that is produced by the exogenous bioluminescent moiety. In contrast, the light used to excite a fluorescent molecule often results in the fluorescence of substances other than the intended target. This is particularly true when the "background" is as complex as the internal environment of a living animal.

Ligands include, in a preferred embodiment, enzymes which are capable of modifying a light-generating polypeptide moiety such that it does or ceases to emit light when modified. In use, this happens when, e.g., the light-generating fusion protein comes in contact with a ligand on an entity or produced by the entity, and the ligand binds to the ligand binding site, altering the light-generating properties of the light-generating polypeptide moiety. Examples include the following.

In an especially useful embodiment of the present invention, a light-generating fusion protein comprising a binding site for an E3 ubiquitin ligase and a light-generating polypeptide moiety capable of being modified by E3 at a modification site can be used for diagnostic and treatment purposes. Ubiquitin ligases (e.g., E3) bind to colinear 'T' (see FIG. 1) present on their substrates. Examples include the SCF (Skp1/Cdc53/F-box) ubiquitin ligases, the VBC (pVHL/elongin B/elongin C) ubiquitin ligase, and the MDM2 ubiquitin ligase. It is already established that light-generating proteins such as GFP and luciferase can be fused to heterologous polypeptides without loss of activity. In some embodiments, the light-generating polypeptide moiety may be modified to include a surface exposed lysine residue accessible as a ubiquitin acceptor site. In a First embodiment, a light-generating fusion protein of the invention may be used to monitor ischemia in living tissues and animals. The First embodiment comprises a polypeptide derived from the HIF1α (hypoxia-inducible factor 1α) which acts as a binding site for VBC. This binding site is only recognized by VBC in the presence of oxygen as a result of proline hydroxylation. The light-generating fusion protein of the First embodiment is advantageously stable in hypoxic cells, but unstable in well oxygenated cells. In a related embodiment, the HIF-derived polypeptide described above may be fused to a suicide moiety such as a protein (such as HSV TK or an adenoviral protein like E1A), which can be used in selective killing of ischemic cells (such as in a solid tumor).

Binding and/or modification sites are well-known in the art for a variety of kinases is including cyclin-dependent kinases, ATM/ATR, JNK kinases, and receptor tyrosine kinases. In one embodiment, a light-generating fusion protein may be fused to a binding site for a kinase of interest. In some embodiments, it is useful to introduce one or more binding sites for a selected kinase into the light-generating fusion protein. By way of example, since phosphorylated serine, threonine, and tyrosine, by virtue of their negative charges, frequently mimic aspartic acid and/or glutamic acid residues, individual aspartic acid and glutamic acid residues are replaced with serine, threonine, or tyrosine (in the context of the kinase modification site). Such substitutions may be made singly and in combination. In another embodiment, the modification site can be empirically determined by carrying out a linker scan of the light-generating protein using a linker encoding the kinase modification site. In yet another embodiment the light-generating polypeptide moiety is mutagenized (either random or targeted mutagenesis) to generate modification sites in which the light-generating polypeptide moiety is selectively inactivated or activated by the kinase; this mutagenesis is performed using cells (such as yeast) rendered conditional for the kinase. In still yet another embodiment, a kinase modification site is designed in silico based on comparison of the binding site of the selected kinase to the primary sequence of the light-generating polypeptide moiety, coupled with knowledge of the three dimensional structure of the light-generating polypeptide moiety.

In an additional embodiment described below, a light-generating polypeptide moiety is fused to a polypeptide recognized by a cyclin/cdk2 complex. This enzyme phosphorylates serine or threonine with an absolute requirement for proline in the +1 position. By way of example, GFP contains 13 proline residues including one threonine-proline site and two aspartic acid-proline sites. In one embodiment, a light-generating protein (e.g., GFP) is fused to a cyclin/cdk2 binding site such as Y-Lys-$X_1$-Leu-K—$X_2$-Leu-Y' (SEQ ID NO. 9). The light-generating protein is phosphorylated and inactivated by cyclin/cdk2, providing a detectable signal which is selectively off in the presence of cyclin/cdk2. In another embodiment, the light-generating polypeptide moiety is mutated so that it is not phosphorylated and activated by cyclin/cdk2. An example of this mutation would be to mutate the two aspartic acid-proline sites to serine (or threonine)-prolines.

In this additional embodiment, the ligand binding site is a polypeptide recognized by a cyclin/cdk2 complex, e.g., comprising the amino acid sequence Y-Lys-$X_1$-Leu-K—$X_2$-Leu-Y', wherein $X_1$, $X_2$ are independently any one or more amino acids; and Y and Y' are independently present or absent and, if present, independently comprise a peptide having from 1 to 600 amino acids.

An example of such a target peptide is RB: PKPLKKLRFD (SEQ ID NO: 1). In a related aspect of this additional embodiment, the ligand binding site comprises the amino acid sequence Y—$X_1$-Arg-Arg-Leu-Y', wherein $X_1$ is Lys or Cys; and Y and Y' are independently present or absent and, if present, independently comprise a peptide having from 1 to 600 amino acids. Two non-limiting examples of the target peptide of this related aspect of this additional embodiment are: E2F1: GRPPVKRRLDLE (SEQ ID NO: 2); derived from the E2F1 protein, and p21: CCSKACRRLFGP (SEQ ID NO: 3), derived from the p21 protein.

The fusion protein of this additional embodiment can be produced by standard recombinant DNA techniques, discussed supra.

The ligand binding site of the light-generating fusion protein of this additional embodiment is derived from the retinoblastoma (RB) protein. Adams, et al., 1999 *Mol. Cell. Biol.* 19:1068 describes RB protein. An RB polypeptide comprises 928 amino acid residues. As described in more detail below, this ligand binding site comprises a unique cyclin binding domain derived from RB. In the light-generating fusion protein described above, where present, Y comprises between 1 and 900 amino acid residues, preferably corresponding to the sequence of "N-terminal" RB amino acid residues 1-868. Thus, in a preferred embodiment Y can represent any sequence of N-terminal amino acids of RB, for example residues 794-829, and so on up to and including residues 1-868. Y' can also comprise between 1 and 600 amino acid residues, preferably corresponding to the sequence of "C-terminal" RB amino acid residues 879-928. Thus, in a preferred embodiment, Y' can represent any sequence of C-terminal amino acids of RB, for example 879-910, and so on up to and including residues 879-928. Y and Y' can also contain conservative substitutions of amino acids present in the N-terminal and C-terminal RB sequences described above. In a further preferred embodiment, Y and Y' are absent.

The light-generating fusion protein of this additional embodiment provides a way for detecting "cancerous tissue" or tissue subject to aberrant cell proliferation and therefore at risk for cancer. In addition to tissue that becomes cancerous due to an in situ neoplasm, for example, the light-generating fusion protein also provides a method of detecting cancerous metastatic tissue present in distal organs and/or tissues. Thus such tissue may be detected by contacting tissue suspected of being cancerous with the light-generating fusion protein under appropriate conditions to cause the phosphorylation of the light-generating fusion protein in cancerous tissue, thereby detecting the presence of cancerous tissue. The ligand binding site of the light-generating fusion protein of this embodiment provides a binding site for cyclin-cyclin-dependent kinase (cdk) complexes which phosphorylate the protein, causing it to emit or not emit light in the presence of active cycle-cdk complexes. Under appropriate conditions, the light-generating fusion protein will therefore be phosphorylated or inactive in tissue that is not cancerous, and unphosphorylated and preserving its light-emitting properties in tissue that is cancerous, e.g. primary and metastatic tissue.

In another useful embodiment, a light-generating polypeptide moiety is fused to a polypeptide recognized by a cyclin/cdk2 complex. This enzyme phosphorylates serine or threonine with an absolute requirement for proline in the +1 position. By way of example, GFP contains 13 proline residues including one threonine-proline site and two aspartic acid-proline sites. In one embodiment, a light-generating protein (e.g., GFP) is fused to a cyclin/cdk2 binding site such as Y-Lys-$X_1$-Leu-K—$X_2$-Leu-Y' (SEQ ID NO. 9). The light-generating protein is phosphorylated and inactivated by cyclin/cdk2, providing a detectable signal which is selectively off in the presence of cyclin/cdk2. In another embodiment, the light-generating polypeptide moiety is mutated so that it is not phosphorylated and activated by cyclin/cdk2. An example of this mutation would be to mutate the two aspartic acid-proline sites to serine (or threonine)-prolines.

Phosphorylation is one of the most important ways to post-translationally modify proteins, and it regulates diverse cell physiological processes (transport, proliferation, differentiation). For example, phosphorylation is involved in all phases of cell division: in transition from G1 to S phase, progression of cells during S phase and entry into M phase. The physiological function of oncoproteins and tumor suppressor proteins that are involved in gene expression and replication are also regulated by phosphorylation. Many growth factors and their receptors are encoded by oncogenes which are mutated or overexpressed in a variety of human tumors. Mutation or overexpression of these oncogenes leads to unchecked cell division, and transformation of normal cells to malignant. In an embodiment of the present invention, a light-generating fusion protein may include a phosphatase binding site and a modification site, such as a phosphorylated amino acid residue capable of being modified by a protein "phosphatase".

For most proteases, the enzyme binding site and modification site are largely congruent and can be encompassed in short peptides. In an embodiment, a light-generating fusion protein may include a protease binding site and a modification site capable of being cleaved by the protease. The binding site and modification site may be the same site or in two discrete regions. In one embodiment, wherein the binding and modification site are congruent, linker scanning mutagenesis of a given light-generating protein is carried out using a linker that encodes the congruent binding/modification site. Resulting mutants are those light-generating fusion proteins containing a binding/modification site that preserves light-emitting activity in protease deficient cells and exhibits protease sensitivity in vitro and in vivo. In the Third embodiment described herein, a light-generating fusion protein containing an HIV protease site is especially useful for monitoring the presence or absence of HIV (in this case, with HIV-positive cells not emitting light). In an alternative embodiment, the light-generating fusion protein is fused via a linker to a protein that inhibits the light-emitting activity of the light-generating polypeptide moiety. The linker includes a binding/modification site for an HIV protease. Thus, cleavage at the binding/modification site should remove the inhibiting protein moiety, thus yielding a positive signal in cells that are HIV positive.

As shown generally in FIG. 1A, an embodiment of the fusion protein of the invention contains a ligand binding site "T", a reporter domain (e.g., light-generating polypeptide moiety) "R", and a modification site "X". Binding of enzyme "E" (the ligand) to target site "T" results in a modification of modification site "X", which causes the reporter domain "R" to either emit or not emit light.

Figure 1B:
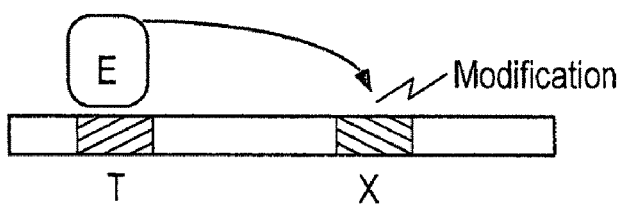

The site "T" and modification site "X" may be separate and in cis on the fusion protein, as shown in FIG. 1B. Either "T" or "X" can be proximal or distal to the amino terminus of the fusion protein.

Figure 1C:
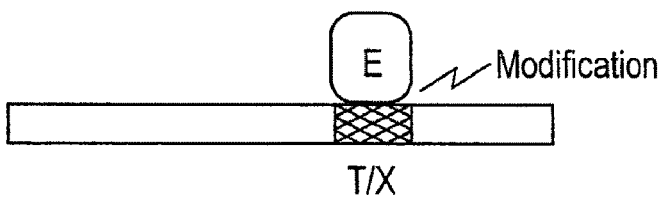

In another embodiment shown in FIG. 1C, wherein the "T" and the "X" of the fusion protein are congruent within a domain of the fusion protein. In related embodiments, the congruent "T/X" can be at the amino terminus, the carboxy terminus, or at neither terminus of the fusion protein.

Figure 1D:
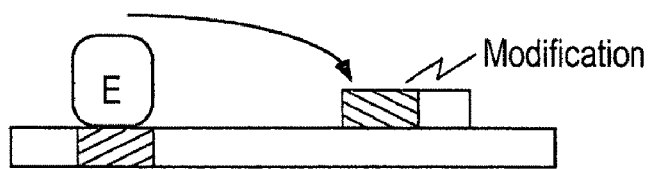

In a further embodiment shown in FIG. 1D, the "T" is on a protein associated with the fusion protein containing the "X". In a related embodiment, target site "T" is on the fusion protein and modification site "X" is on a protein that is physically associated with the fusion protein, wherein modification of the associated protein results in the fusion protein either emitting or not emitting light. The depiction of site "T" and modification site "X" are not intended to be limiting. "T" can be at the amino terminus, the carboxy terminus, or at neither terminus of the fusion protein, and "X" can be at the amino terminus, the carboxy terminus, or at neither terminus of the associated protein.

Figure 2A:
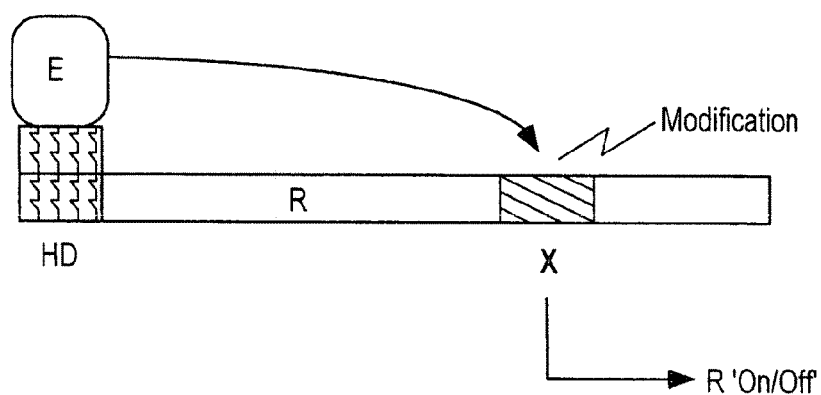
FIG. 2 is a second schematic representation of different fusion proteins of the invention.

The invention also includes a fusion protein in which the ligand binding site sequence "T" is unknown. In this embodiment, e.g., as shown in FIG. 2A, the fusion protein includes a first hetero- or homo-dimerization domain ("HD1"). An enzyme "E" capable of modifying modification site "X" on the fusion protein is fused to a second hetero- or homo-dimerization domain "HD2" that interacts with "HD1". In a related embodiment, the targeting site "T" for an enzyme "E" can be generated by inserting one or more polypeptide sequences derived from a random or non-random peptide library into the fusion protein.

In a related embodiment (FIG. 2B), a binding domain of a protein "A" containing an enzyme target site "T" interacts with a binding domain "B" of a fusion protein, which results in enzyme "E" modifying the reporter domain "R" of fusion protein "B" at modification site "X" such that the fusion protein does or does not emit light or cause light to be emitted. In the First embodiment, the ligand binding site comprises a polypeptide derived from the HIF1α (hypoxia-inducible factor 1α) which acts as a binding site for VBC, e.g., the amino acid sequence Y—$X_1$-Leu-$X_2$-Pro$_h$-$X_3$—$X_4$—$X_5$—$X_6$—Y', wherein Pro$_h$ is hydroxylated proline;

$X_1$, $X_2$, $X_3$, $X_4$, $X_5$, and $X_6$ are amino acids selected so as to not modify or alter VBC binding properties. $X_1$, $X_2$, $X_4$, $X_5$, and $X_6$ are desirably independently Gly, Ala, Val, Leu, Ile, Pro, Met, Phe, or Trp, and $X_3$ is desirably Ser, Thr, or Tyr; and Y and Y' are independently present or absent and, if present, independently comprise a peptide having from 1 to 600 amino acids.

In a preferred embodiment, the ligand binding site comprises the amino acid sequence corresponding to the N-terminal residues 1-600 of HIF1α, wherein either or both of residues 402 and 564 are proline or hydroxylated proline. In a more preferred embodiment, the ligand binding site comprises an 80 to 120, 20 to 30, 12 to 14, or 4 to 12 amino acid sequence corresponding to the residues adjacent to and/or surrounding residue 402 and/or 564, inclusive, of HIF1α, wherein residues 402 and/or 564 is proline or hydroxylated proline. "Residues adjacent to and/or surrounding" is meant to include the relevant sequence of HIF1α either before, after, or flanking, the specified residue, e.g., residue 564.

Such proteins may be used effectively as oxygen-sensing proteins. The fusion proteins may be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel et al. (eds.) CURRENT PROTOCOLS IN MOLECULAR BIOLOGY, John Wiley & Sons, 1992).

The ligand binding site noted above is derived from HIF1α protein. U.S. Pat. No. 6,222,018, describes HIF protein and its preparation in substantially pure form. HIF is composed of subunits HIF1α and an isoform HIF1α. HIF1α polypeptide comprises 826 amino acid residues. As described in more detail below, the ligand binding sites of this particular fusion protein comprises a unique ubiquitin ligase binding domain derived from HIF1α. In this fusion protein, where present, Y comprises between 1 and 600 amino acid residue, preferably corresponding to the sequence of "N-terminal" HIF1α amino acid residues 1-555. Thus, in a preferred embodiment Y can represent any sequence of N-terminal amino acids of HIF1α, for example residues 554-555, 553-555, 552-555, and so on up to and including residues 1-555. Y' can also comprises between 1 and 600 amino acid residues, preferably corresponding to the sequence of "C-terminal" HIF1α amino acid residues 576-826. Thus, in a preferred embodiment, Y' can represent any sequence of C-terminal amino acids of HIF1α, for example 576-577, 576-578, 576-579, and so on up to and including residues 576-826. Y and Y' can also contain conservative substitutions of amino acids present in the N-terminal and C-terminal HIF1α sequences described above. In a preferred embodiment of the ligand binding site defined above, Y and Y' are absent. In a further preferred embodiment, $X_1$ is Met, $X_2$ is Leu, $X_3$ is Ala, $X_4$ is Tyr, $X_5$ is Pro, and $X_6$ is Met. In a particularly preferred embodiment of the fusion protein, the ligand binding site has the amino acid sequence Asp-Leu-Asp-Leu-Glu-Met-Leu -Ala-Pro$_h$-Tyr-Ile-Pro-Met-Asp-Asp-Asp-Phe-Gln-Leu-Arg, corresponding to HIF1α amino acid residues 556-575, with a hydroxylated proline at amino acid residue 564.

The invention also provides a nucleic acid molecule encoding the fusion protein or polypeptide of the invention. (As used herein, the terms polypeptide and protein are interchangeable). An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to the nucleotide sequences can be prepared by standard synthetic techniques, e.g., using an automated DNA synthesizer. The present invention therefore also provides a vector comprising the nucleic acid of the invention. In a preferred embodiment, the vector further comprises a promoter operably linked to the nucleic acid molecule. In a further preferred embodiment the invention provides a cell containing the vector of the invention.

The light-generating fusion protein of, e.g., the First embodiment provides a means for detecting hypoxic tissue or tissue subject to chronic hypoxia and therefore at risk for ischemia. In addition to tissue that becomes ischemic due to occurrence of a stroke, heart attack or embolism, for example, the fusion protein also provides a method of detecting ischemic tissue present in tumors. Thus the invention may be used to detect such tissue by contacting tissue suspected of being hypoxic with the light-generating fusion protein under appropriate conditions to cause the ubiquitination of the fusion protein in normoxic tissue, thereby detecting the presence of hypoxic tissue. As described more fully below, the ligand binding site of the light-generating fusion protein also provides a binding site for ubiquitin ligases which destroy the protein in the presence of oxygen. Under appropriate conditions, the light-generating fusion protein of the invention will therefore be "unstable" or destroyed in tissue that is not hypoxic, i.e., that is well oxygenated, and "stable" or preserving its light-emitting properties in tissue that is hypoxic, i.e. that lacks sufficient oxygen.

The Third embodiment provides a means for detecting "infected tissue" or tissue subject to contact with infectious agents and therefore at risk for infection, e.g., monitoring the presence or absence of HIV. The ligand binding site of the Third embodiment comprises a binding site for a protease, such as an infection-associated protease. For example, protease cleavage sites of the human immunodeficiency virus (HIV-1) protein precursor Pr55 (gag) protein include p2/NC, NC/p1, and NC/TFP.

The ligand binding site of the light-generating fusion protein of this Third embodiment may be derived from the HIV-1 protein. One non-limiting example of the target peptide of this Third embodiment is:

Y-GSGIF*LETSL-Y' (See Beck et al., (2000) Virology 274(2):391-401.

Y and Y' are independently present or absent and, if present, independently comprise a peptide having from 1 to 600 amino acids, and "*" indicates the cleavage site of the fusion protein by a protease.

In addition to tissue that becomes infected due to an acute or chronic infection by an infectious agent, for example, the light-generating fusion protein may be used in detecting infected tissue present in distal organs and/or tissues, e.g., by contacting tissue suspected of being infected with the light-generating fusion protein of the invention under appropriate conditions to cause the proteolysis of the light-generating fusion protein in infected tissue, thereby detecting the presence of infected tissue. The ligand binding site of the light-generating fusion protein of this Third embodiment provides a binding site for a protease which degrades or modifies the protein, causing it to emit or not emit light in the presence of one or more proteases. Under appropriate conditions, the light-generating fusion protein will therefore be proteolyzed or inactive in tissue that is infected (although there may be cases where proteolysis leads to light generation), and unproteolyzed and preserving its light-emitting properties in tissue that is infected.

A Fourth embodiment of a light-generating fusion protein of the invention comprises a light-generating protein moiety and a ligand binding site, wherein the ligand binding site comprises an amino acid sequence capable of binding to an "associated" protein. The association can occur by covalent or non-covalent binding. This associated protein may itself be a light-generating fusion protein, comprising a binding polypeptide capable of binding to the light-emitting light-generating fusion protein and an enzyme capable of modifying the light-emitting light-generating fusion protein.

A non-limiting example of the target peptide of this Fourth embodiment is:

HD1: WFHGKLSR (Amino acids 488-495 of Accession No. P29353, human SHC1; SEQ ID NO: 4).

This target polypeptide contains an SH2 domain. Therefore, any associated protein with an SH2 domain should interact with the target peptide of the Fourth embodiment. A non-limiting example of the binding peptide of the associated protein of this Fourth embodiment is:

HD2: WNVGSSNR (Amino acids 624-631 of Accession No. P27986; human PI3K p85 subunit; SEQ ID NO: 5).

Another non-limiting example of the Fourth embodiment would be to fuse the FK506 binding protein (FKBP12) domain moiety to GFP and the FRAP domain moiety to Skp1 or elonginc. Therefore in the presence of rapamycin, which promotes the high affinity interaction of FKBP12 and FRAP, the core E3 ligase machinery would bind to and destroy GFP, eliminating the bioluminescence wherever rapamycin is present.

The ligand binding site of the light-generating fusion protein of this Fourth embodiment is derived from the human SHC1 protein. See Pelicci et al., (1992) Cell 70:93-104, describes the SHC1 protein with an SH2 domain which is implicated in mitogenic signal transduction.

The light-generating fusion protein of this Fourth embodiment provides a means for detecting enzymatic activity where the enzyme binding site is undefined.

The pharmaceutical compositions of the invention comprise the novel agents combined with a pharmaceutically acceptable carrier. The term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal is suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The invention includes entities which may have been modified or conjugated to include a light-generating fusion protein of the invention. Such conjugated or modified entities are referred to as light-emitting entities, or simply conjugates. The conjugates themselves may take the form of, for example, molecules, macromolecules, particles, microorganisms, or cells. The methods used to conjugate a light-generating fusion protein to an entity depend on the nature of the light-generating fusion protein and the entity. Exemplary conjugation methods are discussed in the context of the entities described below.

Small molecules. Small molecule entities which may be useful in the present invention include compounds which specifically interact with a pathogen or an endogenous ligand or receptor. Examples of such molecules include, but are not limited to, drugs or therapeutic compounds; toxins, such as those present in the venoms of poisonous organisms, including certain species of spiders, snakes, scorpions, dinoflagellates, marine snails and bacteria; growth factors, such as NGF, PDGF, TGF and TNF; cytokines; and bioactive peptides.

The small molecules are preferably conjugated to light-generating fusion proteins in a way that that the bioactivity of the small molecule is not substantially affected. Conjugations are typically chemical in nature, and can be performed by any of a variety of methods known to those skilled in the art.

Small molecules conjugated to light-generating fusion proteins of the present invention may be used either in animal models of human conditions or diseases, or directly in human is subjects to be treated. For example, a small molecule which binds with high affinity to receptor expressed on tumor cells may be used in an animal model to localize and obtain size estimates of tumors, and to monitor changes in tumor growth or metastasis following treatment with a putative therapeutic agent. Such molecules may also be used to monitor tumor characteristics, as described above, in cancer patients.

Macromolecules. Macromolecules, such as polymers and biopolymers, constitute another example of entities useful in practicing the present invention. Exemplary macromolecules include antibodies, antibody fragments, light-generating fusion proteins and certain vector constructs.

Antibodies or antibody fragments, purchased from commercial sources or made by methods known in the art, can be used to localize their antigen in a mammalian subject by conjugating the antibodies to a light-generating polypeptide moiety, administering the conjugate to a subject by, for example, injection, allowing the conjugate to localize to the site of the antigen, and imaging the conjugate.

Antibodies and antibody fragments have several advantages for use as entities in the present invention. By their nature, they constitute their own targeting moieties. Further, their size makes them amenable to conjugation with several types of light-generating fusion proteins, including small fluorescent molecules and fluorescent and bioluminescent proteins, yet allows them to diffuse rapidly relative to, for example, cells or liposomes.

The light-generating fusion proteins can be conjugated directly to the antibodies or fragments, or indirectly by using, for example, a fluorescent secondary antibody. Direct conjugation can be accomplished by standard chemical coupling of, for example, a fluorophore to the antibody or antibody fragment, or through genetic engineering. Chimeras, or fusion proteins can be constructed which contain an antibody or antibody fragment coupled to a fluorescent or bioluminescent protein. For example, Casadei, et al., describe a method of making a vector construct capable of expressing a fusion protein of aequorin and an antibody gene in mammalian cells.

Conjugates containing antibodies can be used in a number of applications of the present invention. For example, a labeled antibody directed against E-selection, which is expressed at sites of inflammation, can be used to localize the inflammation and to monitor the effects of putative anti-inflammatory agents.

Vector constructs by themselves can also constitute macromolecular entities applicable to the present invention. For example, a eukaryotic expression vector can be constructed which contains a therapeutic gene and a gene encoding a light-generating molecule under the control of a selected promoter (i.e., a promoter which is expressed in the cells targeted by the therapeutic gene). Expression of the light-generating molecule, assayed using methods of the present invention, can be used to determine the location and level of expression of the therapeutic gene. This approach may be particularly useful in cases where the expression of the therapeutic gene has no immediate phenotype in the treated individual or animal model.

Viruses. Another entity useful for certain aspects of the invention are viruses. As many viruses are pathogens which infect mammalian hosts, the viruses may be conjugated to a light-generating fusion protein and used to study the initial site and spread of infection. In addition, viruses labeled with a light-generating fusion protein may be used to screen for drugs which inhibit the infection or the spread of infection.

A virus may be labeled indirectly, either with an antibody conjugated to a light-generating fusion protein, or by, for example, biotinylating virions as known in the art and then exposing them to streptavidin linked to a detectable moiety, such as a fluorescent molecule.

Alternatively, virions may be labeled directly with a fluorophore like rhodamine, using methods known in the art. The virus can also be genetically engineered to express a light-generating fusion protein. Labeled virus can be used in animal models to localize and monitor the progression of infection, as well as to screen for drugs effective to inhibit the spread of infection. For example, while herpes virus infections are manifested as skin lesions, this virus can also cause herpes encephalitis. Such an infection can be localized and monitored using a virus labeled by any of the methods described above, and various antiviral agents can be tested for efficacy in central nervous system (CNS) infections.

Particles. Particles, including beads, liposomes and the like, constitute another entity useful in the practice of the present invention. Due to their larger size, particles may be conjugated with a larger number of light-generating fusion proteins than, for example, can small molecules. This results in a higher concentration of light emission, which can be detected using shorter exposures or through thicker layers of tissue. In addition, liposomes can be constructed to contain an essentially pure targeting moiety, or ligand, such as an antigen or an antibody, on their surface. Further, the liposomes may be loaded with, for example, light-generating protein molecules, to relatively high concentrations.

Furthermore, two types of liposomes may be targeted to the same cell type such that light is generated only when both are present. For example, one liposome may carry luciferase, while the other carries luciferin. The liposomes may carry targeting moieties, and the targeting moieties on the two liposomes may be the same or different. Viral proteins on infected cells can be used to identify infected tissues or organs. Cells of the immune system can be localized using a single or multiple cell surface markers.

The liposomes are preferably surface-coated, e.g., by incorporation of phospholipid-polyethyleneglycol conjugates, to extend blood circulation time and allow for greater targeting via the bloodstream. Liposomes of this type are well known.

Cells. Cells, both prokaryotic and eukaryotic, constitute another entity useful in the practice of the present invention. Like particles, cells can be loaded with relatively high concentrations of light-generating moieties, but have the advantage that the light-generating moieties can be provided by, for example, a heterologous genetic construct used to transfect the cells. In addition, cells can be selected that express "targeting moieties", or molecules effective to target them to desired locations within the subject. Alternatively, the cells can be transfected with a vector construct expressing an appropriate targeting moiety.

The cell type used depends on the application. For example, bacterial cells can be used to study the infective process, and to evaluate the effects of drugs or therapeutic agents on the infective process with a high level of temporal and spatial resolution. Bacterial cells constitute effective entities. For example, they can be easily transfected to express a high levels of a light-generating fusion protein, as well as high levels of a targeting protein. In addition, it is possible to obtain $E.\ coli$ libraries containing bacteria expressing surface-bound antibodies which can be screened to identify a colony expressing an antibody against a selected antigen (Stratagene, La Jolla, Calif.). Bacteria from this colony can then be transformed with a second plasmid containing a gene for a light-generating protein, and transformants can be utilized in the methods of the present invention, as described above, to localize the antigen in a mammalian host.

Pathogenic bacteria can be conjugated to a light-generating fusion protein and used in an animal model to follow the infection process in vivo and to evaluate potential anti-infective drugs, such as new antibiotics, for their efficacy in inhibiting the infection.

Eukaryotic cells are also useful as entities in aspects of the present invention. Appropriate expression vectors, containing desired regulatory elements, are commercially available. The vectors can be used to generate constructs capable of expressing desired light-generating proteins in a variety of eukaryotic cells, including primary culture cells, somatic cells, lymphatic cells, etc. The cells can be used in transient expression studies, or, in the case of cell lines, can be selected for stable transformants.

Expression of the light-generating protein in transformed cells can be regulated using any of a variety of selected promoters. For example, if the cells are to be used as light-emitting entities targeted to a site in the subject by an expressed ligand or receptor, a constitutively-active promoter, such as the CMV or SV40 promoter may be used. Cells transformed with such a construct can also be used to assay for compounds that inhibit light generation, for example, by killing the cells.

Alternatively, the transformed cells may be administered such they become uniformly distributed in the subject, and express the light-generating fusion protein only under certain conditions, such as upon infection by a virus or stimulation by a cytokine. Promoters that respond to factors associated with these and other stimuli are known in the art. In a related aspect, inducible promoters, such as the Tet system can be used to transiently activate expression of the light-generating protein.

For example, CD4+ lymphatic cells can be transformed with a construct containing tat-responsive HIV LTR elements, and used as an assay for infection by HIV. Cells transformed with such a construct can be introduced into SCID-hu mice and used as model for human HIV infection and AIDS.

Tumor cell lines transformed to express the light-generating fusion protein, for example, with a constitutively-active promoter, may be used to monitor the growth and metastasis of tumors. Transformed tumor cells may be injected into an animal model, allowed to form a tumor mass, and the size and metastasis of the tumor mass monitored during treatment with putative growth or metastasis inhibitors. Tumor cells may also be generated from cells transformed with constructs containing regulatable promoters, whose activity is sensitive to various infective agents, or to therapeutic compounds.

Cell Transformation. Transformation methods for both prokaryotic cells and eukaryotic cells are well known in the art. Vectors containing the appropriate regulatory elements and multiple cloning sites are widely commercially available (e.g., Stratagene, La Jolla, Calif., or Clontech, Palo Alto, Calif.).

In another aspect, the present invention includes transgenic animals containing a heterologous gene construct encoding a light-generating fusion protein or complex of proteins. The construct is driven by a selected promoter, and can include, for example, various accessory proteins required for the functional expression of the light-generating protein, as well as selection markers and enhancer elements.

Activation of the promoter results in increased expression of the genes encoding the light-generating fusion proteins and accessory proteins. Activation of the promoter is achieved by the interaction of a selected biocompatible entity, or parts of the entity, with the promoter elements. If the activation occurs only in a part of the animal, only cells in that part will express the light-generating protein.

Light-generating fusion proteins are typically administered to a subject by any of a variety of methods, allowed to localize within the subject, and imaged. Since the imaging, or measuring photon emission from the subject, may last up to tens of minutes, the subject is desirably immobilized during the imaging process. Imaging of the light-generating polypeptide moiety involves the use of, e.g., a photodetector capable of detecting extremely low levels of light—typically single photon events—and integrating photon emission until an image can be constructed. Examples of such sensitive photodetectors include devices that intensify the single photon events before the events are detected by a camera, and cameras (cooled, for example, with liquid nitrogen) that are capable of detecting single photons over the background noise inherent in a detection system.

Once a photon emission image is generated, it is typically superimposed on a "normal" reflected light image of the subject to provide a frame of reference for the source of the emitted photons (i.e., localize the light-generating fusion proteins with respect to the subject). Such a "composite" image is then analyzed to determine the location and/or amount of a target in the subject.

Light-generating fusion proteins that have localized to their intended sites in a subject may be imaged in a number of ways. Guidelines for such imaging, as well as specific examples, are described below.

Localization of Light-generating fusion proteins. In the case of "targeted" conjugates, that is, conjugates which contain a targeting moiety—a molecule or feature designed to localize the conjugate within a subject or animal at a particular site or sites, localization refers to a state when, an equilibrium between bound, "localized", and unbound, "free" entities within a subject has been essentially achieved. The rate at which such an equilibrium is achieved depends upon the route of administration. For example, a conjugate administered by intravenous injection to localize thrombi may achieve localization, or accumulation at the thrombi, within minutes of injection. On the other hand, a conjugate administered orally to localize an infection in the intestine may take hours to achieve localization.

Alternatively, localization may simply refer to the location of the entity within the subject or animal at selected time periods after the entity is administered. In a related aspect, localization of, for example, injected tumors cells expressing a light-generating moiety, may consist of the cells colonizing a site within the animal and forming a tumor mass.

By way of another example, localization is achieved when an entity becomes distributed following administration. For example, in the case of a conjugate administered to measure the oxygen concentration in various organs throughout the subject or animal, the conjugate becomes "localized", or informative, when it has achieved an essentially steady-state of distribution in the subject or animal.

In all of the above cases, a reasonable estimate of the time to achieve localization may be made by one skilled in the art. Furthermore, the state of localization as a function of time may be followed by imaging the light-emitting conjugate according to the methods of the invention.

The "photodetector device" used should have a high enough sensitivity to enable the imaging of faint light from within a mammal in a reasonable amount of time, and to use the signal from such a device to construct an image.

In cases where it is possible to use light-generating moieties which are extremely bright, and/or to detect light-generating fusion proteins localized near the surface of the subject or animal being imaged, a pair of "night-vision" goggles or a standard high-sensitivity video camera, such as a Silicon Intensified Tube (SIT) camera (e.g. Hammamatsu Photonic Systems, Bridgewater, N.J.), may be used. More typically, however, a more sensitive method of light detection is required.

In extremely low light levels the photon flux per unit area becomes so low that the scene being imaged no longer appears continuous. Instead, it is represented by individual photons which are both temporally and spatially distinct form one another. Viewed on a monitor, such an image appears as scintillating points of light, each representing a single detected photon. By accumulating these detected photons in a digital image processor over time, an image can be acquired and constructed. In contrast to conventional cameras where the signal at each image point is assigned an intensity value, in photon counting imaging the amplitude of the signal carries no significance. The objective is to simply detect the presence of a signal (photon) and to count the occurrence of the signal with respect to its position over time.

At least two types of photodetector devices, described below, can detect individual photons and generate a signal which can be analyzed by an image processor. Reduced-Noise Photodetection Devices achieve sensitivity by reducing the background noise in the photon detector, as opposed to amplifying the photon signal. Noise is reduced primarily by cooling the detector array. The devices include charge coupled device (CCD) cameras referred to as "backthinned", cooled CCD cameras. In the more sensitive instruments, the cooling is achieved using, for example, liquid nitrogen, which brings the temperature of the CCD array to approximately −120° C. "Backthinned" refers to an ultra-thin backplate that reduces the path length that a photon follows to be detected, thereby increasing the quantum efficiency. A particularly sensitive backthinned cryogenic CCD camera is the "TECH 512", a series 200 camera available from Photometrics, Ltd. (Tucson, Ariz.).

"Photon amplification devices" amplify photons before they hit the detection screen. This class includes CCD cameras with intensifiers, such as microchannel intensifiers. A microchannel intensifier typically contains a metal array of channels perpendicular to and co-extensive with the detection screen of the camera. The microchannel array is placed between the sample, subject, or animal to be imaged, and the camera. Most of the photons entering the channels of the array contact a side of a channel before exiting. A voltage applied across the array results in the release of many electrons from each photon collision. The electrons from such a collision exit their channel of origin in a "shotgun" pattern, and are detected by the camera.

Even greater sensitivity can be achieved by placing intensifying microchannel arrays in series, so that electrons generated in the first stage in turn result in an amplified signal of electrons at the second stage. Increases in sensitivity, however, are achieved at the expense of spatial resolution, which decreases with each additional stage of amplification. An exemplary microchannel intensifier-based single-photon detection device is the C2400 series, available from Hamamatsu.

Image Processors process signals generated by photodetector devices which count photons in order to construct an image which can be, for example, displayed on a monitor or printed on a video printer. Such image processors are typically sold as part of systems which include the sensitive photon-counting cameras described above, and accordingly, are available from the same sources. The image processors are usually connected to a personal computer, such as an IBM-compatible PC or an Apple Macintosh (Apple Computer, Cupertino, Calif.), which may or may not be included as part of a purchased imaging system. Once the images are in the form of digital files, they can be manipulated by a variety of image processing programs (such as "ADOBE PHOTOSHOP", Adobe Systems, Adobe Systems, Mt. View, Calif.) and printed.

The Detection Field Of The Device is defined as the area from which consistent measurements of photon emission can be obtained. In the case of a camera using an optical lens, the detection field is simply the field of view accorded to the camera by the lens. Similarly, if the photodetector device is a pair of "night vision" goggles, the detection field is the field of view of the goggles.

Alternatively, the detection field may be a surface defined by the ends of fiber-optic cables arranged in a tightly-packed array. The array is constructed to maximize the area covered by the ends of the cables, as opposed to void space between cables, and placed in close proximity to the subject. For instance, a clear material such as plexiglass can be placed adjacent the subject, and the array fastened adjacent the clear material, opposite from the subject.

The fiber-optic cable ends opposite the array can be connected directly to the detection or intensifying device, such as the input end of a microchannel intensifier, eliminating the need for a lens. An advantage of this method is that scattering and/or loss of photons is reduced by eliminating a large part of the air space between the subject and the detector, and/or by eliminating the lens. Even a high-transmission lens transmits only a fraction of the light reaching the front lens element.

With higher-intensity LGPs, photodiode arrays may be used to measure photon emission. A photodiode array can be incorporated into a relatively flexible sheet, enabling the practitioner to partially "wrap" the array around the subject. This approach also minimizes photon loss, and in addition, provides a means of obtaining three-dimensional images of the bioluminescence. Other approaches may be used to generate three-dimensional images, including multiple detectors placed around the subject or a scanning detector or detectors.

It will be understood that the entire animal or subject need not necessarily be in the detection field of the photodetection device. For example, if one is measuring a light-emitting conjugate known to be localized in a particular region of the subject, only light from that region, and a sufficient surrounding "dark" zone, need be measured to obtain the desired information.

Immobilizing the subject. In those cases where it is desired to generate a two-dimensional or three-dimensional image of the subject, the subject may be immobilized in the detection field of the photodetection devices during the period that photon emission is being measured. If the signal is sufficiently bright that an image can be constructed from photon emission measured in less than about 20 milliseconds, and the subject is not particularly agitated, no special immobilization precautions may be required, except to insure that the subject is in the field of the detection device at the start of the measuring period.

If, on the other hand, the photon emission measurement takes longer than about 20 msec, and the subject is agitated, precautions to insure immobilization of the subject during photon emission measurement, commensurate with the degree of agitation of the subject, need to be considered to preserve the spatial information in the constructed image. For example, in a case where the subject is a person and photon emission measurement time is on the order of a few seconds, the subject may simply be asked to remain as still as possible during photon emission measurement (imaging). On the other hand, if the subject is an animal, such as a mouse, the subject can be immobilized using, for example, an anesthetic or a mechanical restraining device.

In cases where it is desired to measure only the total amount of light emanating from a subject or animal, the subject does not necessarily need to be immobilized, even for long periods of photon emission measurements. All that is required is that the subject be confined to the detection field of the photodetector during imaging. It will be appreciated, however, that immobilizing the subject during such measuring may improve the consistency of results obtained, because the thickness of tissue through which detected photons pass will be more uniform from animal to animal.

Further Considerations During Imaging

The visualization of fluorescent light-generating moieties requires an excitation light source, as well as a photodetector. Furthermore, it will be understood that the excitation light source is turned on during the measuring of photon emission from the light-generating moiety.

Appropriate selection of a fluorophore, placement of the light source and selection and placement of filters, all of which facilitate the construction of an informative image, are discussed above, in the section on fluorescent light-generating moieties.

High-Resolution Imaging. Photon scattering by tissue limits the resolution that can be obtained by imaging LGMs through a measurement of total photon emission. It will be understood that the present invention also includes embodiments in which the light-generation of LGMs is synchronized to an external source which can be focused at selected points within the subject, but which does not scatter significantly in tissue, allowing the construction of higher-resolution images. For example, a focused ultrasound signal can be used to scan, in three dimensions, the subject being imaged. Light-generation from areas which are in the focal point of the ultrasound can be resolved from other photon emission by a characteristic oscillation imparted to the light by the ultrasound.

Constructing an Image of Photon Emission. In cases where, due to an exceptionally bright light-generating moiety and/or localization of light-generating fusion proteins near the surface of the subject, a pair of "night-vision" goggles or a high sensitivity video camera was used to obtain an image, the image is simply viewed or displayed on a video monitor. If desired, the signal from a video camera can be diverted through an image processor, which can store individual video frames in memory for analysis or printing, and/or can digitize the images for analysis and printing on a computer.

Alternatively, if a photon counting approach is used, the measurement of photon emission generates an array of numbers, representing the number of photons detected at each pixel location, in the image processor. These numbers are used to generate an image, typically by normalizing the photon counts (either to a fixed, pre-selected value, or to the maximum number detected in any pixel) and converting the normalized number to a brightness (greyscale) or to a color (pseudocolor) that is displayed on a monitor. In a pseudocolor representation, typical color assignments are as follows. Pixels with zero photon counts are assigned black, low counts blue, and increasing counts colors of increasing wavelength, on up to red for the highest photon count values. The location of colors on the monitor represents the distribution of photon emission, and, accordingly, the location of light-generating fusion proteins.

In order to provide a frame of reference for the conjugates, a greyscale image of the (still immobilized) subject from which photon emission was measured is typically constructed. Such an image may be constructed, for example, by opening a door to the imaging chamber, or box, in dim room light, and measuring reflected photons (typically for a fraction of the time it takes to measure photon emission). The greyscale image may be constructed either before measuring photon emission, or after. The image of photon emission is typically superimposed on the greyscale image to produce a composite image of photon emission in relation to the subject.

If it is desired to follow the localization and/or the signal from a light-emitting conjugate over time, for example, to record the effects of a treatment on the distribution and/or localization of a selected biocompatible moiety, the measurement of photon emission, or imaging can be repeated at selected time intervals to construct a series of images. The intervals can be as short as minutes, or as long as days or weeks.

Analysis of Photon Emission Images Images generated by methods and/or using compositions of the present invention may be analyzed by a variety of methods. They range from a simple visual examination, mental evaluation and/or printing of a hardcopy, to sophisticated digital image analysis. Interpretation of the information obtained from an analysis depends on the phenomenon under observation and the entity being used.

Applications: Localization of Tumor Cells

The growth and metastatic spread of tumors in a subject may be monitored using methods and compositions of the present invention. In particular, in cases where an individual is diagnosed with a primary tumor, LGPs directed against the cells of the tumor can be used to both define the boundaries of the tumor, and to determine whether cells from the primary tumor mass have migrated and colonized distal sites. For example, LGPs, such as liposomes containing antibodies directed against tumor antigens and loaded with LGPs, can be administered to a subject, allowed to bind to tumor cells in the subject, imaged, and the areas of photon emission can be correlated with areas of tumor cells.

In a related aspect, images utilizing tumor-localizing LGPs, such as those described above, may be generated at selected time intervals to monitor tumor growth, progression and metastasis in a subject over time. Such monitoring may be useful to record results of anti-tumor therapy, or as part of a screen of putative therapeutic compounds useful in inhibiting tumor growth or metastasis.

In the practice of the invention, the tissue and the light-generating fusion protein can be contacted in vitro, such as where one or more biological samples (e.g., blood, serum, cells, tissue) are arrayed on a substrate under tissue culture conditions known by those in the art to preserve the viability of the tissue and then the fusion protein is added to the tissue culture. In a preferred embodiment of the methods of the invention the tissue is mammalian tissue, in particular human tissue.

The methods of the invention can also be practiced in vivo wherein the biological sample and the light-generating fusion protein are contacted by administration of the fusion protein (or a vector encoding the same) to a subject suspected of containing ischemic tissue under conditions to allow detection of the fusion protein in ischemic tissue present in the subject. The invention thus also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the invention relates to diagnostic assays for determining the presence of ischemic tissue in a biological sample to thereby determine whether an individual is afflicted with a disease or disorder, or is at risk of developing a disorder, associated with hypoxic conditions. The invention also provides for prognostic (or predictive) assays for determining whether an individual is at risk of developing conditions arising from ischemia.

Referring now to the Drawings, FIG. 1A is a schematic representation of different fusion proteins of the present invention. "T" indicates the enzyme target site on the fusion protein, "E" indicates the enzyme, "X" indicates the modification site on the fusion protein, and "R" indicates the reporter domain of the fusion protein. The modification at "X" by "E" results in the fusion protein becoming active or inactive "On/Off". FIG. 1B shows an embodiment wherein the "T" and the "X" are separate domains and are in cis on the fusion protein. FIG. IC shows an embodiment of the invention wherein the "T" and the "X" of the fusion protein are congruent within a domain of the fusion protein. FIG. ID shows an embodiment of the invention wherein the "T" is on a protein associated with the fusion protein containing the "X".

Figure 2B:
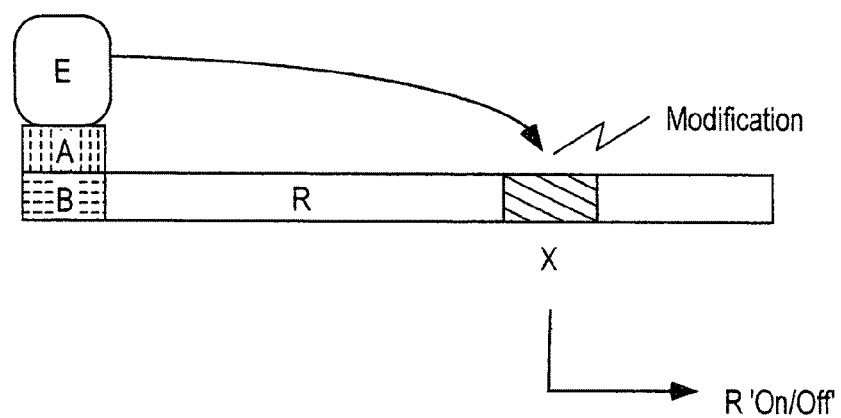
Figures 1, 14A:
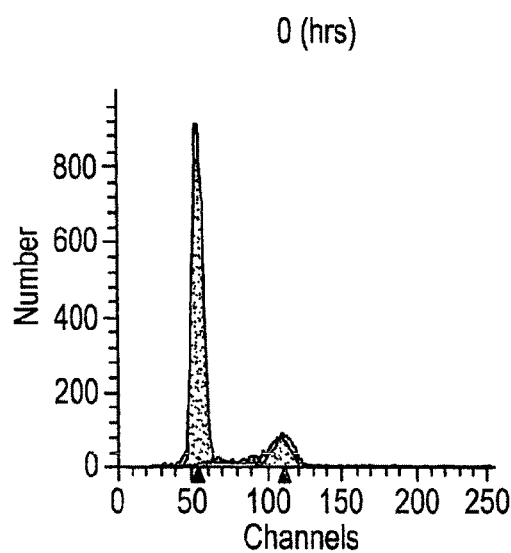
Figures 2, 14A:
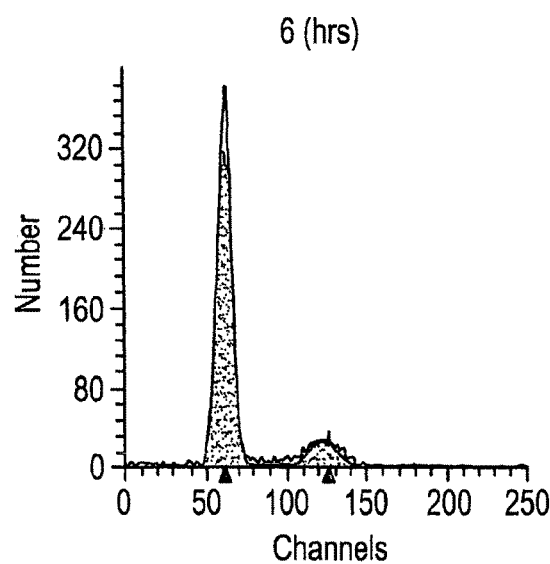

FIG. 2 is a schematic representation of different fusion proteins of the present invention. FIG. 2A is a schematic representation of a fusion protein and associated protein of the present invention in which a fusion protein and an associated protein "A" contains a known homo- or hetero-dimerization domain "HD" corresponding to the enzyme target site of an enzyme, where binding of the enzyme-associated "A" to the HD on the fusion protein results in modification of the fusion protein at "X". FIG. 2B is a related aspect of the invention in which a binding domain of a protein "A" containing an enzyme target site "T" interacts with a binding domain "B" of a fusion protein, which results in enzyme "E" modifying the reporter domain "R" of fusion protein "B" at modification site "X" such that the fusion protein does or does not emit light or cause light to be emitted.

Figures 3, 14A:
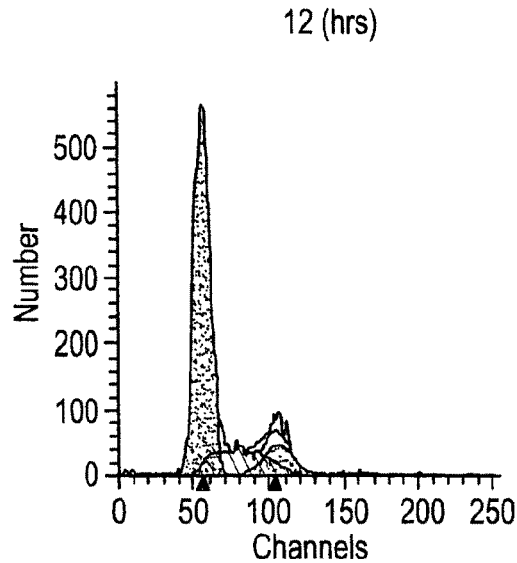
FIG. 3 shows pVHL binding to a modified form of HIF.

FIG. 3 shows pVHL binding to a modified form of HIF. (A) shows pVHL-defective renal carcinoma cells treated with increasing amounts of desferoxamine (2, 10, 100, 1000 μm) or cobalt choloride (2, 10, 100, 1000 μm) and immunoprecipitated with control (lane 1) or anti-HIF2α antibody. Bound proteins were detected by anti-HIF2α immunoblot (IB) or by farwestern (FW) analysis with purified pVHL/elongin B/elongin C (VBC) complexes. (B) shows VBC farwestern and anti-HIF2α immunoblot analysis of ts20 cells grown at the restrictive temperature under hypoxic or normoxic conditions. (C and D) depict GST-HIF1α(530-652), containing the oxygen-dependent degradation domain (ODD), produced in $E.$ $Coli$, recovered on glutathione Sepharose, and incubated with rabbit reticulocyte lysate for 90 min at 30° C. In (D, lane 3), the reticulocyte lysate was first heat inactivated for 20 min. Following stringent washes the GST-ODD protein was subjected to VBC farwestern and anti-GST immunoblot analysis.

Figures 4, 14A:
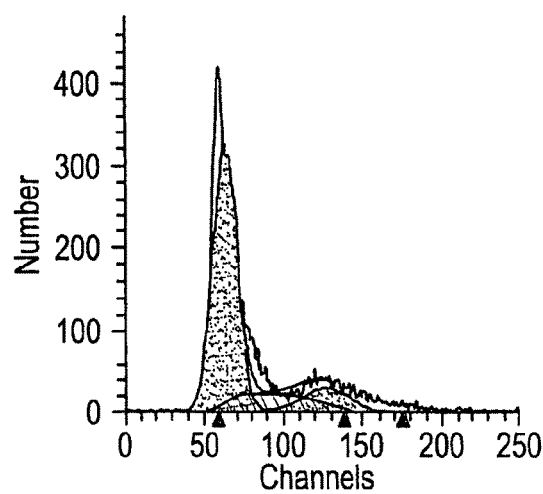

FIG. 4 shows pVHL binding to a HIF1α-derived peptide if Leu562 and Pro564 are intact. (A) shows binding of the indicated $^{35}$S-labeled Gal4-HIF1α fusion proteins to immobilized GST-pVHL, elongin B, elongin C complexes. (B) shows binding of $^{35}$S-labeled pVHL to biotinylated HIF1α (556-575) peptides with the indicated substitutions of residues 561-568. '+' indicates preincubation of peptide with unprogrammed reticulocyte lysate prior to addition of pVHL. (C and D) depict $^{35}$S-labeled wild-type (WT), Pro564Ala, and Leu562Ala full-length HA-HIF1α (panel C) and Gal4-HA-HIF1α(530-652) (panel D) proteins immunoprecipitated with anti-HA antibody or captured with immobilized GST-VBC complexes. WG=wheat germ extract; Retic=rabbit reticulocyte lysate.

Figures 5, 14A:
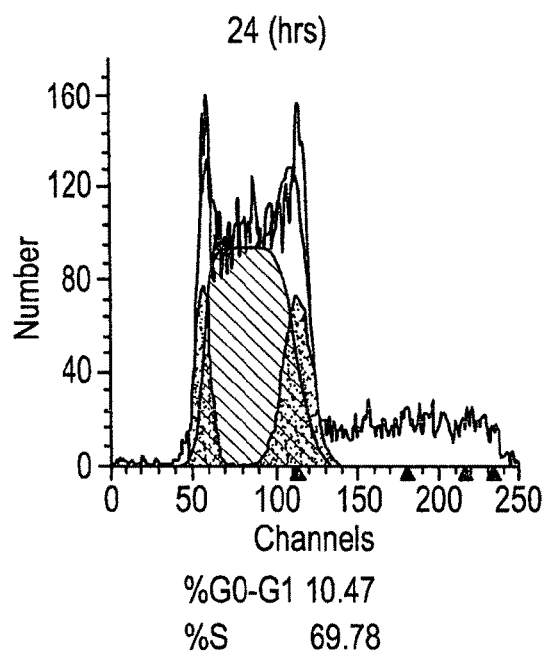

FIG. 5 shows ubiquitination and degradation of HIF linked to Leu562 and Pro 564. (A) depicts in vitro ubiquitination of $^{35}$S-labeled wild-type, Leu562A, and Pro564A Gal4-HA-HIF1α(530-652) in the presence of S100 extracts prepared from pVHL-defective renal carcinoma cells stably transfected to produce wild-type pVHL or with empty vector. (B) shows in vitro degradation of $^{35}$S-labeled wild-type, Leu562Ala, and Pro564Ala in xenopus egg extracts. (C) is an anti-HA immunoblot analysis of COS7 cells transiently transfected with 1.5 or 3.5 μg of plasmids encoding wild-type or P564A HA-HIF1α in the absence or presence of desferoxamine.

Figures 6, 14A:
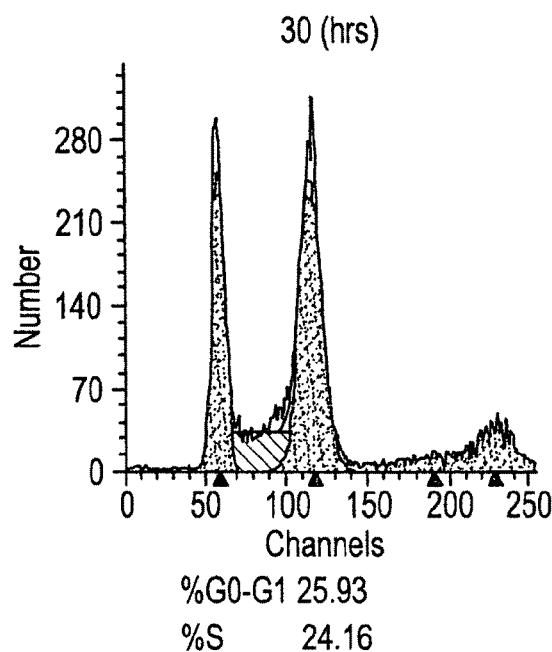

FIG. 6 depicts proline hydroxylation linked to pVHL-binding. (A) is a MALDI-TOF analysis of wild-type, Pro564Ala, and Leu562Ala biotinylated HIF(556-575) peptides following incubation with rabbit reticulocyte lysate. (B) shows Gal4-HA-HIF (555-575) translated in vitro in the presence of 3H-Proline with rabbit reticulocyte lysate or wheat germ extract and gel-band purified. Following acid hydrolysis proline and hydroxyproline were separated using thin layer chromatography. The dashed circle indicates positions of ninhydrin stained proline and hydroxyproline markers.

Figures 7, 14A:
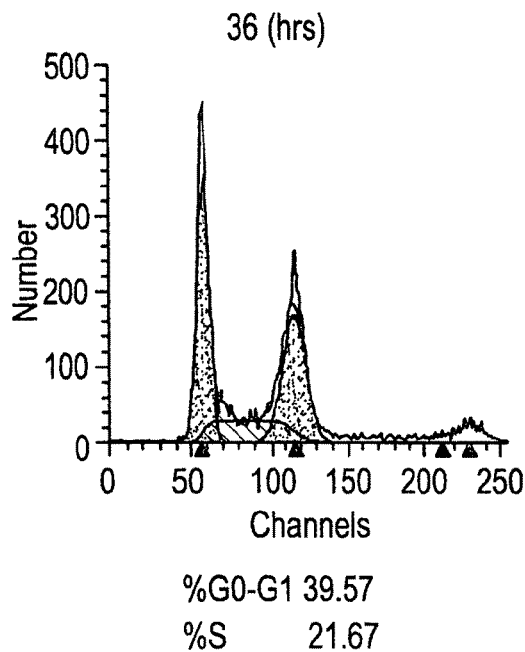

FIG. 7 illustrates that pVHL specifically recognizes HIF1α with hydroxylated proline 564. (A and B) shows binding of $^{35}$S-labeled pVHL to biotinylated HIF1α(556-575) peptides with the indicated substitutions of residues 561-568. (C) shows ts20 cells stably transfected to produce HA-pVHL grown at restrictive (lane 1) or permissive (lanes 2-6) temperature and immunoprecipitated anti-HIF1α (lane 1 and 2) or anti-HA antibody (lanes 3-7). Bound proteins were eluted by boiling in sample buffer (lane 1 and 2) or treatment with the indicated peptides and then immunoblotted with anti-HIF1α antibody. (D) shows pVHL-defective renal carcinoma cells stably transfected to produce wild-type pVHL (WT8) or with empty vector (RC3) metabolically labeled with $^{35}$S methionine, lysed, and incubated with immobilized biotinylated HIF1α(556-575) peptides with the indicated substitutions of residue 564. Specifically bound proteins were detected by autoradiography.

FIG. 8 illustrates the production of TETr-cyclins A and E. (A) is a schematic of TETr-cyclin fusion protein. (B) shows production of TETr-cyclin A and TETr-cyclin E. Cells transfected to produce the indicated cyclin A or cyclin E proteins were lysed and immunoblotted (IB) with the indicated antibodies. (C) shows phosphorylation of pRB by TETr-cyclins A and E in SAOS-2 cells. pRB-defective SAOS-2 cells transfected so as to produce HA-tagged pRB along with the indicated cyclins were lysed and immunoblotted with anti-HA antibody. The % of transfected cells in G1 and S phase was determined by fluorescence activated cell sorting (FACS).

FIG. 9 shows DNA bound cyclins A and E differentially affecting transcription. (A) is a schematic of reporter plasmid (pUHC 13-3) that contains seven TETracycline operator sequences (TETo) upstream of a minimal CMV promoter that includes a TATA box. (B, C) show U2OS cells were cotransfected with plasmids encoding the indicated TETr fusion proteins along with the pUHC 13-3 reporter plasmid and a plasmid encoding β-galactosidase. Numbers shown at the bottom of the graph indicate the amount of TETr plasmid (in μg). 48 hours later luciferase activity, normalized for β-galactosidase, was determined. Fold repression is the corrected luciferase value for TETr alone divided by the corrected luciferase values for the indicated TETr fusion proteins. Fold activation represents the corrected luciferase values for the indicated TETr fusion proteins divided by the corrected luciferase value for TETr alone.

FIG. 10 illustrates transcriptional regulation by cyclins A and E dependent upon DNA binding. (A) shows U2OS cells cotransfected with plasmids encoding the indicated TETr fusion proteins along with the pUHC 13-3 reporter plasmid and a plasmid encoding β-galactosidase. 24 hours later doxycycline was added to a final concentration of 2 μg/ml where indicated by a '+'. 24 hours later, luciferase activity, corrected for β-galactosidase activity, was determined and expressed as fold repression or activation relative to cells producing TETr alone. (B) shows U2OS cells cotransfected with plasmids encoding the indicated cyclins along with the pUHC 13-3 reporter plasmid and a plasmid encoding β-galactosidase. Fold repression and activation was determined as in (A). (C) shows U2OS cells cotransfected with plasmids encoding TETr or TETr-cyclin E, along with a minimal HSV-TK promoter reporter plasmid containing the indicated number of TETo binding sites and a plasmid encoding β-galactosidase. Doxycycline was added as in (A).

FIG. 11 illustrates that cyclin box is required for transcriptional repression by DNA bound cyclin A. (A) U2OS cells were cotransfected with plasmids encoding the indicated TETr-cyclin A variants along with the pUHC 13-3 reporter plasmid and a plasmid encoding β-galactosidase. Cell extracts were prepared and luciferase activity, corrected for β-galactosidase activity, was expressed as fold repression relative to cells producing TETr alone. (B) The indicated TETr-cyclin A variants were translated in vitro in the presence of $^{35}$S-methionine and incubated with GST-cdk2 and glutathione Sepharose. Specifically bound proteins were resolved by SDS-polyacrylamide gel electrophoresis and detected by autoradiography. In parallel, 20% of the input proteins were resolved by SDS-polyacrylamide gel electrophoresis and detected by autoradiography. (c) pRB defective SAOS-2 cells transfected so as to produce HA-tagged pRB along with the indicated TETr-cyclin A variants were lysed and immunoblotted with anti-HA antibody.

FIG. 12 shows transcriptional activation by cyclin E linked to its ability to bind to cdk2 and interact with substrates. (A) U2OS cells were cotransfected with plasmids encoding the indicated TETr-cyclin E variants along with the pUHC 13-3 reporter plasmid and a plasmid encoding β-galactosidase. Cell extracts were prepared, and luciferase activity, corrected for β-galactosidase activity, was expressed as fold activation relative to cells producing TETr alone. (B) The indicated TETr-cyclin E variants were translated in vitro in the presence of $^{35}$S-methionine and incubated with GST-cdk2 and glutathione Sepharose. Specifically bound proteins were resolved by SDS-polyacrylamide gel electrophoresis and detected by autoradiography. In parallel, 20% of the input proteins were resolved by SDS-polyacrylamide gel electrophoresis and detected by autoradiography. (c) pRB defective SAOS-2 cells transfected so as to produce HA-tagged pRB along with the indicated TETr-cyclin E variants were lysed and immunoblotted with anti-HA antibody.

FIG. 13 shows transcriptional activation by DNA bound cyclin E dependent on cdk2 catalytic activity. (A, B) U2OS cells were transiently cotransfected with plasmids encoding TETr-cyclin A or E and, where indicated, increasing amounts of a plasmid encoding a dominant-negative (dn) form of cdk2. Cell extracts were prepared and luciferase activity, corrected for β-galactosidase activity, was determined. Corrected luciferase values were expressed as fold repression (A) or activation (B) relative to TETr alone. (C) U2OS cells were transiently transfected with plasmids encoding TETr-cdk2 or TETr-cdk2 (N132A) and a plasmid encoding either cyclin A or E. Cell extracts were prepared and luciferase activity, corrected for β-galactosidase activity, was determined. Corrected luciferase values were expressed as fold activation relative to TETr alone.

FIG. 14 shows transcriptional effects mediated by cell-cycle dependent changes in endogenous cyclins E and A. (A,B) 3T3 cells stably transfected with a luciferase reporter plasmid containing 7 TETo sites (pUHC13-3) and a plasmid encoding TETr-cdk2 were serum-starved for 72 hours and subsequently re-fed with serum. At various timepoints thereafter aliquots of cells were removed and either lysed for immunoblot analysis with the indicated antibodies or analyzed for DNA content by propidium iodide staining followed by fluorescence activated cell sorting (FACS). (C) 3T3 cells stably transfected with a luciferase reporter plasmid containing 7 TETo sites (pUHC13-3) in the absence (open circles) or presence of a plasmid encoding TETr-cdk2 (closed squares) or TETr-cdk2 (N132A) (open squares) were serum-starved for 72 hours and then re-fed with serum in the presence or absence of doxycycline. At various timepoints thereafter luciferase assays were performed. To correct for general effects due to serum, the luciferase values at each timepoint in the absence of doxycycline were corrected by subtracting the luciferase assay obtained in the presence of doxycycline. After correction, the luciferase values for the two cell populations were expressed relative to the corresponding luciferase values obtained at time 0. In parallel, the cells producing TETr-cdk2 were lysed and immunoprecipitated with anti-cyclin A or anti-is cyclin E antibodies. The immunoprecipitates were then used to phosphorylate Histone H1 in vitro.

Methods of Treating Hypoxia or Ischemia Related Tissue Damage and Modulating Angiogenesis or Vascularization. Tissue ischemia is a major cause of morbidity and mortality. In principle, drugs that stabilize HIF may augment angiogenesis and the adaptation of hypoxia. The activation of HIF by hypoxia is complex and involves protein stability, nuclear localization, DNA binding capability and transcriptional activation function. The discovery that proline hydroxlaytion governs HIF turnover in the presence of oxygen will facilitate the dissection of the mechanism underlying the various aspects of HIF regulation.

The invention also provides various methods of treating, i.e., reducing, preventing or delaying the onset of HIF-1 related disorders, modulating angiogenesis or vascularization. Examples of HIF-1 mediated disorders include chronic and acute hypoxia or ischemia related disorders such as tissue damage and scarring. Acute hypoxia or ischemia related disorders include for example myocardial infarction, stroke, cancer and diabetes such as tissue damage and scarring. Chronic hypoxia or ischemia related disorders include for example, deep vein thrombosis, pulmonary embolus and renal failure.

In one aspect the invention the invention provides methods of treating or preventing a hypoxic or ischemic related disorder or modulating angiogenesis or vascularization by administering to a subject a compound that decreases prolyl hydroxylase, expression or activity. Examples of prolyl hydroxylase includes human Egl-9 or homologs. (Epstein, et al Cell 107:43-54, 2001) The compound can be a prolyl hydroxylase antibody, a nucleic acid that decreases the expression of a nucleic acid that encodes a prolyl hydroxylase polypeptides such as a prolyl hydroxylase anti-sense nucleic acid or a compound identified by any of the methods of the invention. Preferably, the half life of HIF in the subject is increased in the presence of the compound as compared to the absence of the compound.

In a further aspect the invention includes a method of treating cancer in a subject by administering to the subject a compound that increases prolyl hydroxylase expression or activity. Preferably, the compound is a compound that has been identified by the methods of the invention.

In another aspect the invention provides a method for treating or preventing a hypoxia or ischemic related disorder in a subject by administering to a subject a compound that which modulates prolyl hydroxylation of HIF.

In still a further aspect the invention provides a method for treating or preventing a HIF related disorder by administering to a subject a compound that which modulates prolyl hydroxylation of HIF such that the HIF related disorder is prevented reversed of stabilized.

In yet another aspect the invention provides a method for regulating HIF turnover in a subject by administering to a subject a compound that which modulates prolyl hydroxylation.

By "modulates" is meant to increase or decrease the prolyl hydroxylation of HIF. Compounds that inhibits prolyl hydroxylation include several small molecule proline hydroxylase inhibitors which have been developed as antifibrotic agents.

The subject is preferably a mammal. The mammal can be, e.g., a human, non-human primate, mouse, rat, dog, cat, horse, or cow. In various aspects the subject include patients with coronary, cerebral, or peripheral arterial disease and patients with one or more non-healing wounds.

EXAMPLES

Example 1

Characterization of Hypoxia-Responsive Polypeptides

Figure 4A:
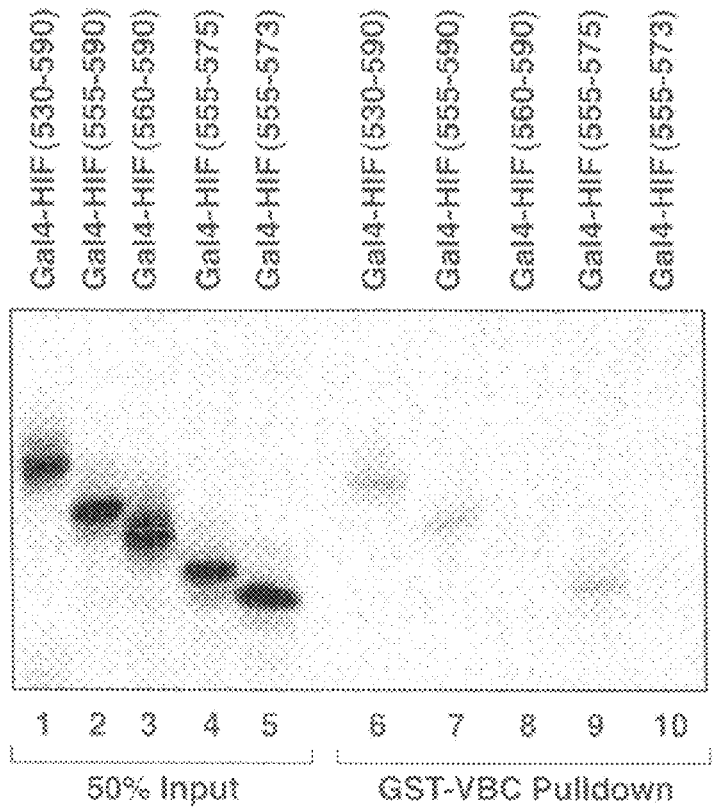
FIG. 4 shows pVHL binding to a HIF1α-derived peptide if Leu562 and Pro564 are intact.
Figure 4B:
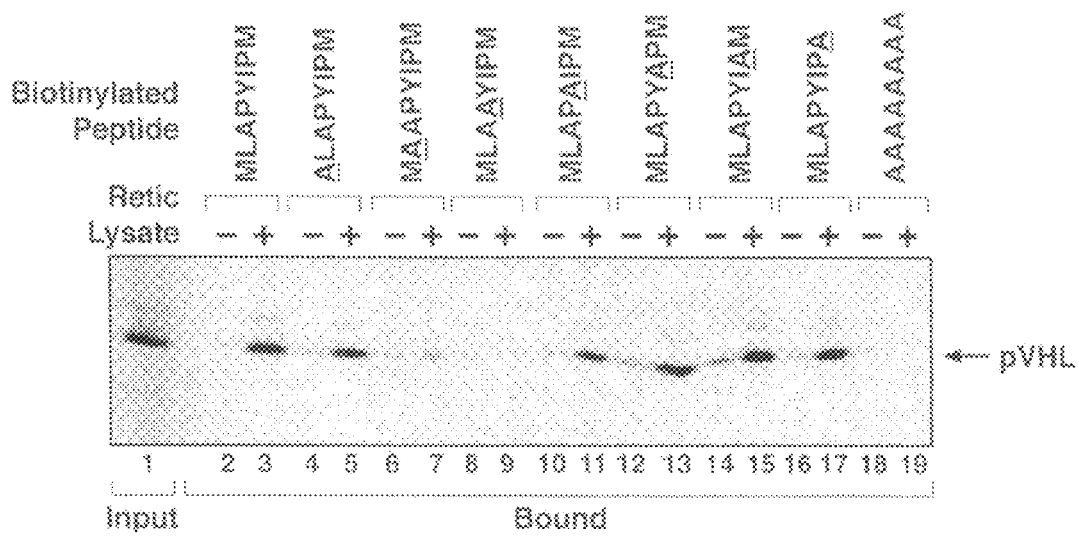

In order to demonstrate the efficacy of the First embodiment of the invention, e.g. employing a hypoxia-responsive LGP, the interaction of pVHL and HIF was examined. A HIF1α polypeptide that is sufficient to bind pVHL is disclosed herein. pVHL binds directly to a region of HIF1α called the oxygen-dependent degradation domain (ODD). pVHL recognizes HIF produced in rabbit reticulocyte lysate but not HIF produced in wheat germ extracts or in E. Coli. Furthermore, wheat germ or E. Coli-derived HIF binds to pVHL following preincubation with a human, rabbit, or xenopus cell extracts at 37° C. For example, glutathione S-transferase-ODD fusion proteins produced in E. Coli were not recognized by VBC in far western assays (FIG. 3C). These proteins were recognized, however, after pre-incubation with a rabbit reticulocyte lysate. Similar results were obtained with GST-ODD fusion proteins of various sizes, thus excluding the possibility that the farwestern blot signal represents a spurious interaction between VBC and a reticulocyte-derived protein. VBC did not recognize GST-ODD fusion proteins incubated with a heat-inactivated reticulocyte lysate (FIG. 3D). Gal4-HIF fusion proteins containing HIF residues 555-575 bound specifically to immobilized GST-VHL, elongin B, elongin C complexes (FIG. 4A). Coupled in vitro transcription/translation of $^{35}$S-labeled proteins was conducted according to the manufacturer's instructions (TNT, Promega). Also, a biotinylated peptide corresponding to HIF residues 556-575 bound to pVHL following pre-incubation with reticulocyte lysate (FIG. 4B). For peptide binding studies, 1 μg of biotinylated peptide was bound to 30 μl of monomeric avidin Sepharose (Pierce). Where indicated, the peptide was pre-incubated with 50 μl of rabbit reticulocyte lysate for 90 min at 30° C. The Sepharose was then washed 3 times with NETN (20 mM Tris pH 8.0, 100 mM NaCl, 1 mM EDTA, 0.5% non-idet P40) and used in binding reactions containing 4 μl $^{35}$S-HA-pVHL in 500 μl of EBC or 500 μl $^{35}$S-radiolabeled cell extract (equivalent to cells from a subconfluent 100 mm dish). Following 1 hour incubation at 4° C. with rocking the Sepharose was washed 4 times with NETN. Bound proteins were eluted by boiling in SDS-containing sample buffer and detected by autoradiography. This region of HIF contains a highly conserved 8 mer (MLAPYIPM) which, when mutated to 8 consecutive alanines, leads to HIF stabilization in cells. An alanine scan of this region showed that Leu562 and Pro564 were essential for specific binding to pVHL in this assay (FIG. 4B). In contrast, mutation of the one potential phosphoacceptor in this peptide, Tyr565, did not affect pVHL binding, in keeping with an earlier study in which a Tyr565Phe mutation did not affect HIF stability. In addition, the binding of pVHL to GST-ODD in the assays described above was unaffected by phosphatase treatment.

Binding of pVHL to HIF1α is critically dependent upon residues Leu562 or Pro564 of HIF1α. Importantly, mutation of either Leu562 or Pro564 in the context of full-length HIF1α or a Gal4-ODD fusion protein also led to a loss of pVHL binding activity (FIGS. 4C and 4D, respectively). Gal4-ODD made with reticulocyte lysate contained an electrophoretically distinct band compared with Gal4-ODD made with wheat germ extract (FIG. 4D). This electrophoretically distinct protein bound to VBC and was undetectable among the Leu562Ala and Pro564Ala translation products. The isoelectric points of the two arrowed bands in FIG. 4D were identical following 2-D gel electrophoresis indicating that the putative modification did not involve a change in protein charge.

Figure 5A:
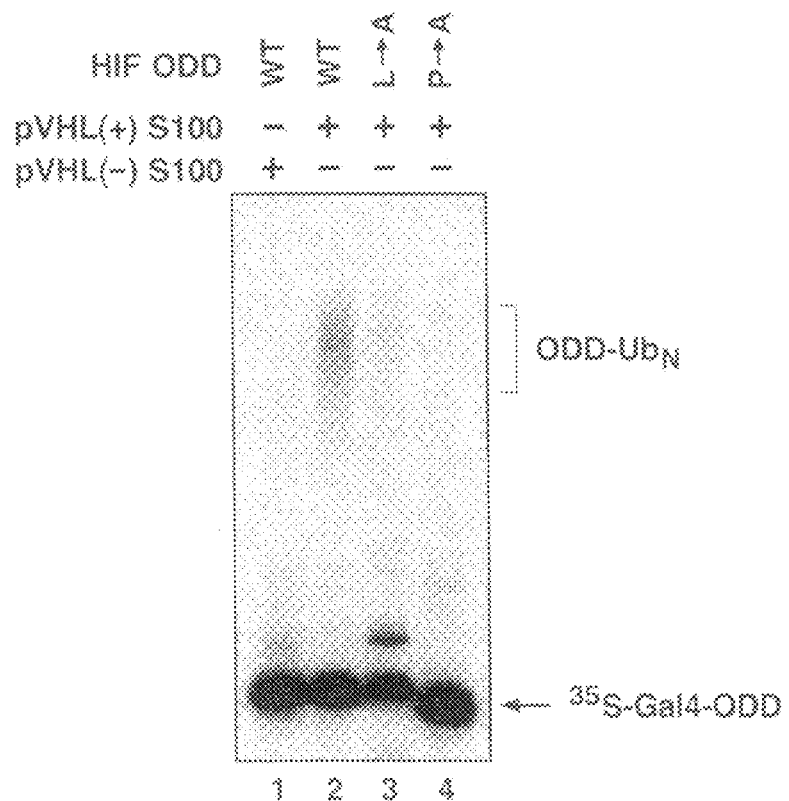
FIG. 5 shows ubiquitination and degradation of HIF linked to Leu562 and Pro 564.
Figure 5B:
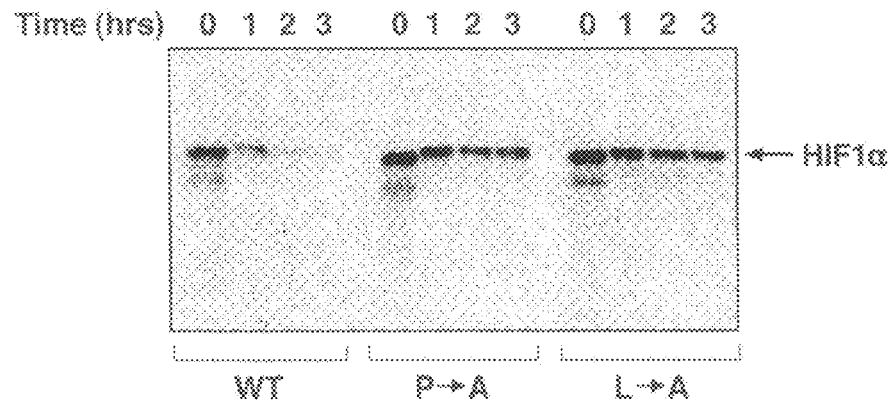
Figure 6A:
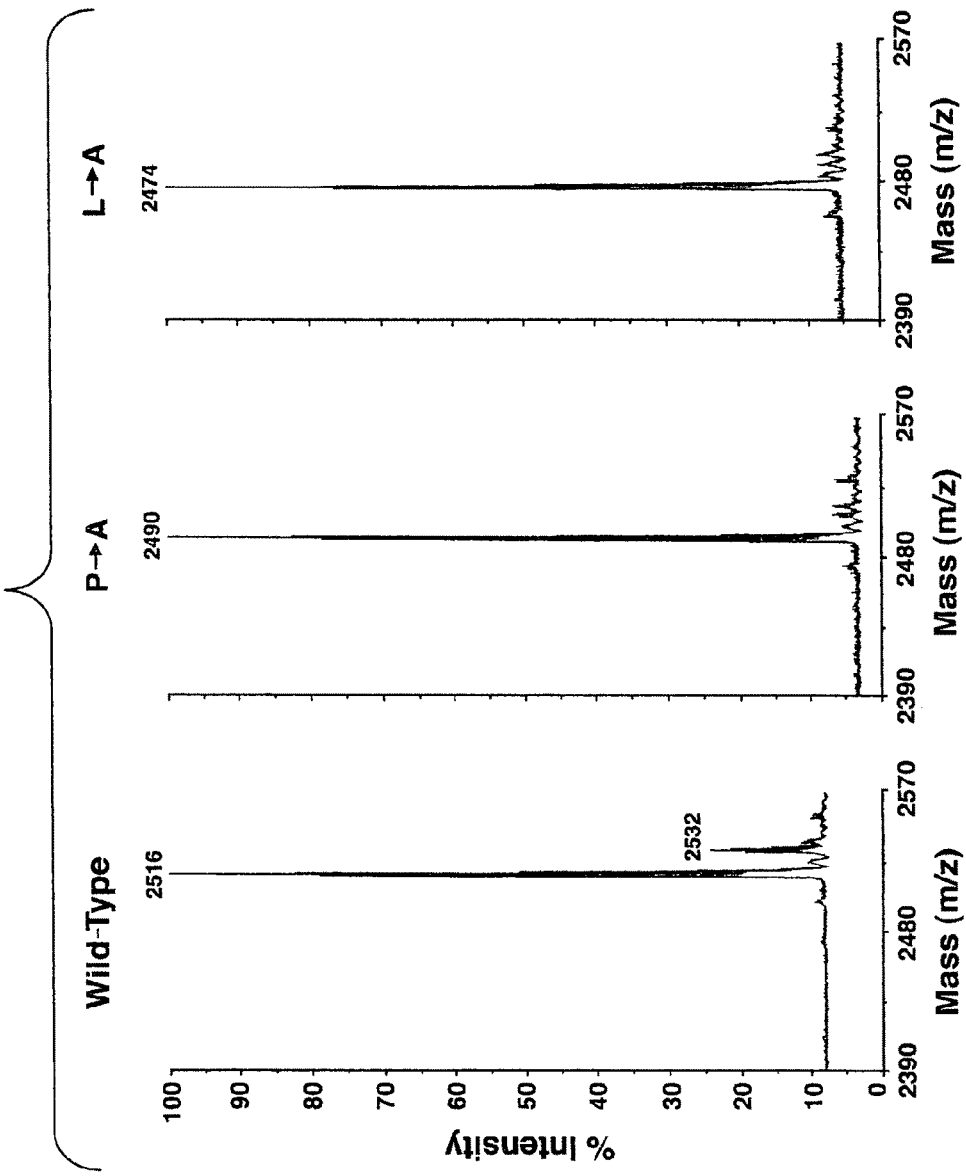
FIG. 6 depicts proline hydroxylation linked to pVHL-binding.
Figure 6D:
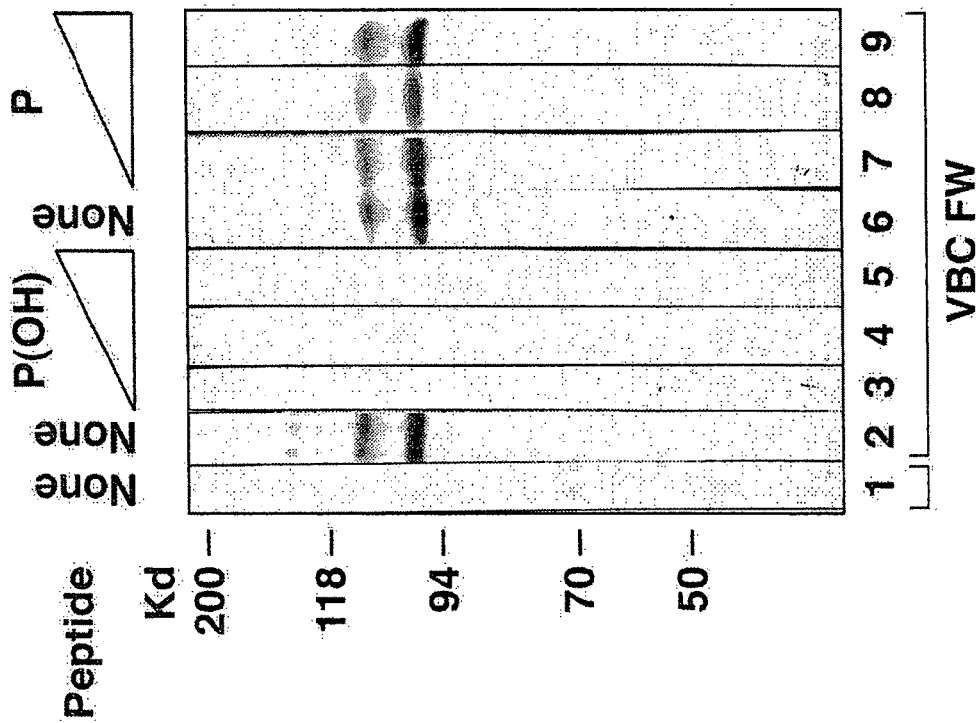
Figure 6C:
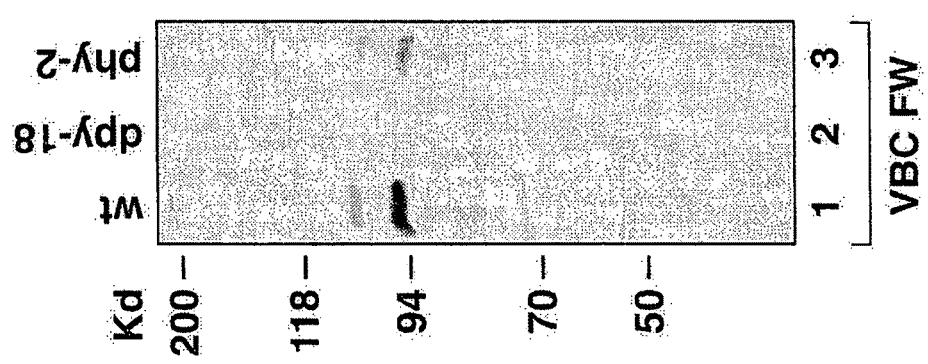
Figure 7D:
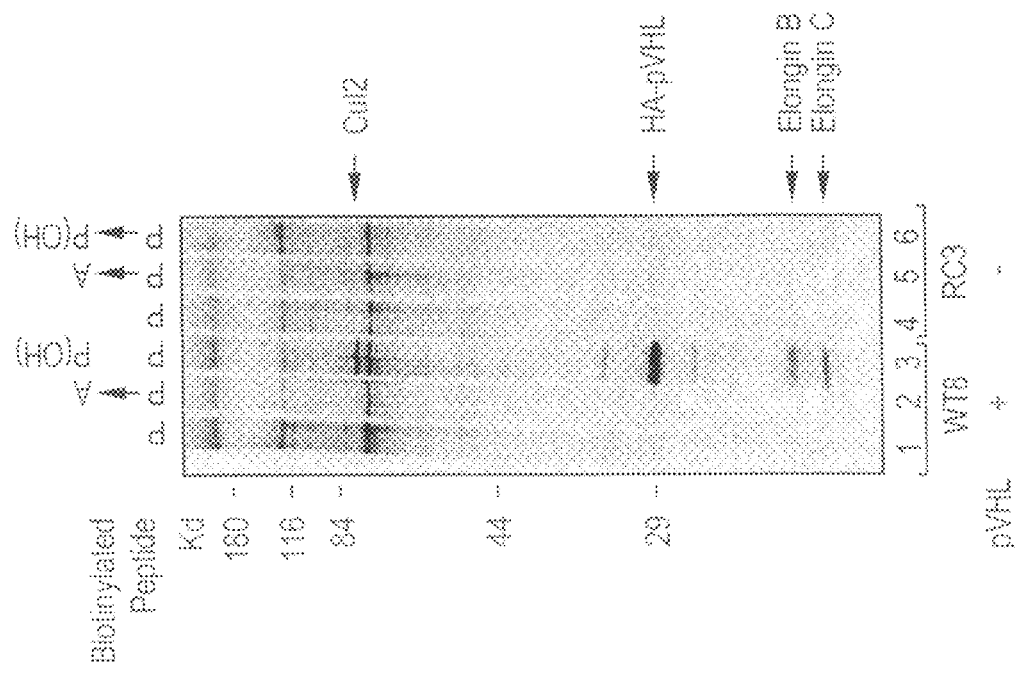
FIG. 7 illustrates pVHL specifically recognizing HIF1α with hydroxylated proline 564.
Figure 7C:
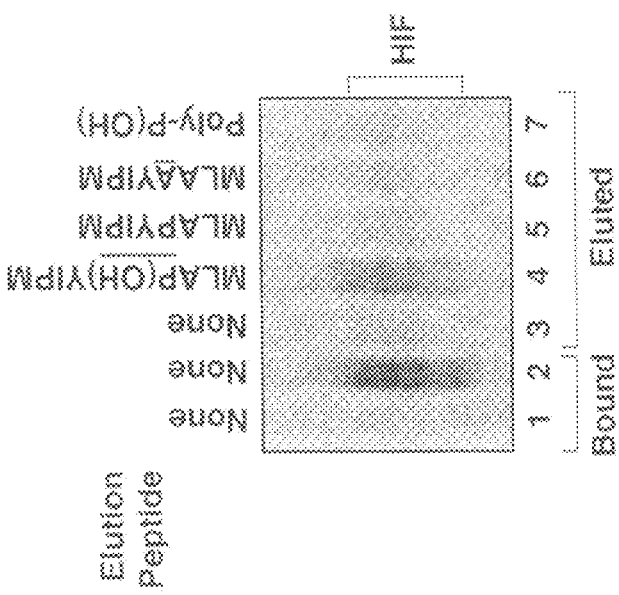

Modification of HIF1α by pVHL following binding is also critically dependent upon residues Leu562 or Pro564 of HIF1. Gal4-HIF fusion proteins with the Leu562Ala mutation or Pro564Ala mutation displayed diminished pVHL-dependent polyubiquitination in vitro relative to the corresponding wild-type protein (FIG. 5A). Qualitatively similar results were obtained with the corresponding full-length HIF1α species, although this assay is less robust than with the Gal4-ODD fusion proteins. Likewise, HIF1α Pro564Ala and HIF1α Leu562Ala were far more stable than wild-type HIF1α in in vitro degradation assays performed with xenopus extracts (FIG. 5B). Xenopus egg extracts were made as is well known in the art and stored frozen until use. Degradation reactions contained 0.8 μl of egg extract, 0.1 μl of 100 mg/ml cyclohexamide, 0.25 μl of energy regeneration mix, 0.25 μl of bovine ubiquitin, and 0.4 μl of $^{35}$S-radiolabeled HIF and were carried out at room temperature. At the indicated timepoints 1 μl aliquots were removed and placed in sample buffer. Samples were resolved on 5-15% gradient gels and analyzed by autoradiography. Biotinylated HIF (556-575) peptides were incubated with rabbit reticulocyte lysate, washed, eluted with free biotin, and analyzed by mass spectrometry. 1 μg of HPLC-purified peptide was bound to 30 μl monomeric avidin Sepharose and incubated with 100 μl of rabbit reticulocyte lysate at room temperature for 1 hour with tumbling. Following brief centrifugation the reticulocyte lysate was removed, fresh reticulocyte lysate was added, and the cycle was repeated 6 times. The Sepharose was then washed 4 times with NETN and once with PBS. The modified peptide was eluted in 50 μl of 20 mM ammonium acetate [pH 7.0], 2 mM biotin. In these experiments Met561 and Met568 were converted to alanine to prevent spurious oxidation of the methionine residues during analysis. This double alanine substitution, like the corresponding single substitutions, did not affect pVHL binding. Treatment of the HIF (556-575) peptide with rabbit reticulocyte lysate led to the appearance of a second peak in MALDI-TOF assays representing an increase in molecular weight of 16 (FIG. 6A). This peak was not detectable prior to incubation with reticulocyte lysate and was not detected in the corresponding reticulocyte-treated Leu562Ala and Pro564Ala peptides (FIG. 6A). Postsource decay analysis using the same instrument placed the addition of +16 at Pro 564. Similarly, electrospray ion trap mass spectrometry/mass spectrometry (MS/MS) analysis was consistent with addition of +16 at Pro 564 and excluded such a modification of Leu 562. Finally, MS/MS analysis of the reticulocyte-treated HIF (556-575) peptide produced a pattern of ions that was identical to the pattern obtained with a HIF (556-575) peptide which was synthesized to contain hydroxyproline at position 564. Next, Gal4-HIF(555-575) was translated in vitro in the presence of $^3$H-Proline using rabbit reticulocyte lysate or wheat germ extract, gel-band purified, and subjected to acid hydrolysis and thin layer chromatography. 2 ml of $^3$H-P-labeled Gal4-HIF (555-575) in vitro translate was immunoprecipitated with 50 μg of anti-HA antibody (12CA5, Roche), resolved on a 12% SDS-polyacrylamide gel, and transferred to a PVDF membrane. Gal4-HIF (555-575) was visualized by autoradiography and the corresponding region of PVDF was excised, hydrolyzed by incubation in 100 μl of 10 N HCl at 105° C. for 3 hours. Samples were evaporated to dryness, resuspended in 20 μl H$_2$O containing 10 μg of unlabeled proline and 4-OH proline (Sigma), and resolved by 2-D thin layer chromatography using phenol-distilled H$_2$O in the first dimension and N-butanol-acetic acid-H$_2$O in the second. Following visualization of standards with ninhydrin radiolabeled proline was detected by autoradiography. Gal4-HIF produced in rabbit reticulocyte lysate, but not in wheat germ, contained hydroxyproline (FIG. 6B).

pVHL specifically recognizes a proline hydroxylated determinant. The HIF (556-575) peptide containing hydroxyproline at position 564 bound to pVHL with or without pretreatment with reticulocyte lysate (FIG. 7A). The mass spectrometry analysis of the Leu562Ala peptide showed that Leu562 was required for HIF modification (FIG. 6A). Indeed, pVHL bound to a HIF (556-575) peptide with the Leu562Ala substitution and hydroxyproline at residue 564 (FIG. 7B). This suggests that the primary role of Leu562 is to allow for the hydroxylation of Pro 564. Two approaches were used to demonstrate that hydroxylated HIF peptide could interact with cell-derived pVHL complexes. Ts20 cells were engineered to produce HA-tagged pVHL which carry a temperature-sensitive mutation in the E1-ubiquitin activating enzyme. ts20 cells were transfected with pIRES-HA-VHL, pIRES-HA-VHL (Y98H), or pIRES-Neo (Invitrogen) and selected in the presence of 1 mg/ml G418. Individual G418-resistant colonies were isolated using cloning cylinders and expanded. Cells producing HA-VHL or HA-VHL (Y98H) were identified by anti-HA immunoblot analysis. HIF coimmunoprecipitated with HA-pVHL at the restrictive temperature. HIF bound to pVHL in this way could be eluted by the hydroxylated HIF (556-575) peptide but not the unmodified peptide (FIG. 7C). For the tests shown in FIG. 7C, ts20 cells were grown at the restrictive or permissive temperature for 14 hours, methionine-starved for 90 min, and then grown in the methionine-free media supplemented with $^{35}$S-met (500 mCi/ml) for 90 min. Cells were washed once with cold PBS, lysed in EBC, and immunoprecipitated with anti-HA (12CA5; Roche or anti-HIFPIx (NB100-105; Novus). Following 5 washes with NETN bound proteins were eluted by boiling in sample buffer or by incubation in 65 μl of PBS containing 7 μg of the indicated peptide. Moreover, HIF was not eluted by the HIF (556-575) Pro564Ala peptide or by a poly-hydroxyproline peptide (FIG. 7C). Affinity chromatography was performed with immobilized peptides and metabolically labeled matched renal carcinoma cells which do (WT8) or do not (RC3) produce HA-pVHL. 786-0 subclones were starved for 1 hour, grown in the methionine-free media supplemented with $^{35}$S-met (500 mCi/ml) for 3 hr, washed once with ice cold PBS, and lysed in EBC. The proline hydroxylated HIF (556-575) peptide specifically bound to pVHL as well as proteins with the expected electrophoretic mobilities of the pVHL-associated proteins elongin B, elongin C, and Cul2 (FIG. 7D). The identity of pVHL in this experiment was confirmed by western blot analysis. Likewise, the binding of endogenous pVHL to the hydroxylated peptide was detected using 293 embryonic kidney cells. A HIF1α mutant in which Proline 564 was converted to alanine was stabilized in cells and insensitive to the hypoxia-mimetic desferoxamine (FIG. 5C).

The HIF1α protein is stabilized in hypoxic conditions and functions to inhibit, decrease and/or reverse hypoxia in affected tissues, e.g. in a solid tumor, diabetic retinopathy or ischemic heart tissue, in part by modulating pro-angiogenic factors. A light-generating fusion protein containing a HIF1α moiety will also be stabilized in hypoxic tissue. Destruction of a HIF1α protein or a HIF1α-containing LGP via the pVHL ubiquitin pathway occurs, e.g. during normoxia, when a prolyl hydroxylase modifies the HIF1α protein such that pVHL binds to and modifies HIF1α. This modification process acts as a dynamic switch to regulate the bioluminescence of the HIF1α-containing light-generating fusion protein such as the First embodiment of the invention. A HIF1α-containing light-generating fusion protein is useful to dynamically image hypoxic tissues, e.g. cancer, in situ, and to screen for or test the efficacy of hypoxia-modulating compounds.

Example 2

The following example demonstrates the efficacy of light-generating fusion proteins of the invention for imaging hypoxic tissues.

The Oxygen-Dependent Degradation Domain (ODD) of HIF1α, renders HIF1α unstable in the presence of oxygen. This region is recognized by pVHL. pVHL specifically binds directly to peptidic determinants, corresponding to HIF1α residues 555-575, located within the ODD. At the core of this peptide there is a conserved proline residue (residue 564) which, in the presence of oxygen, becomes enzymatically hydroxylated. This residue serves as the signal for pVHL to bind. In sum, in the presence of oxygen, the HIF peptide becomes hydroxylated and is recognized by pVHL. In the absence of oxygen (hypoxia), the modification does not take place and pVHL does not bind to HIF.

Construction of ODD-LUC Plasmids

In a first set of experiments the ability of a small HIF peptide (555-575) to function in cis to target a foreign protein for pVHL-dependent proteolysis was evaluated. To this end, the HIF cDNA encoding amino acids 555-575 (hereafter 'ODD') was PCR amplified with oligonucleotides that introduced convenient restriction sites, digested, and gel-band purified. The PCR fragment was then subcloned, in-frame, 3' of a Firefly luciferase cDNA contained in the pGL3 plasmid (Promega). The resulting luciferase-ODD chimeric cDNA was subcloned into pcDNA3 (Invitrogen) to facilitate in vitro translation and expression studies in mammalian cells. In parallel a pcDNA3 plasmid encoding wild-type Firefly luciferase and pcDNA3 plasmid encoding wild-type HIF1α was used as controls.

VBC-GST Pulldown of ODD-Luciferase

To determine whether the ODD-luciferase protein could bind to pVHL, GST-VHL, elongin B, and elongin C ('GST-VBC') were produced in *E. Coli* and recovered as a trimeric complex on glutathione sepharose. Earlier work showed that pVHL does not fold properly in the absence of elongin B and elongin C. HIF1α, ODD-luciferase, and wild-type luciferase were translated in vitro using rabbit reticulocyte lysate (RRL) or wheat germ extract (WG) in the presence of $^{35}$S methionine (FIG. 15). Aliquots from the in vitro translation reactions were added to recombinant VBC-GST prebound to glutathione sepharose and incubated for 1 hour. The sepharose was then washed and bound proteins were resolved on a 12% SDS polyacrylamide gel. The gel was then dried and exposed to film. pVHL bound to reticulocyte-generated HIF1α and ODD-Luc, but not Luc (compare lanes 4, 8 and, 12). Furthermore, pVHL did not bind to wheat germ produced ODD-Luc, as wheat germ lacks the HIF prolyl hydroxylase (compare lanes 6 and 8). Thus the data show that ODD-Luc was specifically recognized by pVHL.

Peptide Competition Assay

Figure 16:
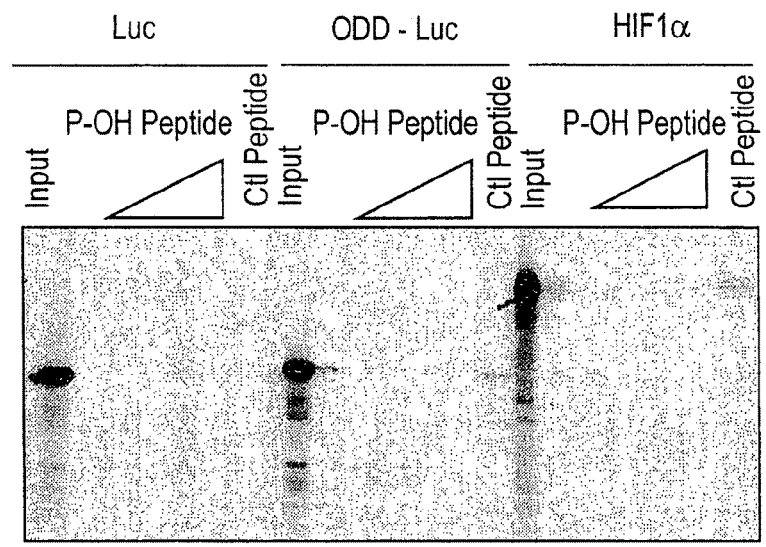

The observation that pVHL bound to ODD-Luc produced in RRL, but not WG, strongly suggested that the ODD-Luc, like HIF, needed to undergo prolyl hydroxylation in order to be recognized by pVHL. To study this further, the GST-VBC binding experiments were repeated in the presence of synthetic HIF (555-575) peptides in which Pro 564 was hydroxylated (P—OH) or was not hydroxylated (P). GST-VBC was mixed with either the control (P) peptide or the P—OH peptide in increasing concentrations (from 0-5 μg). Next in vitro translated (in retic lysate) Luc, ODD-Luc, or HIF1α was then added to see if it could efficiently compete off any bound P—OH. HIF and ODD-Luc were able to compete off the P—OH peptide effectively at even very high concentrations of P—OH. Thus, the results obtained with ODD-Luc recapitulated earlier binding studies performed with authentic HIF. (FIG. 16.)

Luciferase Activity in Cells

Figure 17:
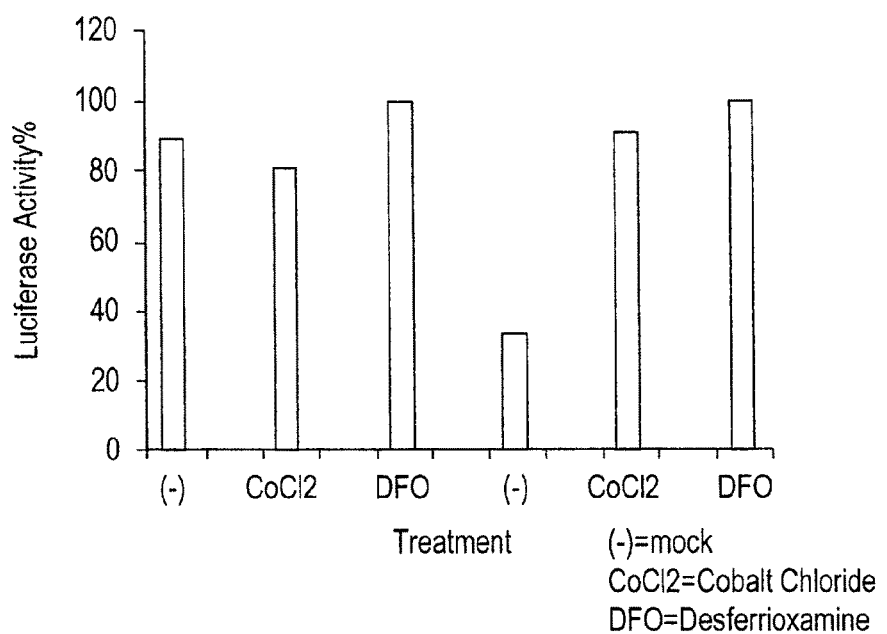

In pilot experiments, it was confirmed that ODD-Luc in vitro translate retained luciferase activity in vitro comparable to wild-type luciferase. To begin to ask whether the ODD-Luc was oxygen sensitive in cells, transient transfection assays were performed. In the first set of experiments, 100 mm tissue culture plates were seeded with 8×10$^5$ HeLa cells per plate. Eighteen hours later the cells were transiently transfected, using lipofectamine (Gibco), with the pcDNA3 plasmids encoding ODD-Luc or wild-type Luc along with an internal control plasmid encoding *Renilla* luciferase. Twenty-four hours after transfection the cells were split into 6 well plates and allowed to adhere and grow for 8-12 hours. At this point the hypoxia mimetics desferrioxamine (DFO) or cobalt chloride (CoCl2) were added directly to the media at final concentrations of 500 mM and 200 mM respectively, in duplicate wells. In addition, some wells were not treated so as to serve as controls. 12 hours after treatment with DFO and CoCl2 the cells were lysed with Passive Lysis Buffer (Promega), rocked at room temperature for 20 minutes, and assayed for Firefly and *Renilla* Luciferase according to the manufacturers instructions. Results were obtained in duplicate and averaged. (FIG. 17)

In the untreated cells the luciferase values for ODD-Luc were approximately 30% of the values obtained with wild-type Luc. Note that HeLa cells have wild-type pVHL and these experiments were conducted using cells grown in the presence of oxygen. The addition of hypoxia-mimetics led to a marked increased in ODD-Luc luciferase activity, whereas no such induction was detected with wild-type luciferase. The induced levels of ODD-luciferase were comparable to those obtained with wild-type luciferase. These results are consistent with the idea that ODD-Luc is subject to pVHL-dependent proteolysis in cells whereas wild-type Luc is not.

Imaging of ODD-Luc in Xenograft Tumors in Nude Mice.

To verify in a mammalian system that the ODD-Luc gene is indeed regulated by hypoxia or hypoxia-mimetics, the following experiment was conducted. Given the ease of subcutaneously transplanting tumors and their ability to grow and vascularize, the ability to image luciferase activity of tumors at the subcutaneous level and assess ODD-Luc's response to hypoxia was tested as follows.

Figure 18:
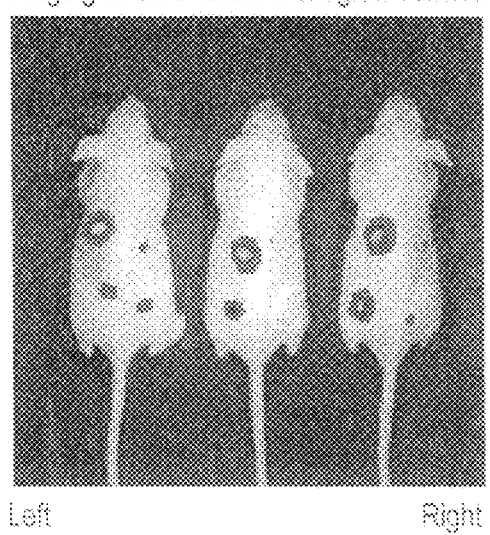
Figure 20:
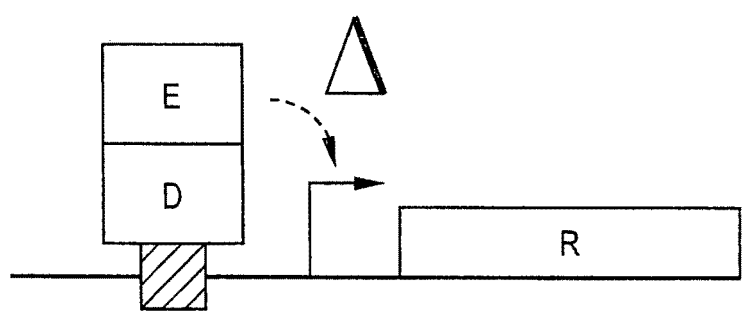
FIG. 20 is a schematic representation of a nucleic acid encoding a light-generating fusion protein of the invention.

Polyclonal Hela cells stably transfected with ODD-Luc and Luc were generated. The clones were suspended in PBS and counted. 10$^6$ cells per injection site were administered subcutaneously in duplicate into the flanks of nude mice (FIG. 18). Upon growth of palpable tumors (approximately 3-4 days) the mice were given intraperitoneal injections of phenobarbital for anesthesia, injected with a weight-adjusted dose of luciferin, and whole body imaged with a Xenogen Camera. To ensure that the difference in luciferase activity was not simply a function of tumor size alone, bidimensional tumor measurements were taken and were approximately equal.

FIG. 18 shows three different mice injected with ODD-Luc (right) and Luc (left) in duplicate. The sites where ODD-Luc was injected clearly have attenuated luciferase signal. As such, the data show a real attenuation of luciferase activity, secondary ubiquitination and destruction of ODD-Luc.

Example 3

Light-Generating Fusion Proteins Including a DNA Binding Site

In order to demonstrate the efficacy of the Second embodiment of the invention, a LGP capable of interacting with nucleic acids in order to kinetically monitor gene transcription in vivo, in vitro or in silico, the impact of cyclins on transcription was examined. As it is useful to monitor either the induction or repression of transcription, cyclins with specific affects on transcription were investigated.

Fusion of a DNA-binding motif to a cyclin does not alter cyclin binding to a cdk or the kinase activity of the cyclin/cdk complex. Mammalian expression plasmids were generated that encode fusion proteins consisting of the TET repressor DNA-binding domain (TETr) (Gossen and Bujard, 1992) fused to cyclin A or cyclin E with an intervening flexible linker consisting of $Gly_4$-Ser repeats (FIG. 8A). Both of these plasmids gave rise to stable proteins of the expected size following transfection into mammalian cells (FIG. 8B). TETr-cyclin A and TETr-cyclin E, like their unfused counterparts, bound to cdk2 (FIGS. 11 and 12) and could phosphorylate p107 in vitro. Furthermore, both TETr-cyclin A and TETr-cyclin E promoted pRB phosphorylation and bypassed a pRB-induced G1/S block when cointroduced with wild-type pRB into pRB-defective tumor cells (FIG. 8C).

Figure 9A:
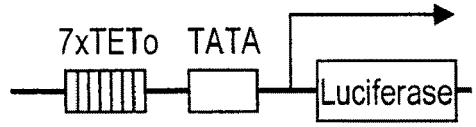
FIG. 9 shows DNA bound cyclins A and E differentially affecting transcription.
Figure 9B:
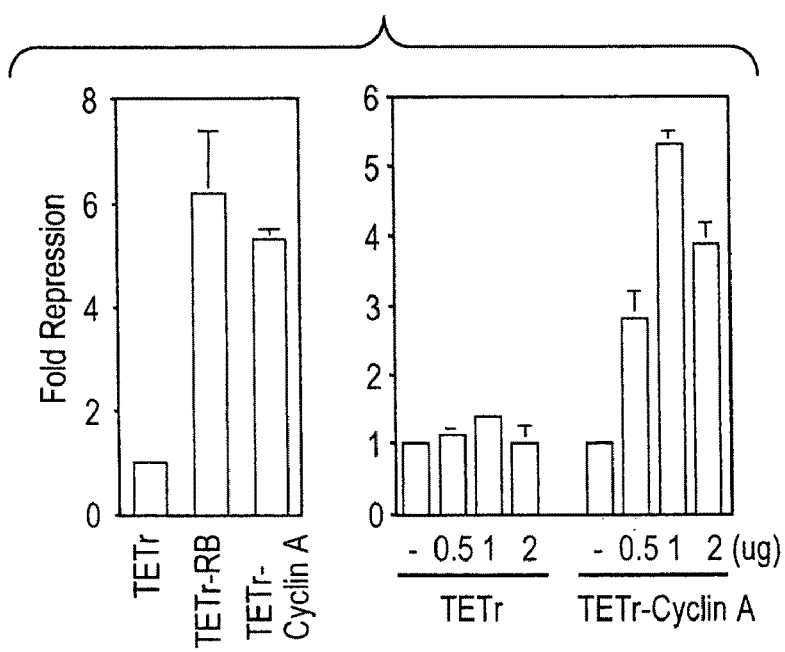
Figure 9C:
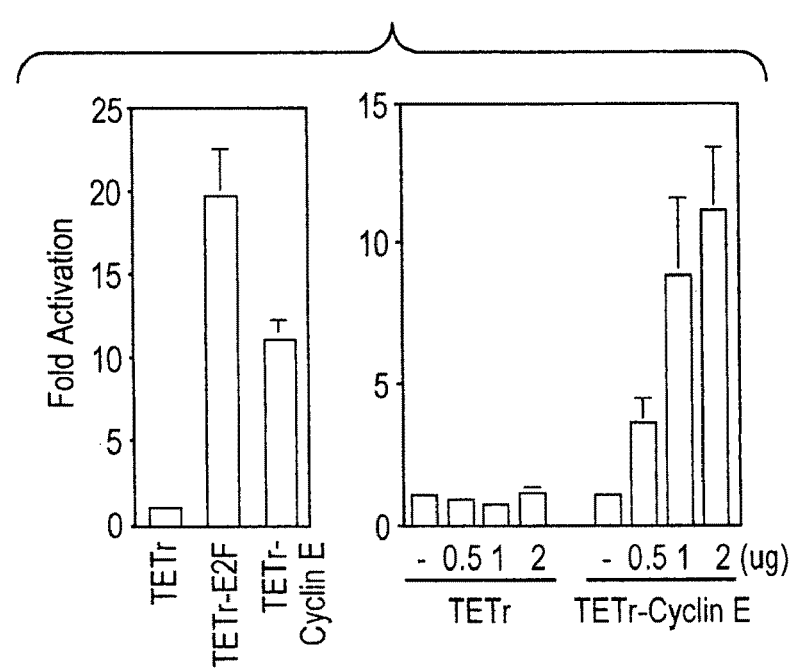
Figure 10A:
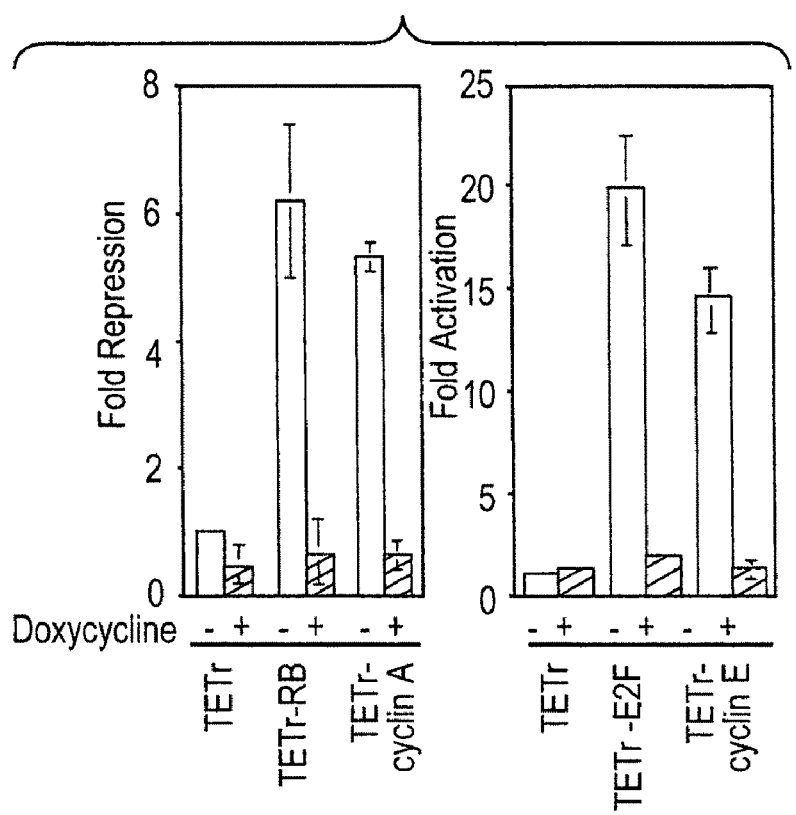
FIG. 10 illustrated transcriptional regulation by cyclins A and E dependent upon DNA binding.
Figure 10B:
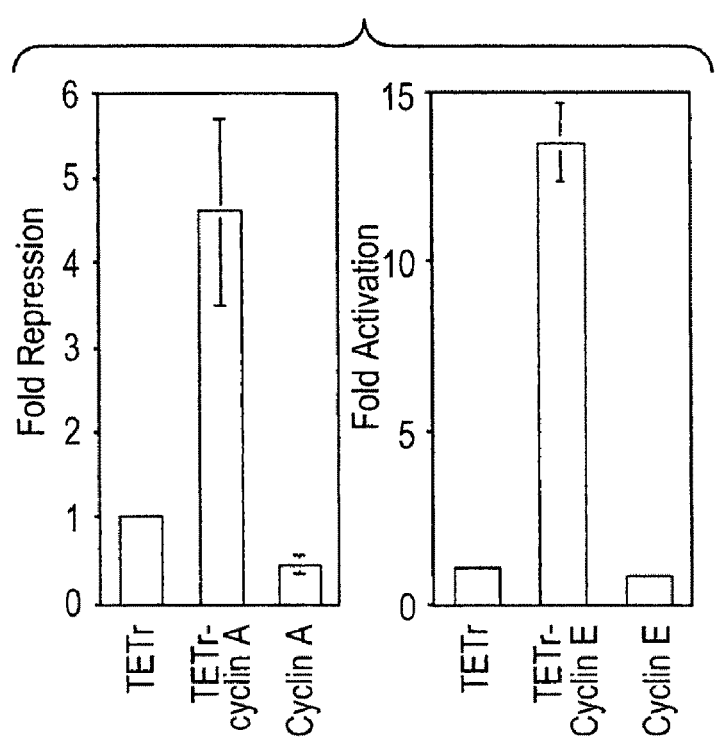

Cyclin A and cyclin E dramatically affect transcription. U2OS cells were transiently transfected with plasmids encoding various TETr fusion proteins and a luciferase reporter plasmid containing 7 TETo binding sites upstream of a TATA box derived from the CMV promoter (FIG. 9A). TETr binds specifically to TETo sites. As expected, TETr-RB repressed transcription from this reporter plasmid whereas TETr-E2F1 activated the reporter (FIG. 9B-C). The basal activity observed with this reporter plasmid presumably reflects the presence of cryptic enhancer sequences. In this and subsequent assays, the TETr domain alone was essentially inert. Surprisingly, TETr-cyclin A and TETr-cyclin E both dramatically affected transcription in this assay and did so in opposite ways. TETr-cyclin A decreased transcription approximately 80% (5-fold repression) whereas TETr-cyclin E increased transcription 10-fold (FIG. 9B-C). Doxycycline prevents the binding of TETr to TETo and completely blocked the transcriptional effects of TETr-cyclin A and TETr-cyclin E (FIG. 10A). As expected, doxycycline also blocked the transcriptional effects of TETr-RB and TETr-E2F1, which were tested in parallel. Furthermore, unfused cyclin A and E had no effects on the TETo-driven reporter plasmid (FIG. 10B). Experiments were repeated using reporters containing 1, 2, 3, or 7 TETo in which the CMV-derived TATA box was replaced with a minimal HSV TK promoter (Gossen and Bujard, 1992) (FIG. 10C). TETr-cyclin E also activated these reporters in doxycycline-inhibitable manner. The degree of activation observed with the HSV TK series of reporters was lower than with the CMV TATA-based reporter, in keeping with earlier results obtained with these reporters and fused TETr to the HSV VP16 transcriptional activation domain (Gossen and Bujard). The low basal level of transcription from these reporters precluded analysis of repression by cyclin A.

Figure 11A:
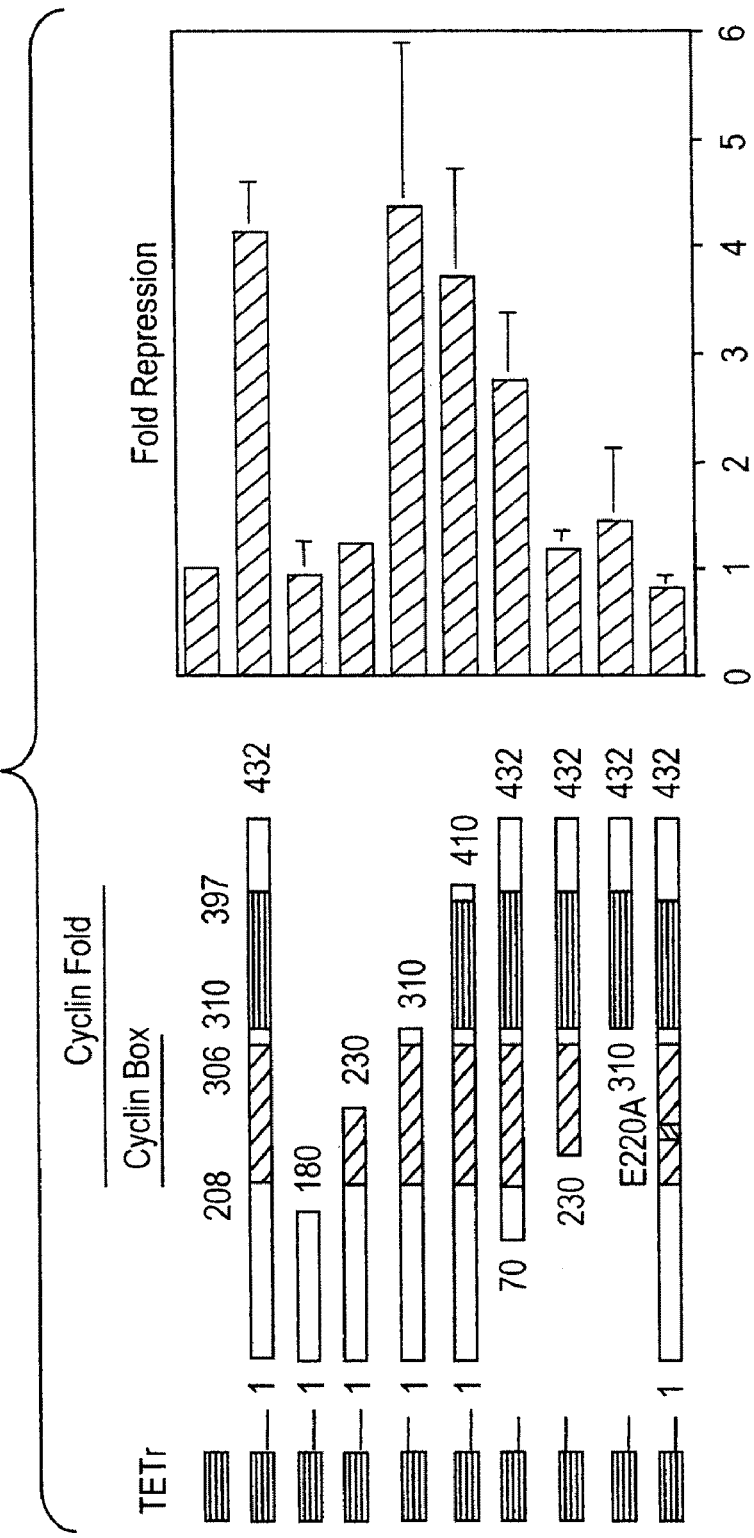
FIG. 11 depicts cyclin box is required for transcriptional repression by DNA bound is cyclin A.
Figure 11C:
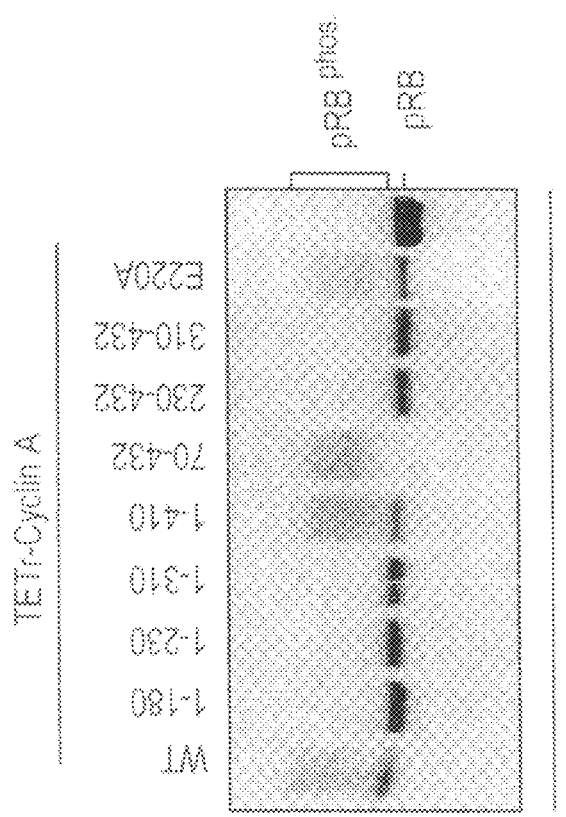
Figure 11B:
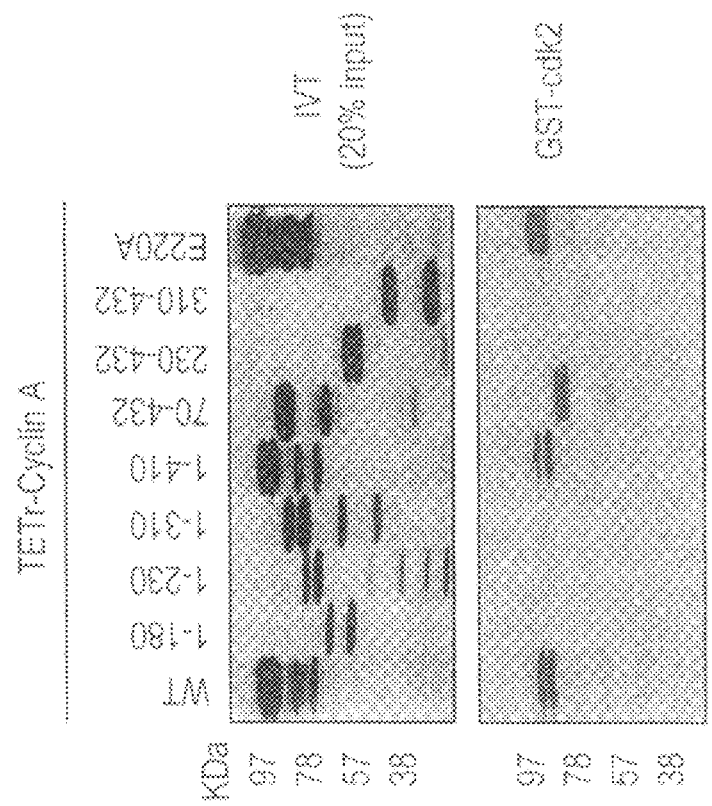
Figure 12A:
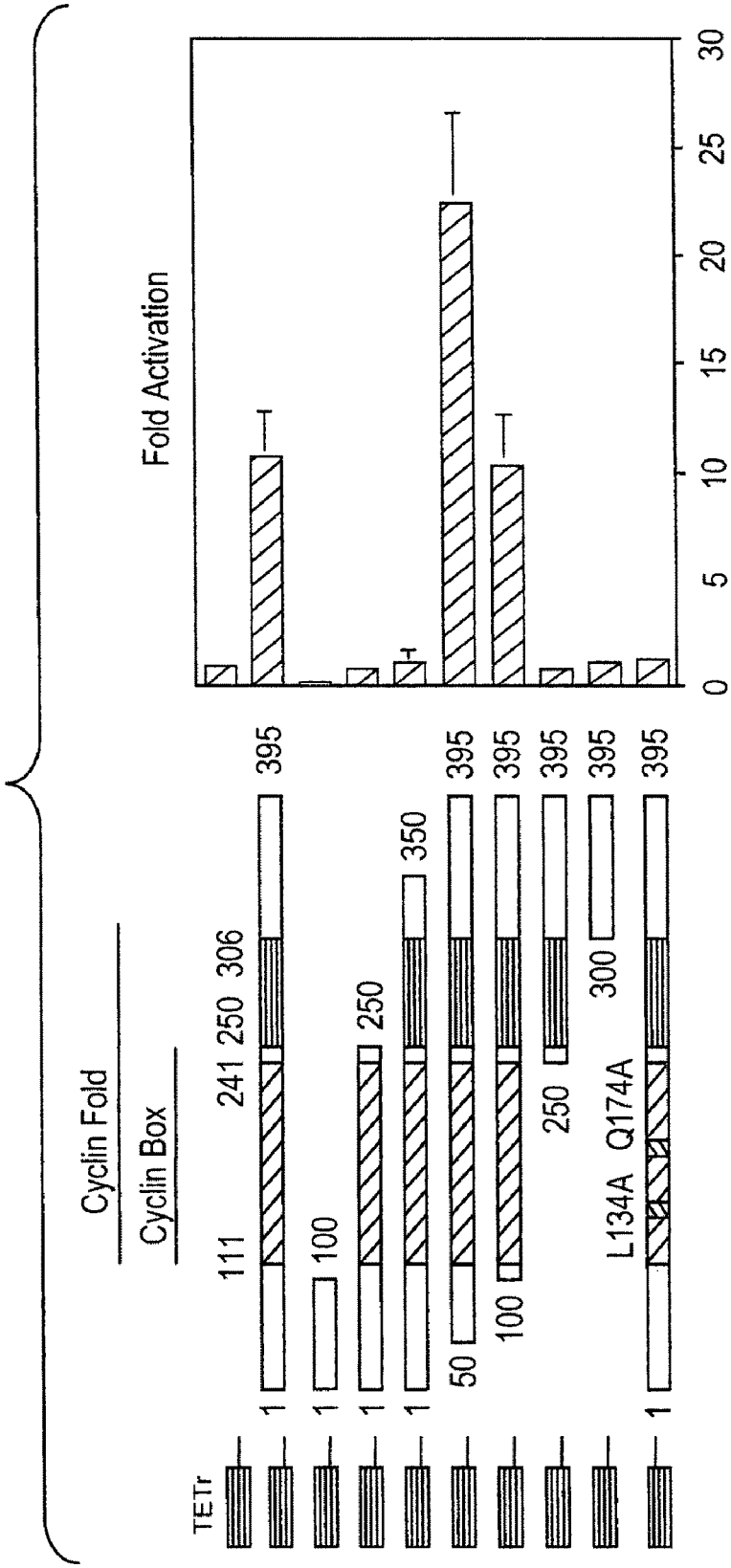
FIG. 12 illustrates that transcriptional activation by cyclin E is linked to its ability to bind to cdk2 and interact with substrates.
Figure 12C:
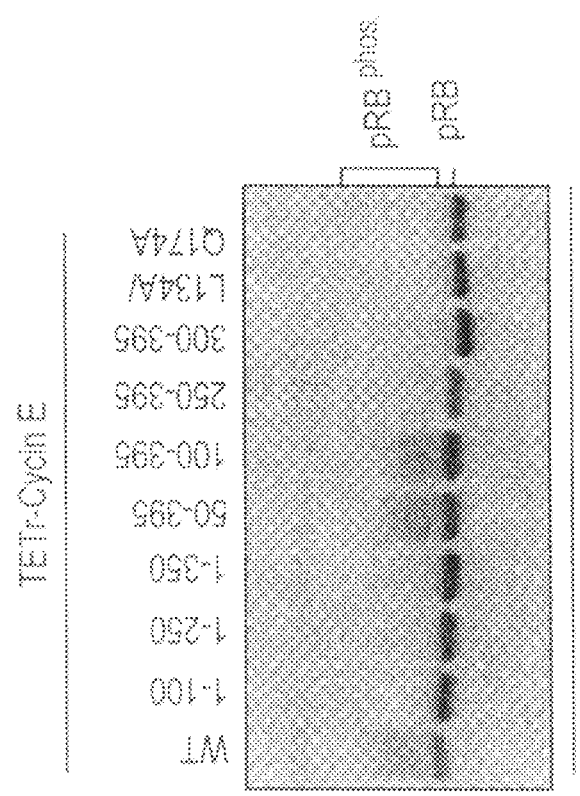
Figure 12B:
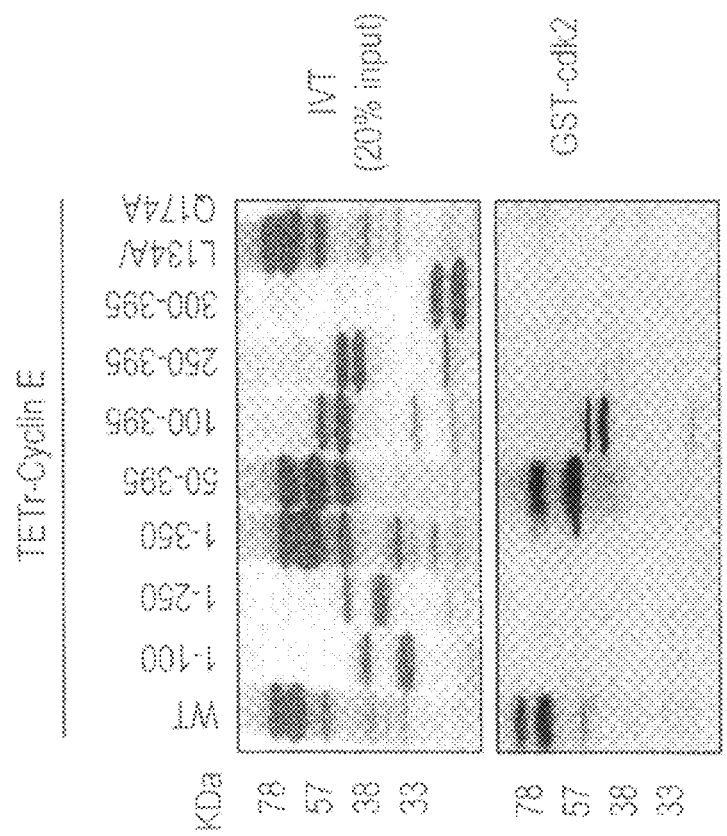

The specific domains of the cyclins that bind to the cdks are critical for cyclin-mediated transcriptional regulation. Plasmids encoding TETr fused to various colinear fragments of cyclin A and E were used to determine which regions of these molecules are required for transcriptional regulation (FIGS. 11 and 12). All of the resulting fusion proteins were expressed at comparable levels in transient transfection experiments. Cyclin A (1-310), like wild-type cyclin A, repressed transcription when fused to TETr (FIG. 11A). This fragment of cyclin A does not bind to cdk2 (FIG. 11B) and cannot direct the phosphorylation of pRB when introduced into cells (FIG. 11C). Conversely, a cyclin A point mutant (E220A) (Schulman et al., 1998) that measurably interacts with cdk2 (FIG. 11B) and directs the phosphorylation of pRB (FIG. 11C) did not repress transcription in these assays (FIG. 11A). This mutation maps to the cyclin A cyclin box (FIG. 11A). TETr-cyclin A also repressed transcription when tested in p107−/−; p130−/− mouse fibroblasts and cyclin A (1-310) does not bind to either p107 or p130. Only those cyclin E mutants that bind to cdk2 (FIG. 12B) and could direct the phosphorylation of pRB (FIG. 12C) scored as transcriptional activators (FIG. 12A). For example, Schulman et al (1998) identified cyclin A residues that are critical for substrate binding and assembly with cdk2. Mutation of analogous residues in cyclin E produced a mutant (cyclin E L134A/Q174A) that likewise failed to bind to cdk2 (FIG. 12B) and failed to phosphorylate pRB (FIG. 12C). This mutant did not activate transcription (FIG. 12). In keeping with these results, a dominant-negative form of cdk2 blocked transcriptional activation by cyclin E (FIG. 13B) but had no effect on transcriptional repression by cyclin A (FIG. 13A). Similarly, cyclin E, but not cyclin A, activated transcription in concert with a TETr-cdk2 fusion provided the kinase domain was intact (FIG. 13C). Comparable production of TETr-cdk2 and kinase-defective TETr-cdk2 (N132A) was confirmed by immunoblot assay. *Xenopus* cyclin E (Jackson et al., 1995), like its human counterpart, also activated transcription in these assays (data not shown). This activity was specific as xenopus cyclin E variants with point mutations affecting the cyclin box were inert.

Figure 14C:
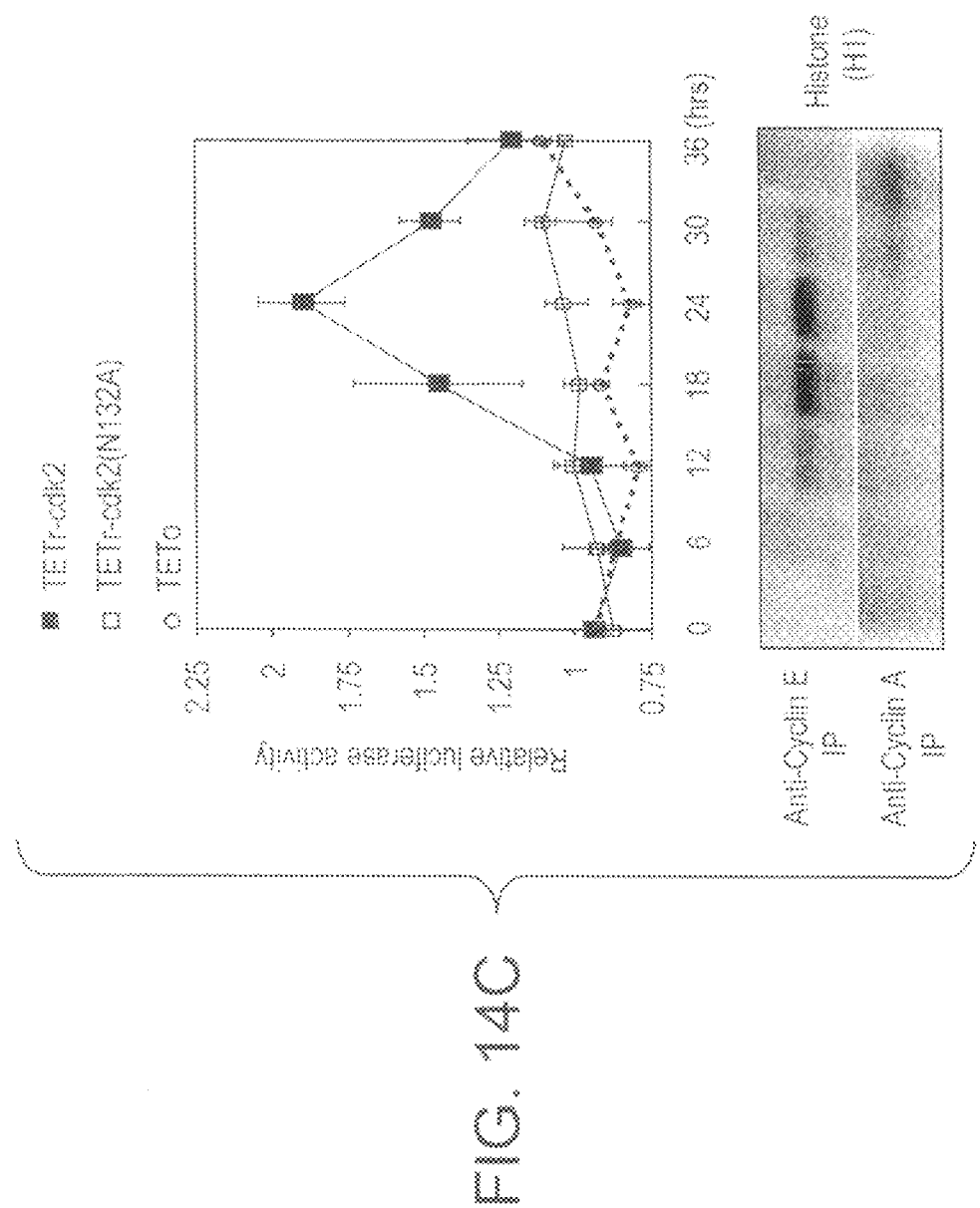
FIG. 14 shows transcriptional effects mediated by cell-cycle dependent changes in endogenous cyclins E and A.

The Second embodiment of the invention is useful to dynamically image transcription in vivo. For example, cyclin E can activate transcription under physiological conditions. 3T3 cells were transfected with the plasmid containing a selectable marker and TETo reporter plasmid with or without a plasmid encoding TETr-cdk2. Following drug selection, the stable transfectants were maintained as polyclonal pools and serum starved into quiescence. At various timepoints after serum refeeding, cell lysates were prepared and used in immunoblot, in vitro kinase, and luciferase assays (FIG. 14). In parallel, aliquots of the cells were analyzed for DNA content by FACS. In this system, S-phase entry began 18-20 hours following the addition of serum. As expected, luciferase activity increased in the TETr-cdk2 producing cells coincident with an increase in cyclin E protein levels and cyclin E-associated kinase activity (FIG. 14A-C). No such increase was observed in the cells producing equivalent amounts of TETr-cdk2 (N132A) or transfected with the reporter alone (FIG. 14C and data not shown). Note that the amount of TETr-cdk2 in these cells was less than the amount of endogenous cdk2 (FIG. 14B). Thus, the results are unlikely to be an artifact of overproduction. Luciferase values declined as cyclin E levels fell and cyclin A levels began to rise.

The Second embodiment of the invention in part relates to LGPs containing cyclin-binding domains. Thus, these LGPs are useful to dynamically quantify alterations in transcription of cell-cycle associated genes, such as oncogenes and tumor suppressors. A LGP containing a cyclin-binding moiety can be localized to regions undergoing cell proliferation, such as a tumor, and can be used to screen for and determine the efficacy of cell proliferation-modulating compounds.

Materials and Methods

Cell Lines and Transfection

U2OS human osteosarcoma cells were grown in Dulbecco's modified Eagle media (DMEM) supplemented with 10% heat-inactivated fetalclone (Hyclone) (FC), 100 units/ml penicillin, 100 mg/ml streptomycin, and 2 mM L-glutamine (PSG). SAOS-2 human osteosarcoma cells and NIH 3T3 mouse fibroblast cells were grown in DMEM supplemented with 10% heat-inactivated fetal bovine serum (FBS) and PSG. NIH 3T3 stable subclones transfected with the pCMV-neo and pUHC13-3 reporter plasmid alone or with pSG5-TETr-cdk2 or with pSG5-TETr-cdk2(N132A) were maintained in 0.7 mg/ml of G418. Cells were transfected using 2×Bes-buffered saline (2×BBS)/calcium phosphate as described (Chen and Okayama, 1987). Where indicated doxycycline (Sigma) was added 24 hours after transfection to a final concentration of 2 μg/ml. Cells were maintained in doxycycline for an additional 24 hours prior to harvest.

Plasmids pRcCMV-cdk2 dominant negative (van den Heuvel and Harlow, 1993) was a gift of Dr. Ed Harlow; pVL1393-cdk2 (N132A) (Xu et al., 1994) was a gift of Dr. Helen Piwnica-Worms; pCD19 (Tedder and Isaacs, 1989) was a gift of Dr. Thomas Tedder and pUHC13-3; ptet1-T81-luc, ptet2-T81-luc, ptet3-T81-luc, and ptet7-T81-luc (Gossen and Bujard, 1992) were gifts of Dr. Manfred Gossen. pSG5-TETr-E2F1, pSG5-TETr-RB, pSG5-HA-RB (Sellers, 1995), pGEX-2TK-cdk2 (Adams et al., 1996) have been described previously. To make pSG5-TETr-cyclin A, a protein phosphatase 1 (PP1) cDNA was first PCR amplified with oligos 5'-GCGCTGAT-CAGGCGGAGGCGGATCAGGAGGAGGAG-GATCAGGCGGAGGAGGATC AGGATCCATGTCCGA-CAGCGAGAA-3' (SEQ ID NO: 7) and 5'-GCGCGAATTCATTTCTTGGCTTTGGCAGA-3' (SEQ ID NO: 8). The PCR product was cut with BclI and EcoRI and subcloned into pSG5-TETr cut with BamHI and EcoRI to make pSG5-TETr-(Gly$_4$-Ser)$_3$-PP1. The cyclin A open reading frame (ORF) was PCR amplified with primers that introduced a 5' BamHI site and a 3' EcoRI site and subcloned into pSP72 (Promega) cut with these two enzymes to make pSP72-cyclin A. The PP1 'stuffer' from pSG5-TETr-(Gly$_4$-Ser)$_3$-PP1 was then excised by digestion with BamHI and EcoRI and replaced with the cyclin A cDNA insert from pSP72-cyclin A. To make pSG5-TETr-cyclin E, the cyclin E ORF in pRcCMV-cyclin E was PCR amplified with primers that introduced a 5' BglII and 3' EcoRI site. The PCR product was cut with these two enzymes and ligated into the BamHI-EcoRI backbone of pSG5-TETr-PP1. In parallel, these restricted cyclin A and cyclin E PCR products were subcloned into pSG5-HA cut with BamHI and EcoRI to make pSG5-HA-cyclin A and pSG5-HA-cyclin E, respectively. Plasmids encoding cyclin A and cyclin E N-terminal and C-terminal deletion mutants were made in an analogous fashion by using PCR primers that selectively amplified the desired coding regions. To make pSG5-TETr-cdk2 and pSG5-TETr-cdk2 (N132A), the cdk2 ORF in pRcCMV-cdk2 and pVL1393-cdk2 (N132A), respectively, were PCR amplified with primers that introduced a 5' BamHI and 3' EcoRI site. The PCR products were cut with these two enzymes and ligated into the BamHI-EcoRI backbone of pSG5-TETr-PP1. All PCR reactions were performed with Pfu DNA polymerase and the authenticity of plasmids containing the entire cyclin A, cyclin E, or cdk2 open reading frame was confirmed by direct DNA sequencing. pSG5-TETr-cyclin A (E220A) and pSG5-TETr-cyclin E (L134A/Q174A) were generated using Transformer Site-Directed Mutagenesis Kit (Clontech) according to manufacture's instructions using pSG5-TETr-cyclin A and pSG5-TETr-cyclin E as a template, respectively, and confirmed by DNA sequencing.

Antibodies and Immunoblot Analysis

Monoclonal anti-TETr was purchased from Clontech and anti-HA (12CA5) was purchased from Boehringer Mannheim. Polyclonal anti-cyclin A (SC-751), monoclonal and polyclonal anti-cyclin E (SC-247, SC-481), and polyclonal anti-cdk2 (SC-163) were purchased from Santa Cruz. Cell extracts were made by lysis in EBC buffer (50 mM Tris [pH8], 120 mM NaCl, 0.5% Nonidet P-40). For immunoblot analysis, ~100 μg of cell extract was loaded per lane. Nitrocellulose filters were blocked in 4% powdered milk/1% goat serum in TBS-T (10 mM Tris [pH 8], 0.05% Tween, 150 mM NaCl) for 1 hour at room temperature prior to incubation in primary antibody. Anti-HA (12CA5) was used at a concentration of 1.0 μg/ml, anti-TETr antibody at 1:500 dilution (v/v), anti-cyclin A (SC-751) at 1:1,000 dilution (v/v), anti-cyclin E (SC-247, SC-481) at 1:1,000 dilution (v/v) and anti-cdk2 (SC-163) at 1:1,000 dilution (v/v). Following 4 washes with TBS/T, bound antibody was detected using alkaline phosphatase-conjugated secondary antibodies.

GST Pull-Down Assay

Glutathione S-transferase pull-down assays were performed basically as described previously (Kaelin et al., 1991). Binding reactions contained 10 μl of $^{35}$S-radiolabelled in vitro translates made with a TNT kit (Promega) and approximately 1 μg of the indicated GST fusion protein in 1 ml of NETN (20 mM Tris [pH 8], 100 mM NaCl, 1 mM EDTA, 0.5% Nonidet P-40). Following 1 hour incubation at 4° C. with rocking, the Sepharose was washed 5' times with NETN. Bound proteins were eluted by boiling in SDS-containing sample buffer and resolved by SDS-polyacrylamide gel electrophoresis. Comparable loading of GST-fusion proteins was confirmed by Coomassie brilliant blue staining and $^{35}$S-radiolabelled proteins were detected by fluorography.

FACS/Cell Cycle Analysis

Fluorescence activated cell sorting (FACS) was done essentially as described (Qin et al., 1995). Briefly, subconfluent SAOS-2 cells grown in 100 mm dishes were transfected with 2 μg of pCD19 and 10 μg of pSG5-HA-RB together with plasmids encoding the indicated cyclins. 72 hr later the cells were harvested with trypsin-EDTA and stained with FITC-conjugated anti-CD19 antibody (CALTAG) and propidium iodide. Samples were analyzed by two-color FACS with a FACScan (Becton Dickinson). For cell cycle synchronization, cells were starved in serum-free DMEM for 72 hours before being stimulated with 10% FBS.

Luciferase Reporter Gene Assay

For TETr-fusion transcriptional assay, subconfluent U2OS cells were transiently transfected in 6-well plates in duplicate with 1 μg of pCMV-μgal, 1 μg of pUHC13-3 reporter plasmid, and 3 μg of the indicated plasmids encoding TETr-fusion proteins. Sufficient parental pSG5-TETr was added so that each reaction mix contained the same amount of pSG5-TETr backbone. 48 hours after transfection luciferase activity and β-galactosidase activity was determined as described previously (Qin, 1995).

In Vitro Kinase Assay

500 μg of cell extract was incubated with protein A Sepharose and 1 μg of anti-cyclin E (SC-481) or anti-cyclin A (SC-751) antibody for 1 hour at 4° C. in a final volume of 0.5 ml. The Sepharose was then washed 5 times with NETN and 3 times in IP kinase (IPK) buffer (50 mM Tris-HCl [pH 7.5], 10 mM MgCl$_2$, 1 mM DTT). The Sepharose was then resuspended in 27 μl of IPK buffer to which was added 2 μl of histone H1 (1 mg/ml) and 1 μl of [γ-$^{32}$P] ATP (6,000 Ci/mmol, 10 mCi/ml) and incubated for 30 min at 30° C. Reactions were stopped by addition of Laemmli sample buffer, boiled, resolved by SDS-polyacrylamide gel electrophoresis, and subjected to autoradiography.

REFERENCES

1. G. Semenza, *Annu. Rev. Cell Dev. Biol.* 15, 551-578 (1999).
2. R. Wenger, *J Exper Biol* 203, 1253-1263 (2000).
3. G. Semenza, *Cell* 98, 281-4 (1999).
4. H. Zhu, F. Bunn, *Resp. Phys.* 115, 239-247 (1999).
5. M. Ivan, W. G. Kaelin, *Current Opinion in Gen and Dev* In Press (2000).
6. E. Maher, W. G. Kaelin, *Medicine* 76, 381-91 (1997).

7. M. Tyers, R. Rottapel, *Proc Natl Acad Sci USA* 1999 Oct. 26; 96(22):12230-2 96, 12230-2 (1999).
8. W. Krek, *Nat Cell Biol* 2000 July; 2(7):E121-3 2, E121-3 (2000).
9. C. E. Stebbins, W. G. Kaelin, N. P. Pavletich, *Science* 284, 455-461 (1999).
10. M. Ohh, et al., *Nature Cell Biology* 2, 423-427 (2000).
11. T. Kamura, et al., *Proc. Natl. Acad. Sci.* (USA) 97, 10430-10435 (2000).
12. M. Cockman, et al., *J Biol Chem* 275, 25733-41 (2000).
13. K. Tanimoto, Y. Makino, T. Pereira, L. Poellinger, *EMBO J.* 19, 4298-4309 (2000).
14. P. Maxwell, et al., *Nature* 399, 271-5 (1999).
15. M. A. Goldberg, S. P. Dunning, H. F. Bunn, *Science* 242, 1412-1415 (1988).
16. G. Wang, G. Semenza, *Blood* 82, 3610-5 (1993).
17. V. Ho, H. Bunn, *Biochem Biophys Res Commun* 1996 Jun. 5; 223(1):175-80 223, 175-80 (1996).
18. D. Chowdary, J. Dermody, K. Jha, H. Ozer, *Mol Cell Biol* 14, 1997-2003 (1994).
19. L. E. Huang, J. Gu, M. Schau, H. F. Bunn, *Proc Natl Acad Sci USA* 95, 7987-92 (1998).
20. C. Pugh, J. O'Rourke, M. Nagao, J. Gleadle, P. Ratcliffe, *J Biol Chem* 272, 11205-14 (1997).
21. V. Srinivas, L. Zhang, X. Zhu, J. Caro, *Biochem Biophys Res Commun* 260, 557-61 (1999).
22. K. I. Kivirikko, J. Myllyharju, Matrix *Biology* 16, 357-368 (1998).
23. A. Winter, A. Page, *Mol Cell Biol* 20, 4084-4093 (2000).
24. L. Friedman, et al., *Proc Natl Acad Sci USA* 97, 4736-41 (2000).
25. O. Iliopoulos, A. Kibel, S. Gray, W. G. Kaelin, *Nature Medicine* 1, 822-826 (1995).
26. R. Deshaies, *Annu Rev Cell Dev Biol* 15, 435-67 (1999).
27. Y. Takahashi, S. Takahashi, Y. Shiga, T. Yoshimi, T. Miura, *J Biol Chem* 275, 14139-46 (2000).
28. C. Levene, C. Bates, *Biochim Biophys Acta* 444, 446-52 (1976).
29. L. Huang, W. Willmore, J. Gu, M. Goldberg, H. Bunn, *J Biol Chem* 274, 9038-44 (1999).
30. Y. Liu, et al., *J Biol Chem* 273, 15257-62 (1998).
31. T. Morita, S. Kourembanas, *J Clin Invest* 96, 2676-82 (1995).
32. C. Sutter, E. Laughner, G. Semenza, *Proc Natl Acad Sci USA* 97, 4748-53 (2000).
33. G. Wang, B. Jiang, G. Semenza, *Biochem Biophys Res Commun* 1995 Nov. 13; 216(2):669-75 216, 669-75 (1995).
34. K. Sogawa, et al., *Proc Natl Acad Sci USA* 1998 Jun. 23; 95(13):7368-73 95, 7368-73 (1998).
35. S. Salceda, I. Beck, V. Srinivas, J. Caro, *Kidney Int* 1997 February; 51(2):556-9 51, 556-9 (1997).
36. J. Wingrove, P. O'Farrell, *Cell* 1999 Jul. 9; 98(1):105-14 98, 105-14 (1999).
37. L. Palmer, G. Semenza, M. Stoler, R. Johns, *Am J Physiol* 274, L212-9 (1998).
38. G. Melillo, et al., *J Exp Med* 1995 Dec. 1; 182(6):1683-93 182, 1683-93 (1995).
39. M. Bickel, et al., *Hepatology* 28, 404-11 (1998).
40. T. Franklin, W. Morris, P. Edwards, M. Large, R. Stephenson, *Biochem J* 353, 333-338 (2001).
41. Adams, P. D., Sellers, W. R., Sharma, S. K., Wu, A. D., Nalin, C. M. and Kaelin, W. G. (1996) Identification of a Cyclin-cdk2 recognition motif present in substrates and p21-like cdk inhibitors. *Mol. Cell. Biol.* 16, 6623-6633
42. Adams, P. D., Li, X., Sellers, W. R., Baker, K. B., Leng, X., Harper, J. W., Taya, Y. and Kaelin, W. G. (1999) The retinoblastoma protein contains a C-terminal motif that targets it for phosphorylation by cyclin/cdk complexes. *Mol. Cell. Biol.* 19, 1068-1080
43. Akoulitchev, S., Chuikov, S., Reinberg, D. (2000) TFIIH is negatively regulated by cdk8-containing mediator complexes. *Nature,* 407, 102-6
44. Bagby, S., Kim, S., Maldonado, E., Tong, K. I., Reinberg, D. and Ikura, M. (1995) Solution structure of the C-terminal core domain of human TFIIB: similarity to cyclin A and interaction with TATA-binding protein. *Cell* 82, 857-867
45. Bandara, L. R., Adamczewski, J. P., Hunt, T. and La Thangue, N. B. (1991) Cyclin A and the retinoblastoma gene product complex with a common transcription factor. *Nature* 352, 249-251
46. Beijersbergen, R. L., Carlee, L., Kerkhoven, R. M. and Bernards, R. (1995) Regulation of the retinoblastoma protein-related p107 by G1 cyclin complexes. *Genes Dev.* 9, 1340-1353
47. Bieniasz, P. D., Grdina, T. A., Bogerd, H. P. and Cullen, B. R. (1999) Recruitment of cyclin T1/P-TEFb to an HIV type 1 long terminal repeat promoter proximal RNA target is both necessary and sufficient for full activation of transcription. *Proc. Natl. Acad. Sci. USA* 96, 7791-7796
48. Bochar, D. A., Pan, Z. Q., Knights, R., Fisher, R. P., Shilatifard, A. and Shiekhattar, R. (1999) Inhibition of transcription by the trimeric cyclin-dependent kinase 7 complex. *Biol. Chem.* 274, 13162-13166
49. Chen, C. and Okayama, H. (1987) High-efficiency transformation of mammalian cells by plasmid DNA. *Mol. Cell. Biol.* 7, 2745-2752
50. Chen, J., Saha, P., Kornbluth, S., Dynlacht, B. D. and Dutta, A. (1996) Cyclin-binding motifs are essential for the function of p21CIP1. *Mol. Cell. Biol.* 16, 4673-4682
51. Dahmus, M. E. (1996) Reversible phosphorylation of the C-terminal domain of RNA polymerase II. *J. Biol. Chem.* 271, 19009-19012
52. Devoto, S. H., Mudryj, M., Pines, J., Hunter, T. and Nevins, J. R. (1992) A cyclin A protein kinase complex possesses sequence specific DNA binding activity; p33cdk2 is a component of the E2F-Cyclin A complex. *Cell* 68, 167-176
53. Dynlacht, B. D. (1997) Regulation of transcription by proteins that control the cell cycle. *Nature* 389, 149-152
54. Dynlacht, B. D., Brook, A., Dembski, M., Yenush, L. and Dyson, N. (1994) DNA-binding and trans-activation properties of *drosophila* E2F and DP proteins. *Proc. Natl. Acad. Sci. USA* 91, 6359-6363
55. Dynlacht, B. D., Moberg, K., Lees, J. A., Harlow, E. and Zhu, L. (1997) Specific regulation of E2F family members by cyclin-dependent kinases. *Mol. Cell. Biol.* 17, 3867-3875
56. Ewen, M. E., Faha, B., Harlow, E. and Livingston, D. M. (1992) Interaction of p107 with cyclin A independent of complex formation with viral oncoproteins. *Science* 255, 85-87
57. Faha, B., Ewen, M., Tsai, L., Livingston, D. M. and Harlow, E. (1992) Interaction between human cyclin A and adenovirus E1A-associated p107 Protein. *Science* 255, 87-90

58. Felzen, L. K., Farrell, S., Betts, J. C., Mosavin, R. and Nabel, G. J. (1999) Specificity of cyclin-cdk2, TFIIB, and E1A interactions with a common domain of the p300 coactivator. *Mol. Cell. Biol.* 19, 4241-4246

59. Fu, T. J., Peng, J., Lee, G., Price, D. H. and Flores, O. (1999) Cyclin K functions as a CDK9 regulatory subunit and participates in RNA polymerase II transcription. *J. Biol. Chem.* 274, 34527-34530

60. Gebara, M. M., Sayre, M. H. and Corden, J. L. (1997) Phosphorylation of the carboxy-terminal repeat domain in RNA polymerase II by cyclin-dependent kinases is sufficient to inhibit transcription. *J. Cell. Biochem.* 64, 390-402

61. Gossen, M. and Bujard, H. (1992) Tight control of gene expression in mammalian cells by tetracycline-responsive promoters. *Proc. Natl. Acad. Sci. USA* 89, 5547-5551

62. Hannon, G. J., Demetrick, D. and Beach, D. (1993) Isolation of the Rb-related p130 through its interactions with CDK2 and cyclins. *Genes Dev.* 7, 2378-2391

63. Hengartner, C. J., Myer, V. E., Liao, S. M., J., W. C., Koh, S. S, and Young, R. A. (1998) Temporal regulation of RNA polymerase II by Srb10 and Kin28 cyclin-dependent kinases. *Mol. Cell.* 2, 43-53

64. Jackson, P. K., Chevalier, S., Philippe, M. and Kirschner, M. W. (1995) Early events in DNA replication require cyclin E and are blocked by p21CIP1. *J. Cell. Biol.* 130, 755-69

65. Jeffrey, P., Gorina, S. and Pavietich, N. (1995) Crystal structure of the tetramerization domain of the p53 tumor suppressor at 1.7 angstroms. *Science* 267, 1498-1502

66. Jones, K. A. (1997) Taking a new TAK on Tat transactivation. *Genes Dev.* 11, 2593-2599

67. Kaelin, W. G., Pallas, D. C., DeCaprio, J. A., Kaye, F. J. and Livingston, D. M. (1991) Identification of cellular proteins that can interact specifically with the T/E1A-binding region of the retinoblastoma gene product. *Cell* 64, 521-532

68. Kimmelman, J., Kaldis, P., Hengartner, C. J., Laff, G. M., Koh, S. S., Young, R. A. and Solomon, M. J. (1999) Activating phosphorylation of the Kin28p subunit of yeast TFIIH by Cak1p. *Mol. Cell. Biol.* 19, 4774-4787

69. Krek, W., Ewen, M., Shirodkar, S., Arany, Z., Kaelin, W. G. and Livingston, D. M. (1994) Negative regulation of the growth-promoting transcription Factor E2F-1 by a stably bound cyclin A-dependent protein kinase. *Cell* 78, 1-20

70. Lania, L., Majello, B. and Napolitano, G. (1999) Transcriptional control by cell-cycle regulators: a review. *J. Cell. Physiol.* 179, 134-141

71. Lee, M. H., Williams, B. O., Mulligan, G., Mukai, S., Bronson, R. T., Dyson, N., Harlow, E. and Jacks, T. (1996) Targeted disruption of p107: functional overlap between p107 and Rb. *Genes Dev.* 10, 1621-1632

72. Lees, E., Faha, B., Dulic, V., Reed, S. I. and Harlow, E. (1992) Cyclin E/cdk2 and cyclin A/cdk2 kinases associate with p107 and E2F in a temporally distinct manner. *Genes Dev.* 6, 1874-1885

73. Leresche, A., Wolf, V. J. and Gottesfeld, J. M. (1996) Repression of RNA polymerase II and III transcription during M phase of the cell cycle. *Exp Cell Res.* 229, 282-288

74. Ma, T., Van Tine, B. A., Wei, Y., Garrett, M. D., Nelson, D., Adams, P. D., Wang, J., Qin, J., Chow, L. T., Harper, J. W. (2000) Cell cycle-regulated phosphorylation of p220NPAT by cyclin E/Cdk2 in Cajal bodies promotes histone gene transcription. *Genes Dev.*, 14, 2298-2313

75. Majello, B., Napolitano, G., Giordano, A. and Lania, L. (1999) Transcriptional regulation by targeted recruitment of cyclin-dependent CDK9 kinase in vivo. *Oncogene*, 18, 4598-4605

76. Mudryj, M., Devoto, S. H., Hiebert, S. W., Hunter, T., Pines, J. and Nevins, J. R. (1991) Cell cycle regulation of the E2F transcription factor involves an interactin with cyclin A. *Cell* 65, 1243-1253

77. Neuman, E., Ladha, M. H., Lin, N., Upton, T. M., Miller, S. J., DiRenzo, J., Pestell, R. G., Hinds, P. W., Dowdy, S. F., Brown, M., Ewen, M. E. (1997) Cyclin D1 stimulation of estrogen receptor transcriptional activity independent of cdk4. *Mol Cell Biol* 17, 5338-47

78. Noble, M. E., Endicott, J. A., Brown, N. R. and Johnson, L. N. (1997) The cyclin box fold: protein recognition in cell-cycle and transcription control. *Trends Biochem Sci.* 22, 482-487

79. Peeper, D. S., Parker, L. L., Ewen, M. E., Toebes, M., Frederick, F. L., Xu, M., Zantema, A., van der Eb, A. J. and Pinwica-Worms, H. (1993) A- and B-type cyclins differentially modulate substrate specificity of cyclin-CDK complexes. *EMBO J.* 12, 1947-1954

80. Perkins, N. D., Felzen, L. K., Betts, J. C., Leung, K., Beach, D. H. and Nabel, G. J. (1997) Regulation of NF-kappaB by cyclin-dependent Kinases associated with the p300 Coactivator. *Science* 275, 523-527

81. Qin, X.-Q., Livingston, D. M., Ewen, M., Sellers, W. R., Arany, Z., and Kaelin, W. G. (1995) The transcription factor E2F1 is a downstream target of RB action. *Mol. Biol. Cell.* 15, 742-755

82. Rickert, P., Corden, J. L. and Lees, E. (1999) Cyclin C/CDK8 and cyclin H/CDK7/p36 are biochemically distinct CTD kinases. Oncogene 18, 1093-1102

83. Roberts, J. M. (1999) Evolving ideas about cyclins. *Cell* 98, 129-132

84. Schulman, B., Lindstrom, D. and Harlow, E.: (1998) Substrate recruitment to cyclin-dependent kinase 2 by a multipurpose docking site on cyclin A. *Proc. Natl. Acad. Sci. USA* 95, 10453-10458

85. Schwarz, J. K., Devoto, S. H., Smith, E. J., Chellappan, S. P., Jakoi, L. and Nevins, J. R. (1993) Interactions of the p107 and Rb proteins with E2F during the cell proliferation response. *EMBO J.* 12, 1013-1020

86. Sellers, W. R., Neuman, E. and Kaelin, W. G. (1995) The Retinoblastoma protein contains a potent transrepression domain which Induces a cell-cycle block when bound to DNA. *Proc. Natl. Acad. Sci. USA* 92, 11544-11548

87. Shanahan, F., Seghezzi, W., Parry, D., Mahony, D. and Lees, E. (1999) Cyclin E associates with BAF155 and BRG1, components of the mammalian SWI-SNF complex, and alters the ability of BRG1 to induce growth arrest. *Mol. Cell. Biol.* 19, 1460-1469

88. Sherr, C. J. (1996) Cancer Cell Cycles. Science, 274, 1672-1677

89. Smith, E. J., Leone, G. and Nevins, J. R. (1998) Distinct mechanisms control the accumulation of the Rb-related p107 and p130 proteins during cell growth. *Cell Growth Differ.* 9, 297-303

90. Starostik, P., Chow, K. N. and Dean, D. C. (1996) Transcriptional repression and growth suppression by the p107 pocket protein. *Mol. Cell. Biol.* 16, 3606-3614

91. Tedder, T. F. and Isaacs, C. M. (1989) Isolation of cDNAs Encoding the CD19 Antigen of Human and Mouse B Lymphocytes. *J. Immunology* 143, 712-717

92. van den Heuvel, S, and Harlow, E. (1993) Distinct roles for cyclin-dependent kinases in cell cycle control. *Science* 262, 2050-2053
93. Weinberg, R. A. (1995) The retinoblastoma protein and cell cycle control. Cell 81, 323-330
94. Xu, M., Sheppard, K. A., Peng, C-Y., Yee, A. S., and Piwnica-Worms, H. (1994) Cyclin A/cdk2 binds directly to E2F1 and inhibits the DNA-binding activity of E2F1/DP1 by phosphorylation. *Mol. Cell. Biol.* 14, 8420-8431
95. Yankulov, K. Y. and Bentley, D. L. (1997) Regulation of CDK7 substrate specificity by MAT1 and TFIIH. *EMBO J.* 16, 1638-1646
96. Zamanian, M. and La Thangue, N. B. (1993) Transcriptional repression by the RB-related protein p107. *Mol. Biol. Cell* 4, 389-396
97. Zhao, J., Dynlacht, B., Imai, T., Hori, T. and Harlow, E. (1998) Expression of NPAT, a novel substrate of cyclin E-CDK2, promotes S-phase entry. *Genes Dev.* 12, 456-461
98. Zhao, J., Kennedy, B. K., Lawrence, B. D., Barbie, D. A., Matera, A. G., Fletcher, J. A. and Harlow, E. (2000) NPAT links cyclin E-Cdk2 to the regulation of replication-dependent histone gene transcription. *Genes and Dev.* 14, 2283-2297
99. Zhu, L., Enders, G., Lees, J. A., Beijersbergen, R. L., Bernards, R. and Harlow, E. (1995a) The pRB-related protein p107 contains two growth suppression domains: Independent interactions with E2F and cyclin/cdk complexes. *EMBO J.* 14, 1904-1913
100. Zhu, L., Harlow, E. and Dynlacht, B. D. (1995b) p107 uses a p21/CIP1-related domain to bind cyclin/cdk2 and regulate interactions with E2F. *Genes Dev.* 9, 1740-1752
101. Zhu, Y., Pe'ery, T., Peng, J., Ramanathan, Y., Marshall, N., Marshall, T., Amendt, B., Mathews, M. B. and Price, D. H. (1997) Transcription elongation factor P-TEFb is required for HIV-1 tat transactivation in vitro. *Genes Dev.* 11, 2622-2632
102. Zwijsen, R. M., Wientjens, E., Klompmaker, R., van der Sman, J., Bernards, R., Michalides, R. J. (1997) CDK-independent activation of estrogen receptor by cyclin D1. *Cell* 88, 405-15
103. Zwijsen, R. M., Buckle, R. S., Hijmans, E. M., Loomans, C. J., Bernards, R. (1998) Ligand-independent recruitment of steroid receptor coactivators to estrogen receptor by cyclin D1. *Genes Dev.* 12, 3488-98

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, issued patents, and published patent applications cited throughout this application are hereby incorporated by reference. The appropriate components, processes, and methods of those patents, applications and other documents may be selected for the present invention and embodiments thereof.

What is claimed is:

1. A method of identifying a compound that decreases proline hydroxylation of the alpha subunit of hypoxia inducible factor (HIFα), the method comprising:
   a) contacting a compound and a non-hydroxylated HIFα polypeptide comprising one or more hydroxylatable proline residues under conditions wherein the HIFα polypeptide, in the absence of compound, is hydroxylated on at least one proline residue;
   b) measuring the degree of prolyl hydroxylation of HIFα in the presence of compound; and
   c) comparing the degree of prolyl hydroxylation of HIFα in the presence of compound to the degree of prolyl hydroxylation of HIFα in the absence of compound, wherein a decrease in the degree of prolyl hydroxylation in the presence of compound compared to the degree of prolyl hydroxylation in the absence of compound identifies a compound that decreases proline hydroxylation of HIFα.

2. The method of claim 1, wherein measuring the degree of prolyl hydroxylation comprises contacting the HIFα polypeptide with pVHL and measuring the amount of pVHL bound by the polypeptide.

3. The method of claim 1, wherein said HIFα polypeptide comprises the amino acid sequence Y—$X_1$-Leu-$X_2$-Pro-$X_3$—$X_4$—$X_5$—$X_6$—Y', wherein
   a) $X_1$, $X_2$, $X_4$, $X_5$, and $X_6$ are independently Gly, Ala, Val, Leu, Ile, Pro, Met, Phe, or Trp;
   b) $X_3$ is Ser, Thr, or Tyr; and
   c) Y and Y' are independently present or absent and, if present, independently comprise a peptide having from 1 to 600 amino acids.

4. The method of claim 1, wherein said HIFα polypeptide moiety comprises the amino acid sequence corresponding to the N-terminal residues 1-600 of HIF1α, numbered in accordance with wild type HITF1α.

5. The method of claim 1, wherein said HIFα polypeptide moiety comprises a 4 to 12 amino acid sequence corresponding to the residues adjacent to and/or surrounding residue 564, inclusive, of HIF1α, numbered in accordance with wild type HIF160 .

6. The method of claim 1, wherein said HIFα polypeptide moiety comprises a 12 to 14 amino acid sequence corresponding to the residues adjacent to and/or surrounding residue 564, inclusive, of HIF1α, numbered in accordance with wild type HIT1α.

7. The method of claim 1, wherein said HIFα polypeptide moiety comprises a 20 to 30 amino acid sequence corresponding to the residues adjacent to and/or surrounding residue 564, inclusive, of HIF1α, numbered in accordance with wild type HIF1α.

8. The method of claim 1 wherein said HIFα polypeptide moiety comprises a 80 to 120 amino acid sequence corresponding to the residues adjacent to and/or surrounding residue 564, inclusive, of HIF1α, numbered in accordance with wild type HIF1α.

9. The method of claim 1, wherein said HIFα polypeptide moiety comprises amino acids 555-575 of human HIF1α, numbered in accordance with wild type HIF1α.

10. The method of claim 1, wherein the decrease in degree of prolyl hydroxylation of HIFα is due to the compound inhibiting a prolyl hydroxylase.

11. The method of claim 1, wherein the HIFα polypeptide is selected from the group consisting of HIF1α, HIF2α, and HIF3α.

* * * * *

```
SEQUENCE LISTING

<160> NUMBER OF SEQ ID NOS: 23

<210> SEQ ID NO 1
<211> LENGTH: 10
<212> TYPE: PRT
<213> ORGANISM: Artificial Sequence
<220> FEATURE:
<223> OTHER INFORMATION: Consensus Target Peptide

<400> SEQUENCE: 1

Pro Lys Pro Leu Lys Lys Leu Arg Phe Asp
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Target Peptide

<400> SEQUENCE: 2

Gly Arg Pro Pro Val Lys Arg Arg Leu Asp Leu Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Target Peptide

<400> SEQUENCE: 3

Cys Cys Ser Lys Ala Cys Arg Arg Leu Phe Gly Pro
1               5                   10
```

```
<210> SEQ ID NO 4
<211> LENGTH: 8
<212> TYPE: PRT
<213> ORGANISM: Artificial Sequence
<220> FEATURE:
<223> OTHER INFORMATION: Target Peptide

<400> SEQUENCE: 4

Trp Phe His Gly Lys Leu Ser Arg
1               5

<210> SEQ ID NO 5
<211> LENGTH: 8
<212> TYPE: PRT
<213> ORGANISM: Artificial Sequence
<220> FEATURE:
<223> OTHER INFORMATION: Target Peptide

<400> SEQUENCE: 5

Trp Asn Val Gly Ser Ser Asn Arg
1               5

<210> SEQ ID NO 6
<211> LENGTH: 1210
<212> TYPE: PRT
<213> ORGANISM: Artificial Sequence
<220> FEATURE:
<223> OTHER INFORMATION: Consensus Target Peptide
<220> FEATURE:
<221> NAME/KEY: VARIANT
<222> LOCATION: (1)..(1)
<223> OTHER INFORMATION: Wherein Xaa is any amino acid.
<220> FEATURE:
<221> NAME/KEY: VARIANT
<222> LOCATION: (2)..(600)
<223> OTHER INFORMATION: Wherein Xaa is any amino acid or nothing.
<220> FEATURE:
<221> NAME/KEY: VARIANT
<222> LOCATION: (611)..(611)
<223> OTHER INFORMATION: Wherein Xaa is any amino acid.
<220> FEATURE:
<221> NAME/KEY: VARIANT
<222> LOCATION: (612)..(1210)
<223> OTHER INFORMATION: Wherein Xaa is any amino acid or nothing.

<400> SEQUENCE: 6

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa
    130                 135                 140
```

-continued

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa
            165                 170                 175

Xaa Xaa Xaa Xaa Xaa Xaa Xaa Xaa Xaa Xaa Xaa Xaa Xaa Xaa Xaa
        180                 185                 190

Xaa Xaa Xaa Xaa Xaa Xaa Xaa Xaa Xaa Xaa Xaa Xaa Xaa Xaa Xaa
    195                 200                 205

Xaa Xaa Xaa Xaa Xaa Xaa Xaa Xaa Xaa Xaa Xaa Xaa Xaa Xaa Xaa
210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa
            245                 250                 255

Xaa Xaa Xaa Xaa Xaa Xaa Xaa Xaa Xaa Xaa Xaa Xaa Xaa Xaa Xaa
        260                 265                 270

Xaa Xaa Xaa Xaa Xaa Xaa Xaa Xaa Xaa Xaa Xaa Xaa Xaa Xaa Xaa
    275                 280                 285

Xaa Xaa Xaa Xaa Xaa Xaa Xaa Xaa Xaa Xaa Xaa Xaa Xaa Xaa Xaa
290                 295                 300

Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
            325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
    355                 360                 365

Xaa Xaa Xaa Xaa Xaa Xaa Xaa Xaa Xaa Xaa Xaa Xaa Xaa Xaa Xaa
370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
            405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
    435                 440                 445

Xaa Xaa Xaa Xaa Xaa Xaa Xaa Xaa Xaa Xaa Xaa Xaa Xaa Xaa Xaa
450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
            485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Xaa
    515                 520                 525

Xaa Xaa Xaa Xaa Xaa Xaa Xaa Xaa Xaa Xaa Xaa Xaa Xaa Xaa Xaa
530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
            565                 570                 575

Xaa Xaa Xaa Xaa Xaa Xaa Xaa Xaa Xaa Xaa Xaa Xaa Xaa Xaa Xaa
                580                 585                 590

Xaa Xaa Xaa Xaa Xaa Xaa Xaa Gly Ser Gly Ile Phe Leu Glu Thr
            595                 600                 605

Ser Leu Xaa Xaa Xaa Xaa Xaa Xaa Xaa Xaa Xaa Xaa Xaa Xaa Xaa
        610                 615                 620

Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
                645                 650                 655

Xaa Xaa Xaa Xaa Xaa Xaa Xaa Xaa Xaa Xaa Xaa Xaa Xaa Xaa Xaa
                660                 665                 670

Xaa Xaa Xaa Xaa Xaa Xaa Xaa Xaa Xaa Xaa Xaa Xaa Xaa Xaa Xaa
                675                 680                 685

Xaa Xaa Xaa Xaa Xaa Xaa Xaa Xaa Xaa Xaa Xaa Xaa Xaa Xaa Xaa
                690                 695                 700

Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
                725                 730                 735

Xaa Xaa Xaa Xaa Xaa Xaa Xaa Xaa Xaa Xaa Xaa Xaa Xaa Xaa Xaa
                740                 745                 750

Xaa Xaa Xaa Xaa Xaa Xaa Xaa Xaa Xaa Xaa Xaa Xaa Xaa Xaa Xaa
                755                 760                 765

Xaa Xaa Xaa Xaa Xaa Xaa Xaa Xaa Xaa Xaa Xaa Xaa Xaa Xaa Xaa
                770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
                805                 810                 815

Xaa Xaa Xaa Xaa Xaa Xaa Xaa Xaa Xaa Xaa Xaa Xaa Xaa Xaa Xaa
                820                 825                 830

Xaa Xaa Xaa Xaa Xaa Xaa Xaa Xaa Xaa Xaa Xaa Xaa Xaa Xaa Xaa
                835                 840                 845

Xaa Xaa Xaa Xaa Xaa Xaa Xaa Xaa Xaa Xaa Xaa Xaa Xaa Xaa Xaa
850                 855                 860

Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa
                885                 890                 895

Xaa Xaa Xaa Xaa Xaa Xaa Xaa Xaa Xaa Xaa Xaa Xaa Xaa Xaa Xaa
                900                 905                 910

Xaa Xaa Xaa Xaa Xaa Xaa Xaa Xaa Xaa Xaa Xaa Xaa Xaa Xaa Xaa
                915                 920                 925

Xaa Xaa Xaa Xaa Xaa Xaa Xaa Xaa Xaa Xaa Xaa Xaa Xaa Xaa Xaa
                930                 935                 940

Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa
                965                 970                 975

Xaa Xaa Xaa Xaa Xaa Xaa Xaa Xaa Xaa Xaa Xaa Xaa Xaa Xaa Xaa
                980                 985                 990

Xaa Xaa Xaa Xaa Xaa Xaa Xaa Xaa  Xaa Xaa Xaa Xaa Xaa  Xaa Xaa Xaa

```
                 995                1000               1005

Xaa Xaa  Xaa Xaa Xaa Xaa Xaa  Xaa Xaa Xaa Xaa Xaa  Xaa Xaa Xaa
    1010                1015               1020

Xaa Xaa  Xaa Xaa Xaa Xaa Xaa  Xaa Xaa Xaa Xaa Xaa  Xaa Xaa Xaa
    1025                1030               1035

Xaa Xaa  Xaa Xaa Xaa Xaa Xaa  Xaa Xaa Xaa Xaa Xaa  Xaa Xaa Xaa
    1040                1045               1050

Xaa Xaa  Xaa Xaa Xaa Xaa Xaa  Xaa Xaa Xaa Xaa Xaa  Xaa Xaa Xaa
    1055                1060               1065

Xaa Xaa  Xaa Xaa Xaa Xaa Xaa  Xaa Xaa Xaa Xaa Xaa  Xaa Xaa Xaa
    1070                1075               1080

Xaa Xaa  Xaa Xaa Xaa Xaa Xaa  Xaa Xaa Xaa Xaa Xaa  Xaa Xaa Xaa
    1085                1090               1095

Xaa Xaa  Xaa Xaa Xaa Xaa Xaa  Xaa Xaa Xaa Xaa Xaa  Xaa Xaa Xaa
    1100                1105               1110

Xaa Xaa  Xaa Xaa Xaa Xaa Xaa  Xaa Xaa Xaa Xaa Xaa  Xaa Xaa Xaa
    1115                1120               1125

Xaa Xaa  Xaa Xaa Xaa Xaa Xaa  Xaa Xaa Xaa Xaa Xaa  Xaa Xaa Xaa
    1130                1135               1140

Xaa Xaa  Xaa Xaa Xaa Xaa Xaa  Xaa Xaa Xaa Xaa Xaa  Xaa Xaa Xaa
    1145                1150               1155

Xaa Xaa  Xaa Xaa Xaa Xaa Xaa  Xaa Xaa Xaa Xaa Xaa  Xaa Xaa Xaa
    1160                1165               1170

Xaa Xaa  Xaa Xaa Xaa Xaa Xaa  Xaa Xaa Xaa Xaa Xaa  Xaa Xaa Xaa
    1175                1180               1185

Xaa Xaa  Xaa Xaa Xaa Xaa Xaa  Xaa Xaa Xaa Xaa Xaa  Xaa Xaa Xaa
    1190                1195               1200

Xaa Xaa  Xaa Xaa Xaa Xaa Xaa
    1205                1210

<210> SEQ ID NO 7
<211> LENGTH: 78
<212> TYPE: DNA
<213> ORGANISM: Artificial Sequence
<220> FEATURE:
<223> OTHER INFORMATION: PCR Primer

<400> SEQUENCE: 7
gcgctgatca ggcggaggcg gatcaggagg aggaggatca ggcggaggag gatcaggatc      60
catgtccgac agcgagaa                                                   78

<210> SEQ ID NO 8
<211> LENGTH: 29
<212> TYPE: DNA
<213> ORGANISM: Artificial Sequence
<220> FEATURE:
<223> OTHER INFORMATION: PCR Primer

<400> SEQUENCE: 8
gcgcgaattc atttcttggc tttggcaga                                       29

<210> SEQ ID NO 9
<211> LENGTH: 1206
<212> TYPE: PRT
<213> ORGANISM: Artificial Sequence
<220> FEATURE:
<223> OTHER INFORMATION: Consensus Target Peptide
<220> FEATURE:
<221> NAME/KEY: VARIANT
<222> LOCATION: (1)..(1)
```

```
<223> OTHER INFORMATION: Wherein Xaa is any amino acid.
<220> FEATURE:
<221> NAME/KEY: VARIANT
<222> LOCATION: (2)..(600)
<223> OTHER INFORMATION: Wherein Xaa is any amino acid or nothing.
<220> FEATURE:
<221> NAME/KEY: VARIANT
<222> LOCATION: (602)..(602)
<223> OTHER INFORMATION: Wherein Xaa is any amino acid.
<220> FEATURE:
<221> NAME/KEY: VARIANT
<222> LOCATION: (605)..(605)
<223> OTHER INFORMATION: Wherein Xaa is any amino acid.
<220> FEATURE:
<221> NAME/KEY: VARIANT
<222> LOCATION: (607)..(607)
<223> OTHER INFORMATION: Wherein Xaa is any amino acid.
<220> FEATURE:
<221> NAME/KEY: VARIANT
<222> LOCATION: (608)..(1206)
<223> OTHER INFORMATION: Wherein Xaa is any amino acid or nothing.

<400> SEQUENCE: 9

Xaa Xaa Xaa Xaa Xaa Xaa Xaa Xaa Xaa Xaa Xaa Xaa Xaa Xaa Xaa Xaa
  1               5                  10                  15

Xaa Xaa Xaa Xaa Xaa Xaa Xaa Xaa Xaa Xaa Xaa Xaa Xaa Xaa Xaa Xaa
             20                  25                  30

Xaa Xaa Xaa Xaa Xaa Xaa Xaa Xaa Xaa Xaa Xaa Xaa Xaa Xaa Xaa Xaa
         35                  40                  45

Xaa Xaa Xaa Xaa Xaa Xaa Xaa Xaa Xaa Xaa Xaa Xaa Xaa Xaa Xaa Xaa
     50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Xaa Xaa Xaa Xaa Xaa
                 85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa Xaa
            260                 265                 270

Xaa Xaa Xaa Xaa Xaa Xaa Xaa Xaa Xaa Xaa Xaa Xaa Xaa Xaa Xaa Xaa
        275                 280                 285

Xaa Xaa Xaa Xaa Xaa Xaa Xaa Xaa Xaa Xaa Xaa Xaa Xaa Xaa Xaa Xaa
    290                 295                 300
```

```
Xaa Xaa Xaa Xaa Xaa Xaa Xaa Xaa Xaa Xaa Xaa Xaa Xaa Xaa Xaa Xaa
305                 310                 315                 320

Xaa Xaa Xaa Xaa Xaa Xaa Xaa Xaa Xaa Xaa Xaa Xaa Xaa Xaa Xaa
        325                 330                 335

Xaa Xaa Xaa Xaa Xaa Xaa Xaa Xaa Xaa Xaa Xaa Xaa Xaa Xaa Xaa
        340                 345                 350

Xaa Xaa Xaa Xaa Xaa Xaa Xaa Xaa Xaa Xaa Xaa Xaa Xaa Xaa Xaa
        355                 360                 365

Xaa Xaa Xaa Xaa Xaa Xaa Xaa Xaa Xaa Xaa Xaa Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Xaa Xaa Xaa Xaa Xaa Xaa
        405                 410                 415

Xaa Xaa Xaa Xaa Xaa Xaa Xaa Xaa Xaa Xaa Xaa Xaa Xaa Xaa Xaa
        420                 425                 430

Xaa Xaa Xaa Xaa Xaa Xaa Xaa Xaa Xaa Xaa Xaa Xaa Xaa Xaa Xaa
        435                 440                 445

Xaa Xaa Xaa Xaa Xaa Xaa Xaa Xaa Xaa Xaa Xaa Xaa Xaa Xaa Xaa
        450                 455                 460

Xaa Xaa Xaa Xaa Xaa Xaa Xaa Xaa Xaa Xaa Xaa Xaa Xaa Xaa Xaa Xaa
465                 470                 475                 480

Xaa Xaa Xaa Xaa Xaa Xaa Xaa Xaa Xaa Xaa Xaa Xaa Xaa Xaa Xaa
        485                 490                 495

Xaa Xaa Xaa Xaa Xaa Xaa Xaa Xaa Xaa Xaa Xaa Xaa Xaa Xaa Xaa
        500                 505                 510

Xaa Xaa Xaa Xaa Xaa Xaa Xaa Xaa Xaa Xaa Xaa Xaa Xaa Xaa Xaa
        515                 520                 525

Xaa Xaa Xaa Xaa Xaa Xaa Xaa Xaa Xaa Xaa Xaa Xaa Xaa Xaa Xaa
        530                 535                 540

Xaa Xaa Xaa Xaa Xaa Xaa Xaa Xaa Xaa Xaa Xaa Xaa Xaa Xaa Xaa Xaa
545                 550                 555                 560

Xaa Xaa Xaa Xaa Xaa Xaa Xaa Xaa Xaa Xaa Xaa Xaa Xaa Xaa Xaa
        565                 570                 575

Xaa Xaa Xaa Xaa Xaa Xaa Xaa Xaa Xaa Xaa Xaa Xaa Xaa Xaa Xaa
        580                 585                 590

Xaa Xaa Xaa Xaa Xaa Xaa Xaa Xaa Lys Xaa Leu Lys Xaa Leu Xaa Xaa
        595                 600                 605

Xaa Xaa Xaa Xaa Xaa Xaa Xaa Xaa Xaa Xaa Xaa Xaa Xaa Xaa Xaa
        610                 615                 620

Xaa Xaa Xaa Xaa Xaa Xaa Xaa Xaa Xaa Xaa Xaa Xaa Xaa Xaa Xaa Xaa
625                 630                 635                 640

Xaa Xaa Xaa Xaa Xaa Xaa Xaa Xaa Xaa Xaa Xaa Xaa Xaa Xaa Xaa
        645                 650                 655

Xaa Xaa Xaa Xaa Xaa Xaa Xaa Xaa Xaa Xaa Xaa Xaa Xaa Xaa Xaa
        660                 665                 670

Xaa Xaa Xaa Xaa Xaa Xaa Xaa Xaa Xaa Xaa Xaa Xaa Xaa Xaa Xaa
        675                 680                 685

Xaa Xaa Xaa Xaa Xaa Xaa Xaa Xaa Xaa Xaa Xaa Xaa Xaa Xaa Xaa
        690                 695                 700

Xaa Xaa Xaa Xaa Xaa Xaa Xaa Xaa Xaa Xaa Xaa Xaa Xaa Xaa Xaa Xaa
705                 710                 715                 720

Xaa Xaa Xaa Xaa Xaa Xaa Xaa Xaa Xaa Xaa Xaa Xaa Xaa Xaa Xaa
```

-continued

```
                725                 730                 735
Xaa Xaa Xaa Xaa Xaa Xaa Xaa Xaa Xaa Xaa Xaa Xaa Xaa Xaa Xaa
            740                 745                 750

Xaa Xaa Xaa Xaa Xaa Xaa Xaa Xaa Xaa Xaa Xaa Xaa Xaa Xaa Xaa
            755                 760                 765

Xaa Xaa Xaa Xaa Xaa Xaa Xaa Xaa Xaa Xaa Xaa Xaa Xaa Xaa Xaa
770                 775                 780

Xaa Xaa Xaa Xaa Xaa Xaa Xaa Xaa Xaa Xaa Xaa Xaa Xaa Xaa Xaa
785                 790                 795                 800

Xaa Xaa Xaa Xaa Xaa Xaa Xaa Xaa Xaa Xaa Xaa Xaa Xaa Xaa Xaa
            805                 810                 815

Xaa Xaa Xaa Xaa Xaa Xaa Xaa Xaa Xaa Xaa Xaa Xaa Xaa Xaa Xaa
            820                 825                 830

Xaa Xaa Xaa Xaa Xaa Xaa Xaa Xaa Xaa Xaa Xaa Xaa Xaa Xaa Xaa
            835                 840                 845

Xaa Xaa Xaa Xaa Xaa Xaa Xaa Xaa Xaa Xaa Xaa Xaa Xaa Xaa Xaa
        850                 855                 860

Xaa Xaa Xaa Xaa Xaa Xaa Xaa Xaa Xaa Xaa Xaa Xaa Xaa Xaa Xaa
865                 870                 875                 880

Xaa Xaa Xaa Xaa Xaa Xaa Xaa Xaa Xaa Xaa Xaa Xaa Xaa Xaa Xaa
            885                 890                 895

Xaa Xaa Xaa Xaa Xaa Xaa Xaa Xaa Xaa Xaa Xaa Xaa Xaa Xaa Xaa
            900                 905                 910

Xaa Xaa Xaa Xaa Xaa Xaa Xaa Xaa Xaa Xaa Xaa Xaa Xaa Xaa Xaa
            915                 920                 925

Xaa Xaa Xaa Xaa Xaa Xaa Xaa Xaa Xaa Xaa Xaa Xaa Xaa Xaa Xaa
            930                 935                 940

Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Xaa Xaa Xaa
            980                 985                 990

Xaa Xaa Xaa Xaa Xaa Xaa Xaa  Xaa Xaa Xaa Xaa Xaa  Xaa Xaa Xaa
            995                1000                1005

Xaa Xaa  Xaa Xaa Xaa Xaa Xaa  Xaa Xaa Xaa Xaa Xaa  Xaa Xaa Xaa
    1010                1015                1020

Xaa Xaa  Xaa Xaa Xaa Xaa Xaa  Xaa Xaa Xaa Xaa Xaa  Xaa Xaa Xaa
    1025                1030                1035

Xaa Xaa  Xaa Xaa Xaa Xaa Xaa  Xaa Xaa Xaa Xaa Xaa  Xaa Xaa Xaa
    1040                1045                1050

Xaa Xaa  Xaa Xaa Xaa Xaa Xaa  Xaa Xaa Xaa Xaa Xaa  Xaa Xaa Xaa
    1055                1060                1065

Xaa Xaa  Xaa Xaa Xaa Xaa Xaa  Xaa Xaa Xaa Xaa Xaa  Xaa Xaa Xaa
    1070                1075                1080

Xaa Xaa  Xaa Xaa Xaa Xaa Xaa  Xaa Xaa Xaa Xaa Xaa  Xaa Xaa Xaa
    1085                1090                1095

Xaa Xaa  Xaa Xaa Xaa Xaa Xaa  Xaa Xaa Xaa Xaa Xaa  Xaa Xaa Xaa
    1100                1105                1110

Xaa Xaa  Xaa Xaa Xaa Xaa Xaa  Xaa Xaa Xaa Xaa Xaa  Xaa Xaa Xaa
    1115                1120                1125

Xaa Xaa  Xaa Xaa Xaa Xaa Xaa  Xaa Xaa Xaa Xaa Xaa  Xaa Xaa Xaa
    1130                1135                1140
```

```
Xaa Xaa Xaa Xaa Xaa Xaa Xaa  Xaa Xaa Xaa Xaa Xaa  Xaa Xaa Xaa
    1145                1150                1155

Xaa Xaa Xaa Xaa Xaa Xaa Xaa  Xaa Xaa Xaa Xaa Xaa  Xaa Xaa Xaa
    1160                1165                1170

Xaa Xaa Xaa Xaa Xaa Xaa Xaa  Xaa Xaa Xaa Xaa Xaa  Xaa Xaa Xaa
    1175                1180                1185

Xaa Xaa Xaa Xaa Xaa Xaa Xaa  Xaa Xaa Xaa Xaa Xaa  Xaa Xaa Xaa
    1190                1195                1200

Xaa Xaa Xaa
    1205

<210> SEQ ID NO 10
<211> LENGTH: 826
<212> TYPE: PRT
<213> ORGANISM: Artificial Sequence
<220> FEATURE:
<223> OTHER INFORMATION: Consensus Target Peptide

<400> SEQUENCE: 10

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125

Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
        275                 280                 285

Lys Thr His His Asp Met Phe Thr Lys Gly Gln Val Thr Thr Gly Gln
```

-continued

```
            290                 295                 300
Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
                340                 345                 350

Ser Leu Gln Gln Thr Glu Cys Val Leu Lys Pro Val Glu Ser Ser Asp
                355                 360                 365

Met Lys Met Thr Gln Leu Phe Thr Lys Val Glu Ser Glu Asp Thr Ser
            370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                    405                 410                 415

Asp Thr Glu Thr Asp Asp Gln Gln Leu Glu Glu Val Pro Leu Tyr Asn
                420                 425                 430

Asp Val Met Leu Pro Ser Pro Asn Glu Lys Leu Gln Asn Ile Asn Leu
            435                 440                 445

Ala Met Ser Pro Leu Pro Thr Ala Glu Thr Pro Lys Pro Leu Arg Ser
450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                    485                 490                 495

Gln Thr Pro Ser Pro Ser Asp Gly Ser Thr Arg Gln Ser Ser Pro Glu
                500                 505                 510

Pro Asn Ser Pro Ser Glu Tyr Cys Phe Tyr Val Asp Ser Asp Met Val
            515                 520                 525

Asn Glu Phe Lys Leu Glu Leu Val Glu Lys Leu Phe Ala Glu Asp Thr
            530                 535                 540

Glu Ala Lys Asn Pro Phe Ser Thr Gln Asp Thr Asp Leu Asp Leu Glu
545                 550                 555                 560

Met Leu Ala Pro Tyr Ile Pro Met Asp Asp Asp Phe Gln Leu Arg Ser
                565                 570                 575

Phe Asp Gln Leu Ser Pro Leu Glu Ser Ser Ser Ala Ser Pro Glu Ser
                580                 585                 590

Ala Ser Pro Gln Ser Thr Val Thr Val Phe Gln Gln Thr Gln Ile Gln
                595                 600                 605

Glu Pro Thr Ala Asn Ala Thr Thr Thr Thr Ala Thr Thr Asp Glu Leu
610                 615                 620

Lys Thr Val Thr Lys Asp Arg Met Glu Asp Ile Lys Ile Leu Ile Ala
625                 630                 635                 640

Ser Pro Ser Pro Thr His Ile His Lys Glu Thr Thr Ser Ala Thr Ser
                    645                 650                 655

Ser Pro Tyr Arg Asp Thr Gln Ser Arg Thr Ala Ser Pro Asn Arg Ala
                660                 665                 670

Gly Lys Gly Val Ile Glu Gln Thr Glu Lys Ser His Pro Arg Ser Pro
                675                 680                 685

Asn Val Leu Ser Val Ala Leu Ser Gln Arg Thr Thr Val Pro Glu Glu
            690                 695                 700

Glu Leu Asn Pro Lys Ile Leu Ala Leu Gln Asn Ala Gln Arg Lys Arg
705                 710                 715                 720
```

-continued

```
Lys Met Glu His Asp Gly Ser Leu Phe Gln Ala Val Gly Ile Gly Thr
            725                 730                 735

Leu Leu Gln Gln Pro Asp Asp His Ala Ala Thr Thr Ser Leu Ser Trp
        740                 745                 750

Lys Arg Val Lys Gly Cys Lys Ser Ser Glu Gln Asn Gly Met Glu Gln
    755                 760                 765

Lys Thr Ile Ile Leu Ile Pro Ser Asp Leu Ala Cys Arg Leu Leu Gly
770                 775                 780

Gln Ser Met Asp Glu Ser Gly Leu Pro Gln Leu Thr Ser Tyr Asp Cys
785                 790                 795                 800

Glu Val Asn Ala Pro Ile Gln Gly Ser Arg Asn Leu Leu Gln Gly Glu
                805                 810                 815

Glu Leu Leu Arg Ala Leu Asp Gln Val Asn
            820                 825

<210> SEQ ID NO 11
<211> LENGTH: 1208
<212> TYPE: PRT
<213> ORGANISM: Artificial Sequence
<220> FEATURE:
<223> OTHER INFORMATION: Consensus Binding Peptide
<220> FEATURE:
<221> NAME/KEY: VARIANT
<222> LOCATION: (1)..(1)
<223> OTHER INFORMATION: Wherein Xaa is any amino acid.
<220> FEATURE:
<221> NAME/KEY: VARIANT
<222> LOCATION: (2)..(600)
<223> OTHER INFORMATION: Wherein Xaa is any amino acid or nothing.
<220> FEATURE:
<221> NAME/KEY: VARIANT
<222> LOCATION: (601)..(601)
<223> OTHER INFORMATION: Wherein Xaa is Gly, Ala, Val, Leu, Ile, Pro,
      Met, Phe, or Trp.
<220> FEATURE:
<221> NAME/KEY: VARIANT
<222> LOCATION: (603)..(603)
<223> OTHER INFORMATION: Wherein Xaa is Gly, Ala, Val, Leu, Ile, Pro,
      Met, Phe, or Trp.
<220> FEATURE:
<221> NAME/KEY: VARIANT
<222> LOCATION: (605)..(605)
<223> OTHER INFORMATION: Wherein Xaa is Ser, Thr, or Tyr.
<220> FEATURE:
<221> NAME/KEY: VARIANT
<222> LOCATION: (606)..(608)
<223> OTHER INFORMATION: Wherein Xaa is Gly, Ala, Val, Leu, Ile, Pro,
      Met, Phe, or Trp.
<220> FEATURE:
<221> NAME/KEY: VARIANT
<222> LOCATION: (609)..(609)
<223> OTHER INFORMATION: Wherein Xaa is any amino acid.
<220> FEATURE:
<221> NAME/KEY: VARIANT
<222> LOCATION: (610)..(1208)
<223> OTHER INFORMATION: Wherein Xaa is any amino acid or nothing.

<400> SEQUENCE: 11

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
        50                  55                  60

Xaa Xaa Xaa Xaa Xaa Xaa Xaa Xaa Xaa Xaa Xaa Xaa Xaa Xaa Xaa Xaa
65                  70                  75                  80
```

Xaa Xaa Xaa Xaa Xaa Xaa Xaa Xaa Xaa Xaa Xaa Xaa Xaa Xaa Xaa
                85                   90                   95

Xaa Xaa Xaa Xaa Xaa Xaa Xaa Xaa Xaa Xaa Xaa Xaa Xaa Xaa Xaa
               100                  105                  110

Xaa Xaa Xaa Xaa Xaa Xaa Xaa Xaa Xaa Xaa Xaa Xaa Xaa Xaa Xaa
               115                  120                  125

Xaa Xaa Xaa Xaa Xaa Xaa Xaa Xaa Xaa Xaa Xaa Xaa Xaa Xaa Xaa
               130                  135                  140

Xaa Xaa Xaa Xaa Xaa Xaa Xaa Xaa Xaa Xaa Xaa Xaa Xaa Xaa Xaa
145                 150                  155                 160

Xaa Xaa Xaa Xaa Xaa Xaa Xaa Xaa Xaa Xaa Xaa Xaa Xaa Xaa Xaa
               165                  170                  175

Xaa Xaa Xaa Xaa Xaa Xaa Xaa Xaa Xaa Xaa Xaa Xaa Xaa Xaa Xaa
               180                  185                  190

Xaa Xaa Xaa Xaa Xaa Xaa Xaa Xaa Xaa Xaa Xaa Xaa Xaa Xaa Xaa
               195                  200                  205

Xaa Xaa Xaa Xaa Xaa Xaa Xaa Xaa Xaa Xaa Xaa Xaa Xaa Xaa Xaa
               210                  215                  220

Xaa Xaa Xaa Xaa Xaa Xaa Xaa Xaa Xaa Xaa Xaa Xaa Xaa Xaa Xaa
225                 230                  235                 240

Xaa Xaa Xaa Xaa Xaa Xaa Xaa Xaa Xaa Xaa Xaa Xaa Xaa Xaa Xaa
               245                  250                  255

Xaa Xaa Xaa Xaa Xaa Xaa Xaa Xaa Xaa Xaa Xaa Xaa Xaa Xaa Xaa
               260                  265                  270

Xaa Xaa Xaa Xaa Xaa Xaa Xaa Xaa Xaa Xaa Xaa Xaa Xaa Xaa Xaa
               275                  280                  285

Xaa Xaa Xaa Xaa Xaa Xaa Xaa Xaa Xaa Xaa Xaa Xaa Xaa Xaa Xaa
               290                  295                  300

Xaa Xaa Xaa Xaa Xaa Xaa Xaa Xaa Xaa Xaa Xaa Xaa Xaa Xaa Xaa
305                 310                  315                 320

Xaa Xaa Xaa Xaa Xaa Xaa Xaa Xaa Xaa Xaa Xaa Xaa Xaa Xaa Xaa
               325                  330                  335

Xaa Xaa Xaa Xaa Xaa Xaa Xaa Xaa Xaa Xaa Xaa Xaa Xaa Xaa Xaa
               340                  345                  350

Xaa Xaa Xaa Xaa Xaa Xaa Xaa Xaa Xaa Xaa Xaa Xaa Xaa Xaa Xaa
               355                  360                  365

Xaa Xaa Xaa Xaa Xaa Xaa Xaa Xaa Xaa Xaa Xaa Xaa Xaa Xaa Xaa
               370                  375                  380

Xaa Xaa Xaa Xaa Xaa Xaa Xaa Xaa Xaa Xaa Xaa Xaa Xaa Xaa Xaa
385                 390                  395                 400

Xaa Xaa Xaa Xaa Xaa Xaa Xaa Xaa Xaa Xaa Xaa Xaa Xaa Xaa Xaa
               405                  410                  415

Xaa Xaa Xaa Xaa Xaa Xaa Xaa Xaa Xaa Xaa Xaa Xaa Xaa Xaa Xaa
               420                  425                  430

Xaa Xaa Xaa Xaa Xaa Xaa Xaa Xaa Xaa Xaa Xaa Xaa Xaa Xaa Xaa
               435                  440                  445

Xaa Xaa Xaa Xaa Xaa Xaa Xaa Xaa Xaa Xaa Xaa Xaa Xaa Xaa Xaa
               450                  455                  460

Xaa Xaa Xaa Xaa Xaa Xaa Xaa Xaa Xaa Xaa Xaa Xaa Xaa Xaa Xaa
465                 470                  475                 480

Xaa Xaa Xaa Xaa Xaa Xaa Xaa Xaa Xaa Xaa Xaa Xaa Xaa Xaa Xaa
               485                  490                  495

Xaa Xaa Xaa Xaa Xaa Xaa Xaa Xaa Xaa Xaa Xaa Xaa Xaa Xaa Xaa

-continued

```
                500                 505                 510
Xaa Xaa Xaa Xaa Xaa Xaa Xaa Xaa Xaa Xaa Xaa Xaa Xaa Xaa Xaa
            515                 520                 525
Xaa Xaa Xaa Xaa Xaa Xaa Xaa Xaa Xaa Xaa Xaa Xaa Xaa Xaa Xaa
            530                 535                 540
Xaa Xaa Xaa Xaa Xaa Xaa Xaa Xaa Xaa Xaa Xaa Xaa Xaa Xaa Xaa
545                 550                 555                 560
Xaa Xaa Xaa Xaa Xaa Xaa Xaa Xaa Xaa Xaa Xaa Xaa Xaa Xaa Xaa
            565                 570                 575
Xaa Xaa Xaa Xaa Xaa Xaa Xaa Xaa Xaa Xaa Xaa Xaa Xaa Xaa Xaa
            580                 585                 590
Xaa Xaa Xaa Xaa Xaa Xaa Xaa Xaa Xaa Leu Xaa Pro Xaa Xaa Xaa
            595                 600                 605
Xaa Xaa Xaa Xaa Xaa Xaa Xaa Xaa Xaa Xaa Xaa Xaa Xaa Xaa Xaa
            610                 615                 620
Xaa Xaa Xaa Xaa Xaa Xaa Xaa Xaa Xaa Xaa Xaa Xaa Xaa Xaa Xaa
625                 630                 635                 640
Xaa Xaa Xaa Xaa Xaa Xaa Xaa Xaa Xaa Xaa Xaa Xaa Xaa Xaa Xaa
            645                 650                 655
Xaa Xaa Xaa Xaa Xaa Xaa Xaa Xaa Xaa Xaa Xaa Xaa Xaa Xaa Xaa
            660                 665                 670
Xaa Xaa Xaa Xaa Xaa Xaa Xaa Xaa Xaa Xaa Xaa Xaa Xaa Xaa Xaa
            675                 680                 685
Xaa Xaa Xaa Xaa Xaa Xaa Xaa Xaa Xaa Xaa Xaa Xaa Xaa Xaa Xaa
            690                 695                 700
Xaa Xaa Xaa Xaa Xaa Xaa Xaa Xaa Xaa Xaa Xaa Xaa Xaa Xaa Xaa
705                 710                 715                 720
Xaa Xaa Xaa Xaa Xaa Xaa Xaa Xaa Xaa Xaa Xaa Xaa Xaa Xaa Xaa
            725                 730                 735
Xaa Xaa Xaa Xaa Xaa Xaa Xaa Xaa Xaa Xaa Xaa Xaa Xaa Xaa Xaa
            740                 745                 750
Xaa Xaa Xaa Xaa Xaa Xaa Xaa Xaa Xaa Xaa Xaa Xaa Xaa Xaa Xaa
            755                 760                 765
Xaa Xaa Xaa Xaa Xaa Xaa Xaa Xaa Xaa Xaa Xaa Xaa Xaa Xaa Xaa
            770                 775                 780
Xaa Xaa Xaa Xaa Xaa Xaa Xaa Xaa Xaa Xaa Xaa Xaa Xaa Xaa Xaa
785                 790                 795                 800
Xaa Xaa Xaa Xaa Xaa Xaa Xaa Xaa Xaa Xaa Xaa Xaa Xaa Xaa Xaa
            805                 810                 815
Xaa Xaa Xaa Xaa Xaa Xaa Xaa Xaa Xaa Xaa Xaa Xaa Xaa Xaa Xaa
            820                 825                 830
Xaa Xaa Xaa Xaa Xaa Xaa Xaa Xaa Xaa Xaa Xaa Xaa Xaa Xaa Xaa
            835                 840                 845
Xaa Xaa Xaa Xaa Xaa Xaa Xaa Xaa Xaa Xaa Xaa Xaa Xaa Xaa Xaa
            850                 855                 860
Xaa Xaa Xaa Xaa Xaa Xaa Xaa Xaa Xaa Xaa Xaa Xaa Xaa Xaa Xaa
865                 870                 875                 880
Xaa Xaa Xaa Xaa Xaa Xaa Xaa Xaa Xaa Xaa Xaa Xaa Xaa Xaa Xaa
            885                 890                 895
Xaa Xaa Xaa Xaa Xaa Xaa Xaa Xaa Xaa Xaa Xaa Xaa Xaa Xaa Xaa
            900                 905                 910
Xaa Xaa Xaa Xaa Xaa Xaa Xaa Xaa Xaa Xaa Xaa Xaa Xaa Xaa Xaa
            915                 920                 925
```

```
Xaa Xaa Xaa Xaa Xaa Xaa Xaa Xaa Xaa Xaa Xaa Xaa Xaa Xaa Xaa
        930                 935                 940

Xaa Xaa Xaa Xaa Xaa Xaa Xaa Xaa Xaa Xaa Xaa Xaa Xaa Xaa Xaa
945                 950                 955                 960

Xaa Xaa Xaa Xaa Xaa Xaa Xaa Xaa Xaa Xaa Xaa Xaa Xaa Xaa Xaa
            965                 970                 975

Xaa Xaa Xaa Xaa Xaa Xaa Xaa Xaa Xaa Xaa Xaa Xaa Xaa Xaa Xaa
        980                 985                 990

Xaa Xaa Xaa Xaa Xaa Xaa Xaa Xaa Xaa Xaa Xaa Xaa Xaa Xaa Xaa
    995                 1000                1005

Xaa Xaa Xaa Xaa Xaa Xaa Xaa Xaa Xaa Xaa Xaa Xaa Xaa Xaa Xaa
1010                1015                1020

Xaa Xaa Xaa Xaa Xaa Xaa Xaa Xaa Xaa Xaa Xaa Xaa Xaa Xaa Xaa
1025                1030                1035

Xaa Xaa Xaa Xaa Xaa Xaa Xaa Xaa Xaa Xaa Xaa Xaa Xaa Xaa Xaa
1040                1045                1050

Xaa Xaa Xaa Xaa Xaa Xaa Xaa Xaa Xaa Xaa Xaa Xaa Xaa Xaa Xaa
1055                1060                1065

Xaa Xaa Xaa Xaa Xaa Xaa Xaa Xaa Xaa Xaa Xaa Xaa Xaa Xaa Xaa
1070                1075                1080

Xaa Xaa Xaa Xaa Xaa Xaa Xaa Xaa Xaa Xaa Xaa Xaa Xaa Xaa Xaa
1085                1090                1095

Xaa Xaa Xaa Xaa Xaa Xaa Xaa Xaa Xaa Xaa Xaa Xaa Xaa Xaa Xaa
1100                1105                1110

Xaa Xaa Xaa Xaa Xaa Xaa Xaa Xaa Xaa Xaa Xaa Xaa Xaa Xaa Xaa
1115                1120                1125

Xaa Xaa Xaa Xaa Xaa Xaa Xaa Xaa Xaa Xaa Xaa Xaa Xaa Xaa Xaa
1130                1135                1140

Xaa Xaa Xaa Xaa Xaa Xaa Xaa Xaa Xaa Xaa Xaa Xaa Xaa Xaa Xaa
1145                1150                1155

Xaa Xaa Xaa Xaa Xaa Xaa Xaa Xaa Xaa Xaa Xaa Xaa Xaa Xaa Xaa
1160                1165                1170

Xaa Xaa Xaa Xaa Xaa Xaa Xaa Xaa Xaa Xaa Xaa Xaa Xaa Xaa Xaa
1175                1180                1185

Xaa Xaa Xaa Xaa Xaa Xaa Xaa Xaa Xaa Xaa Xaa Xaa Xaa Xaa Xaa
1190                1195                1200

Xaa Xaa Xaa Xaa Xaa
1205

<210> SEQ ID NO 12
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 12

Met Leu Ala Pro Tyr Ile Pro Met
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 13
```

```
Ala Leu Ala Pro Tyr Ile Pro Met
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 14

Met Ala Ala Pro Tyr Ile Pro Met
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 15

Met Leu Ala Ala Tyr Ile Pro Met
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 16

Met Leu Ala Pro Ala Ile Pro Met
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 17

Met Leu Ala Pro Tyr Ala Pro Met
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 18

Met Leu Ala Pro Tyr Ile Ala Met
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 19

Met Leu Ala Pro Tyr Ile Pro Ala
1               5
```

```
<210> SEQ ID NO 20
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 20

Ala Ala Ala Ala Ala Ala Ala Ala
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (4)..(4)
<223> OTHER INFORMATION: Wherein X is a hydroxylated Proline

<400> SEQUENCE: 21

Met Leu Ala Xaa Tyr Ile Pro Met
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: (4)..(4)
<223> OTHER INFORMATION: Wherein Xaa is hydroxylated Proline

<400> SEQUENCE: 22

Met Ala Ala Xaa Tyr Ile Pro Met
1               5

<210> SEQ ID NO 23
<211> LENGTH: 826
<212> TYPE: PRT
<213> ORGANISM: Homo sapiens

<400> SEQUENCE: 23

Met Glu Gly Ala Gly Gly Ala Asn Asp Lys Lys Lys Ile Ser Ser Glu
1               5                   10                  15

Arg Arg Lys Glu Lys Ser Arg Asp Ala Ala Arg Ser Arg Arg Ser Lys
            20                  25                  30

Glu Ser Glu Val Phe Tyr Glu Leu Ala His Gln Leu Pro Leu Pro His
        35                  40                  45

Asn Val Ser Ser His Leu Asp Lys Ala Ser Val Met Arg Leu Thr Ile
    50                  55                  60

Ser Tyr Leu Arg Val Arg Lys Leu Leu Asp Ala Gly Asp Leu Asp Ile
65                  70                  75                  80

Glu Asp Asp Met Lys Ala Gln Met Asn Cys Phe Tyr Leu Lys Ala Leu
                85                  90                  95

Asp Gly Phe Val Met Val Leu Thr Asp Asp Gly Asp Met Ile Tyr Ile
            100                 105                 110

Ser Asp Asn Val Asn Lys Tyr Met Gly Leu Thr Gln Phe Glu Leu Thr
        115                 120                 125
```

-continued

```
Gly His Ser Val Phe Asp Phe Thr His Pro Cys Asp His Glu Glu Met
    130                 135                 140

Arg Glu Met Leu Thr His Arg Asn Gly Leu Val Lys Lys Gly Lys Glu
145                 150                 155                 160

Gln Asn Thr Gln Arg Ser Phe Phe Leu Arg Met Lys Cys Thr Leu Thr
                165                 170                 175

Ser Arg Gly Arg Thr Met Asn Ile Lys Ser Ala Thr Trp Lys Val Leu
            180                 185                 190

His Cys Thr Gly His Ile His Val Tyr Asp Thr Asn Ser Asn Gln Pro
        195                 200                 205

Gln Cys Gly Tyr Lys Lys Pro Pro Met Thr Cys Leu Val Leu Ile Cys
    210                 215                 220

Glu Pro Ile Pro His Pro Ser Asn Ile Glu Ile Pro Leu Asp Ser Lys
225                 230                 235                 240

Thr Phe Leu Ser Arg His Ser Leu Asp Met Lys Phe Ser Tyr Cys Asp
                245                 250                 255

Glu Arg Ile Thr Glu Leu Met Gly Tyr Glu Pro Glu Glu Leu Leu Gly
            260                 265                 270

Arg Ser Ile Tyr Glu Tyr Tyr His Ala Leu Asp Ser Asp His Leu Thr
275                 280                 285

Lys Thr His His Asp Met Phe Thr Lys Gly Gln Val Thr Thr Gly Gln
    290                 295                 300

Tyr Arg Met Leu Ala Lys Arg Gly Gly Tyr Val Trp Val Glu Thr Gln
305                 310                 315                 320

Ala Thr Val Ile Tyr Asn Thr Lys Asn Ser Gln Pro Gln Cys Ile Val
                325                 330                 335

Cys Val Asn Tyr Val Val Ser Gly Ile Ile Gln His Asp Leu Ile Phe
            340                 345                 350

Ser Leu Gln Gln Thr Glu Cys Val Leu Lys Pro Val Glu Ser Ser Asp
        355                 360                 365

Met Lys Met Thr Gln Leu Phe Thr Lys Val Glu Ser Glu Asp Thr Ser
    370                 375                 380

Ser Leu Phe Asp Lys Leu Lys Lys Glu Pro Asp Ala Leu Thr Leu Leu
385                 390                 395                 400

Ala Pro Ala Ala Gly Asp Thr Ile Ile Ser Leu Asp Phe Gly Ser Asn
                405                 410                 415

Asp Thr Glu Thr Asp Asp Gln Gln Leu Glu Glu Val Pro Leu Tyr Asn
            420                 425                 430

Asp Val Met Leu Pro Ser Pro Asn Glu Lys Leu Gln Asn Ile Asn Leu
        435                 440                 445

Ala Met Ser Pro Leu Pro Thr Ala Glu Thr Pro Lys Pro Leu Arg Ser
    450                 455                 460

Ser Ala Asp Pro Ala Leu Asn Gln Glu Val Ala Leu Lys Leu Glu Pro
465                 470                 475                 480

Asn Pro Glu Ser Leu Glu Leu Ser Phe Thr Met Pro Gln Ile Gln Asp
                485                 490                 495

Gln Thr Pro Ser Pro Ser Asp Gly Ser Thr Arg Gln Ser Ser Pro Glu
            500                 505                 510

Pro Asn Ser Pro Ser Glu Tyr Cys Phe Tyr Val Asp Ser Asp Met Val
        515                 520                 525

Asn Glu Phe Lys Leu Glu Leu Val Glu Lys Leu Phe Ala Glu Asp Thr
    530                 535                 540

Glu Ala Lys Asn Pro Phe Ser Thr Gln Asp Thr Asp Leu Asp Leu Glu
545                 550                 555                 560
```

-continued

```
Met Leu Ala Pro Tyr Ile Pro Met Asp Asp Phe Gln Leu Arg Ser
            565             570             575
Phe Asp Gln Leu Ser Pro Leu Glu Ser Ser Ala Ser Pro Glu Ser
            580             585             590
Ala Ser Pro Gln Ser Thr Val Thr Val Phe Gln Gln Thr Gln Ile Gln
            595             600             605
Glu Pro Thr Ala Asn Ala Thr Thr Thr Thr Ala Thr Thr Asp Glu Leu
            610             615             620
Lys Thr Val Thr Lys Asp Arg Met Glu Asp Ile Lys Ile Leu Ile Ala
625             630             635             640
Ser Pro Ser Pro Thr His Ile His Lys Glu Thr Thr Ser Ala Thr Ser
            645             650             655
Ser Pro Tyr Arg Asp Thr Gln Ser Arg Thr Ala Ser Pro Asn Arg Ala
            660             665             670
Gly Lys Gly Val Ile Glu Gln Thr Glu Lys Ser His Pro Arg Ser Pro
            675             680             685
Asn Val Leu Ser Val Ala Leu Ser Gln Arg Thr Thr Val Pro Glu Glu
690             695             700
Glu Leu Asn Pro Lys Ile Leu Ala Leu Gln Asn Ala Gln Arg Lys Arg
705             710             715             720
Lys Met Glu His Asp Gly Ser Leu Phe Gln Ala Val Gly Ile Gly Thr
            725             730             735
Leu Leu Gln Gln Pro Asp Asp His Ala Ala Thr Thr Ser Leu Ser Trp
            740             745             750
Lys Arg Val Lys Gly Cys Lys Ser Ser Glu Gln Asn Gly Met Glu Gln
            755             760             765
Lys Thr Ile Ile Leu Ile Pro Ser Asp Leu Ala Cys Arg Leu Leu Gly
770             775             780
Gln Ser Met Asp Glu Ser Gly Leu Pro Gln Leu Thr Ser Tyr Asp Cys
785             790             795             800
Glu Val Asn Ala Pro Ile Gln Gly Ser Arg Asn Leu Leu Gln Gly Glu
            805             810             815
Glu Leu Leu Arg Ala Leu Asp Gln Val Asn
            820             825
```